US010815460B2

(12) United States Patent
Freedman et al.

(10) Patent No.: US 10,815,460 B2
(45) Date of Patent: Oct. 27, 2020

(54) THREE-DIMENSIONAL DIFFERENTIATION OF EPIBLAST SPHEROIDS TO KIDNEY ORGANOIDS MODELS STAGE-SPECIFIC EPITHELIAL PHYSIOLOGY, MORPHOGENESIS, AND DISEASE

(71) Applicant: THE BRIGHAM AND WOMEN'S HOSPITAL, INC., Boston, MA (US)

(72) Inventors: Benjamin S. Freedman, Boston, MA (US); Joseph V. Bonventre, Boston, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 15/756,846

(22) PCT Filed: Sep. 2, 2016

(86) PCT No.: PCT/US2016/050271
§ 371 (c)(1),
(2) Date: Mar. 1, 2018

(87) PCT Pub. No.: WO2017/041041
PCT Pub. Date: Mar. 9, 2017

(65) Prior Publication Data
US 2018/0245050 A1 Aug. 30, 2018

Related U.S. Application Data

(60) Provisional application No. 62/213,740, filed on Sep. 3, 2015.

(51) Int. Cl.
C12N 5/071 (2010.01)
G01N 33/50 (2006.01)
A61K 35/44 (2015.01)
A61K 35/22 (2015.01)

(52) U.S. Cl.
CPC ............ C12N 5/0686 (2013.01); A61K 35/22 (2013.01); A61K 35/44 (2013.01); C12N 5/0684 (2013.01); G01N 33/5088 (2013.01); C12N 2500/90 (2013.01); C12N 2501/727 (2013.01); C12N 2501/999 (2013.01); C12N 2506/02 (2013.01); C12N 2506/03 (2013.01); C12N 2506/45 (2013.01); C12N 2513/00 (2013.01)

(58) Field of Classification Search
CPC ............ C12N 5/0686; C12N 2501/115; C12N 2501/119; C12N 2501/16; C12N 2501/999; C12N 2503/02; C12N 2503/04; C12N 2506/02; C12N 2506/45; C12N 2513/00
See application file for complete search history.

(56) References Cited

U.S. PATENT DOCUMENTS

2011/0305672 A1 12/2011 Dalton
2013/0157368 A1 6/2013 Buensuceso
2014/0363888 A1 12/2014 Osafune
2016/0304838 A1* 10/2016 Nishinakamura .... C12N 5/0671

FOREIGN PATENT DOCUMENTS

| WO | 2010/042669 A2 | 4/2010 | |
| WO | WO-2011077894 A1 * | 6/2011 | ........... C12N 5/0062 |
| WO | 2013/094771 A1 | 6/2013 | |
| WO | 2014/182885 A2 | 11/2014 | |
| WO | 2014197934 A1 | 12/2014 | |
| WO | 2015/056756 A1 | 4/2015 | |
| WO | 2015/130935 A1 | 9/2015 | |

OTHER PUBLICATIONS

Brown et al., "A Synthetic Niche for Nephron Progenitor Cells", Developmental Cell 34:229-241 (2015).
Cerdan et al., "Activin A Promotes Hematopoietic Fated Mesoderm Development Through Upregulation of Brachyury in Human Embryonic Stem Cells", Stem Cells and Development 21(15):2866-2877 (2012).
Cirio et al., "Lhx1 is Required for Specification of the Renal Progenitor Cell Field", PLoS One 6(4):e18858 (2011). (12 pages).
Lei et al., "A fully defined and scalable 3D culture system for human pluripotent stem cell expansion and differentiation", Proceedings of the National Academy of Sciences E5039-E5048 (2013).
Lin et al., "Subfractionation of Differentiating Human Embryonic Stem Cell Populations Allows the Isolation of a Mesodermal Population Enriched for Intermediate Mesoderm and Putative Renal Progenitors", Stem Cells and Development 19(10):1637-1648 (2010).
Mae et al., "Monitoring and robust induction of nephrogenic intermediate mesoderm from human pluripotent stem cells", Nature Communications 4:1367 (2013). (23 pages).
Morizane et al., "Directed Differentiation of Pluripotent Stem Cells into Kidney", Biomarker Insights 10(S1):147-152 (2015).
Mount, "Thick Ascending Limb of the Loop of Henle", Clinical Journal of the American Society of Nephrology 9:1974-1986 (2014).
Musunuru, "Genome editing of human pluripotent stem cells to generate human cellular disease models", Disease Models & Mechanisms 6:896-904 (2013).
Prozialeck et al., "Differential expression of E-cadherin, N-cadherin and beta-catenin in proximal and distal segments of the rat nephron.", BMC Physiology 4:10 (2004). (14 pages).
Song et al., "The Directed Differentiation of Human iPS Cells into Kidney Podocytes", Plos One 7(9):e46453 (2012). (9 pages).

(Continued)

Primary Examiner — Titilayo Moloye
(74) Attorney, Agent, or Firm — Nixon Peabody LLP; David S. Resnick; Teresa A. Ptashka

(57) ABSTRACT

Human pluripotent stem cells (hPSCs) have dual value as microphysiological laboratory models and regenerative therapeutics. hPSCs are epithelial cells, but the extent to which hPSCs and descendant epithelia can reconstitute lineage-specific functions remains poorly understood. Here the Inventors show that hPSCs in three-dimensional cultures and their differentiated descendants can functionally recapitulate tissue-specific epithelial morphogenesis, physiology, and disease.

14 Claims, 79 Drawing Sheets
Specification includes a Sequence Listing.

(56) References Cited

OTHER PUBLICATIONS

Wang et al., "Aquaporin-1 retards renal cyst development in polycystic kidney disease by inhibition of Wnt signaling", The FASEB Journal 29(4):1551-1563 (2015).
Xiao et al., "Cell death, cavitation and spontaneous multi-differentiation of dental pulp stem cells-derived spheroids in vitro: A journey to survival and organogenesis", Biology of the Cell 106:405-419 (2014).
Xia et al., "The generation of kidney organoids by differentation of human pluripotent cells to urtertic bud progenitor-like cells", Nature Protocols 9:11 2693-2704 (2014).
Lam et al., "Rapid and Efficient Differentiation of Human Pluripotent Stem Cells into Intermediate Mesoderm That Forms Tubules Expressing Kidney Proximal Tubular Markers", Journal of the American Society of Nephrology 25:6 1211-1225 (2013).
Freedman et al., "Modelling kidney disease with CRISPR-mutant kidney organoids derived from human pluripotent spheroids", Nature Communications 6:1 (2015).
Siller et al., "Modeling human disease with pluripotent stem cells", Current Gene Therapy 13(2):99-110 (2013).

\* cited by examiner

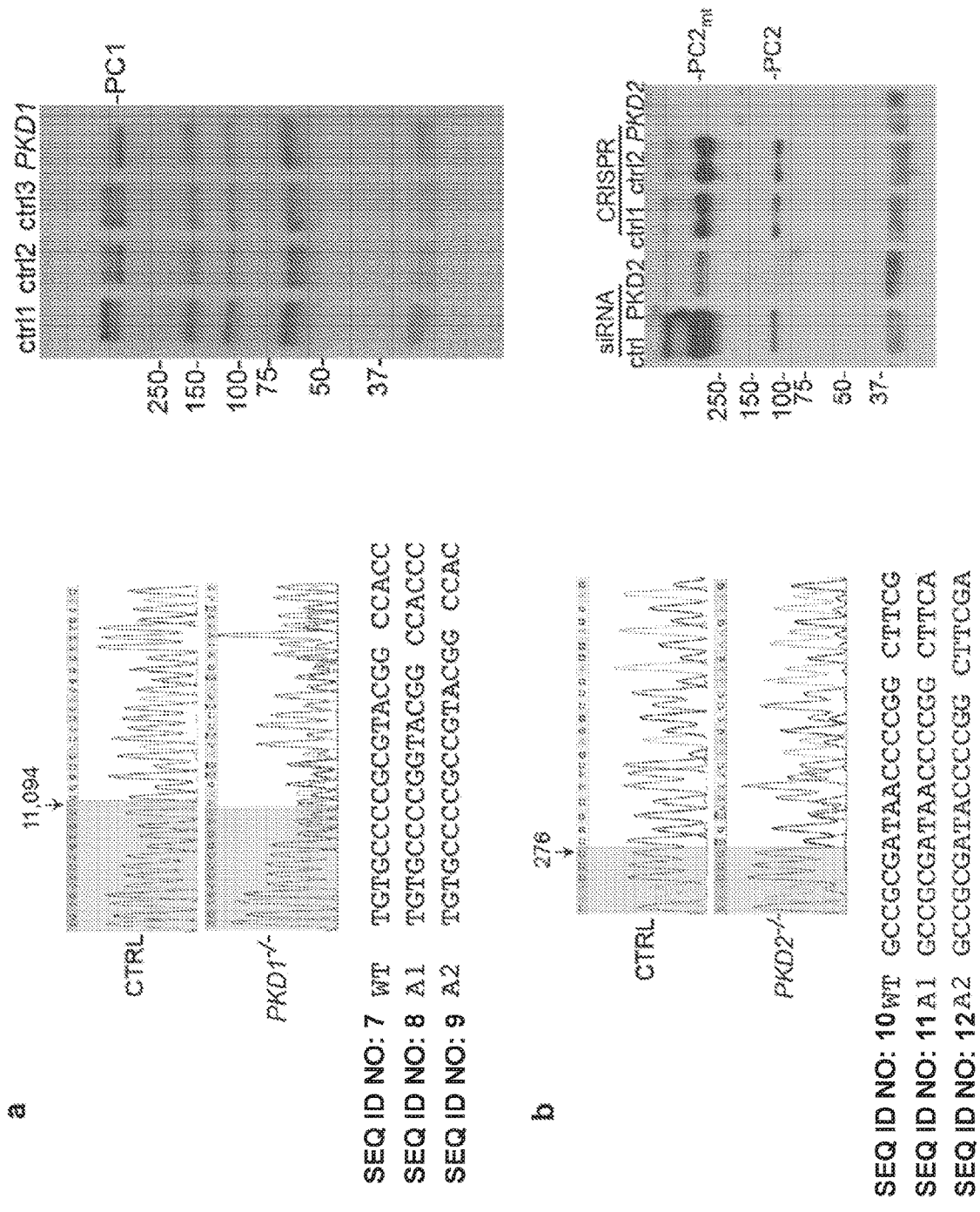

THREE-DIMENSIONAL DIFFERENTIATION OF EPIBLAST SPHEROIDS TO KIDNEY ORGANOIDS MODELS STAGE-SPECIFIC EPITHELIAL PHYSIOLOGY, MORPHOGENESIS, AND DISEASE

CROSS REFERENCE TO RELATED APPLICATIONS

This application is a 35 U.S.C. § 371 National Phase Entry Application of International Application No. PCT/US2016/050271, filed Sep. 2, 2016, which designates the U.S. and which claims benefit under 35 U.S.C. § 119(e) of U.S. Provisional Application No. 62/213,740, filed Sep. 3, 2015, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Feb. 28, 2018, is named 2016-09-02_SequenceListing_043214-085701-PCT.txt and is 2,600 bytes in size.

FIELD OF THE INVENTION

Human stem cells can be cultured in three-dimensional cultures recapitulate tissue-specific epithelial morphogenesis, physiology, and disease.

BACKGROUND

Both undifferentiated stem cells and terminally differentiated somatic cells form epithelia. These can function to establish axes for differentiation in the embryo, or to perform barrier and transport roles in adult organs such as the kidney. 3D cell culture in vitro is a powerful tool for investigating epithelial morphogenesis, physiology, and disease, being readily accessible to microscopic inspection, chemical treatment, and experimental manipulation. Studies of epithelial cell lines such as Madin-Darby Canine Kidney (MOCK) cells have, for instance, revealed polarity and apoptosis pathways contributing mechanistically to lumen formation. Conventional epithelial cell lines, however, are lineage-restricted and lack genetic diversity. As a result, the 3D structures that arise are relatively simple, and it has been challenging to perform controlled comparisons of different epithelia of the same genetic background, or the same epithelia with different genetic backgrounds. Despite these limitations, interest in the cellular microenvironment and 3D culture systems has been increasing steadily, particularly for stem cell applications. There is a significant need for genetically diverse cell culture platforms that accurately reconstitute tissue-specific epithelial function, particularly in humans where species-specific toxicology and disease pathophysiology is of significant biomedical relevance.

Human pluripotent stem cells (hPSCs) are capable of extensive self-renewal and can differentiate into all somatic cell types. They therefore represent a reproducible source of diverse human epithelia for laboratory studies and regeneration. hPSCs, including both embryo-derived embryonic stem cells (ESCs) and patient-derived induced pluripotent stem cells (iPSCs), are genetically diverse, with thousands of lines in production representing specific patient populations or gene-targeted knockout mutants. Undifferentiated hPSCs are polarized epithelial cells and are typically cultured either as flat colonies in adherent monolayer cultures or as dense aggregates in 3D suspensions. These epithelial cultures are proposed to model the implantation-stage epiblast epithelium. In contrast, mouse (m)ESCs adopt a compact, clustered morphology in culture that resembles the inner cell mass (ICM), a structure which precedes the epiblast developmentally.

Recently, mESCs surrounded by MATRIGEL™ extracellular matrix (ECM) were shown to form polarized rosettes with small cavities when, suggesting the possibility of modeling amniotic cavity formation in vitro. However, because those experiments were performed with mESCs cultured under conditions that do not sustain pluripotency, it remains unclear whether the observed rosettes represent ICM, epiblast, or differentiating subtypes, which can also form spheroids. Experiments in pluripotency-sustaining media using epiblast-stage hPSCs are required to address this question and establish a human model of epiblast cavitation.

Described herein is the discovery that hPSCs in three-dimensional cultures and their differentiated descendants can functionally recapitulate tissue-specific epithelial morphogenesis, physiology, and disease. Undifferentiated hPSCs form spheroid colonies surrounding hollow, amniotic-like cavities, modeling the embryonic epiblast. A two-step protocol differentiates spheroids into convoluted, tubular organoids with developmental and structural characteristics of kidney nephrons, including proximal tubules, podocytes and endothelial cells. Kidney tubules and epiblast cavities differentially accumulate fluorescent cargoes and respond to nephrotoxic chemical injury.

SUMMARY OF THE INVENTION

Described herein is a method of generating human organoids, including providing a quantity of human pluripotent stem cells (hPSCs), culturing the hPSCs in a culture medium to form epiblast spheroids, and differentiating the epiblast spheroids in a differentiation medium, wherein the differentiation medium includes one or or more agents capable of differentiating the epiblast spheroids into organoids. In various embodiments, the hPSCs are cultured in absence of leukemia inhibitory factor (LIF) and doxycycline prior to forming epiblast spheroids. In various embodiments, the hPSCs are cultured in the presence of Y27632 prior to forming epiblast spheroids. In various embodiments, the culture medium includes MATRIGEL™. In various embodiments, the culture medium includes collagen I. In various embodiments, culturing the hPSCs includes depositing a first layer of culture medium on a surface, placing the hPSCs on the deposited culture medium, and adding a second layer of culture medium over the hPSCs. In various embodiments, culturing the hPSCs in a culture medium includes about 1, 2 or more days. In various embodiments, the one or more agents include CHIR99021. In various embodiments, the one or more agents comprise B27. In various embodiments, differentiating the epiblast spheroids includes about 7, 8, 9, 10, 11, 12, or 13 or more days. In various embodiments, the epiblast spheroids express one or more of podocalyxin (PODXL), zonula occluden (ZO-1) and β-catenin. In various embodiments, the epiblast spheroids are cavitated. In various embodiments, the organoids are tubular. In various embodiments, the organoids are kidney organoids. In various embodiments, the organoids express one or more of podocalyxin (PODXL), zonula occluden (ZO-1), and lotus tetragonolobus lectin (LTL). For example, hPSCs can be maintained feeder-free on about 3% Reduced Growth Factor GelTrex for at least one passage in media such as mTeSR1, or a hESC conditioned media (CM)+leukemia inhibitory factor (LIF)+dox for hLR5 iPSCs). In various embodiments, hPSCs are primed by withdrawing LIF and doxycycline. In various embodiments, withdrawal of LIF and doxycycline includes substitution with FGF2. In various embodiments, cells are plated a specific density relative to the culture surface and media volume.

Also described herein is quantity of organoids made by a method of generating human organoids, including providing a quantity of human pluripotent stem cells (hPSCs), culturing the hPSCs in a culture medium to form epiblast spheroids, and differentiating the epiblast spheroids in a differentiation medium, wherein the differentiation medium includes one or or more agents capable of differentiating the epiblast spheroids into organoids. In various embodiments, the hPSCs are cultured in absence of leukemia inhibitory factor (LIF) and doxycycline prior to forming epiblast spheroids. In various embodiments, the hPSCs are cultured in the presence of Y27632 prior to forming epiblast spheroids. In various embodiments, the culture medium includes MATRIGEL™. In various embodiments, the culture medium includes collagen I. In various embodiments, culturing the hPSCs includes depositing a first layer of culture medium on a surface, placing the hPSCs on the deposited culture medium, and adding a second layer of culture medium over the hPSCs. In various embodiments, culturing the hPSCs in a culture medium includes about 1, 2 or more days. In various embodiments, the one or more agents include CHIR99021. In various embodiments, the one or more agents comprise B27. In various embodiments, differentiating the epiblast spheroids includes about 7, 8, 9, 10, 11, 12, or 13 or more days. In various embodiments, the epiblast spheroids express one or more of podocalyxin (PODXL), zonula occluden (ZO-1) and β-catenin. In various embodiments, the epiblast spheroids are cavitated. In various embodiments, the organoids are tubular. In various embodiments, the organoids are kidney organoids. In various embodiments, the organoids express one or more of podocalyxin (PODXL), zonula occluden (ZO-1), and lotus tetragonolobus lectin (LTL). In various embodiments, the hPSCs are genetically modified using genomic editing, such as CRISPR.

Further described herein is a method of generating tubular organoids, including providing a quantity of epiblast spheroid and differentiating the epiblast spheroids in a differentiation medium, wherein the differentiation medium includes one or or more agents capable of differentiating the epiblast spheroids into organoids. In various embodiments, the one or more agents comprise CHIR99021. In various embodiments, the one or more agents comprise B27. In various embodiments, differentiating the epiblast spheroids includes about 7, 8, 9, 10, 11, 12, or 13 or more days. In various embodiments, the tubular organoids are kidney organoids. In various embodiments, the kidney organoids express one or more of podocalyxin (PODXL), zonula occluden (ZO-1), and lotus tetragonolobus lectin (LTL). In various embodiments, differentiating the epiblast spheroids into kidney organoids includes further culturing in a second differentiation medium including RPMI and B27. In various embodiments, differentiating the epiblast spheroids into kidney organoids includes further culturing in a second differentiation medium including CHIR99021, RPMI and B27 for about 24 hours, replacement of the second differentiation medium with a third differentiation medium including CHIR99021, RPMI, B27 and insulin and additional culturing for about 48 hours, addition of IWP2 and continued culturing for about 48 hours, and additional replacement of the third differentiation medium with the second differentiation medium.

Also described herein is a method of screening a compound for an effect on tubular organoids, including providing a quantity of tubular organoids, adding one or more compounds to the tubular organoids, determining changes to phenotype or activity of the tubular organoids, and correlating the changes with an effect of the compounds on tubular organoids, thereby screening the one or more compounds for an effect on tubular organoids.

In various embodiments, determining changes to phenotype or activity includes detecting one or more markers in the tubular organoids. In various embodiments, the one or more markers comprise kidney injury molecule (KIM-1). In various embodiments, an increase in KIM-1 expression correlates with a toxic effect of the compound. In various embodiments, the tubular organoids are kidney organoids.

BRIEF DESCRIPTION OF FIGURES

FIG. 3. Tubular organoids recapitulate kidney development and architecture. (a) Quantification of cardiomyocyte protocol applied to 2D and 3D cultures (n=3). (b) Whole 24 well on day 19 of tubular differentiation, with zoom of boxed regions. (c-d) Confocal immunofluorescence for nephron progenitor markers (SIX2, LHX1, PAX2) and proximal tubule markers (L TL, LRP2/megalin, CUBN) in tubular organoids. Zoom shows white boxed area. (e) Electron micrographs of two representative tubules, with progressive magnifications of regions in colored boxes highlighting apical microvilli (arrowheads) and tight junctions (arrows). (f) Wide-field images showing localization of LTL+ and PODXL with E-cadherin (ECAD, top, high magnification) and CD31 (bottom, low magnification). (g) Confocal optical section showing co-localization of SYNPO and CD31 clusters within tubular organoids (arrowheads). (h) Widefield immunofluorescence showing colocalization of nuclear WT1 with SYNPO, and (i) CD31 with vWF in tubular organoids. Scale bars, 10 μm (e) or 100 μm. Error bars, s.e.m.

Figure 4:
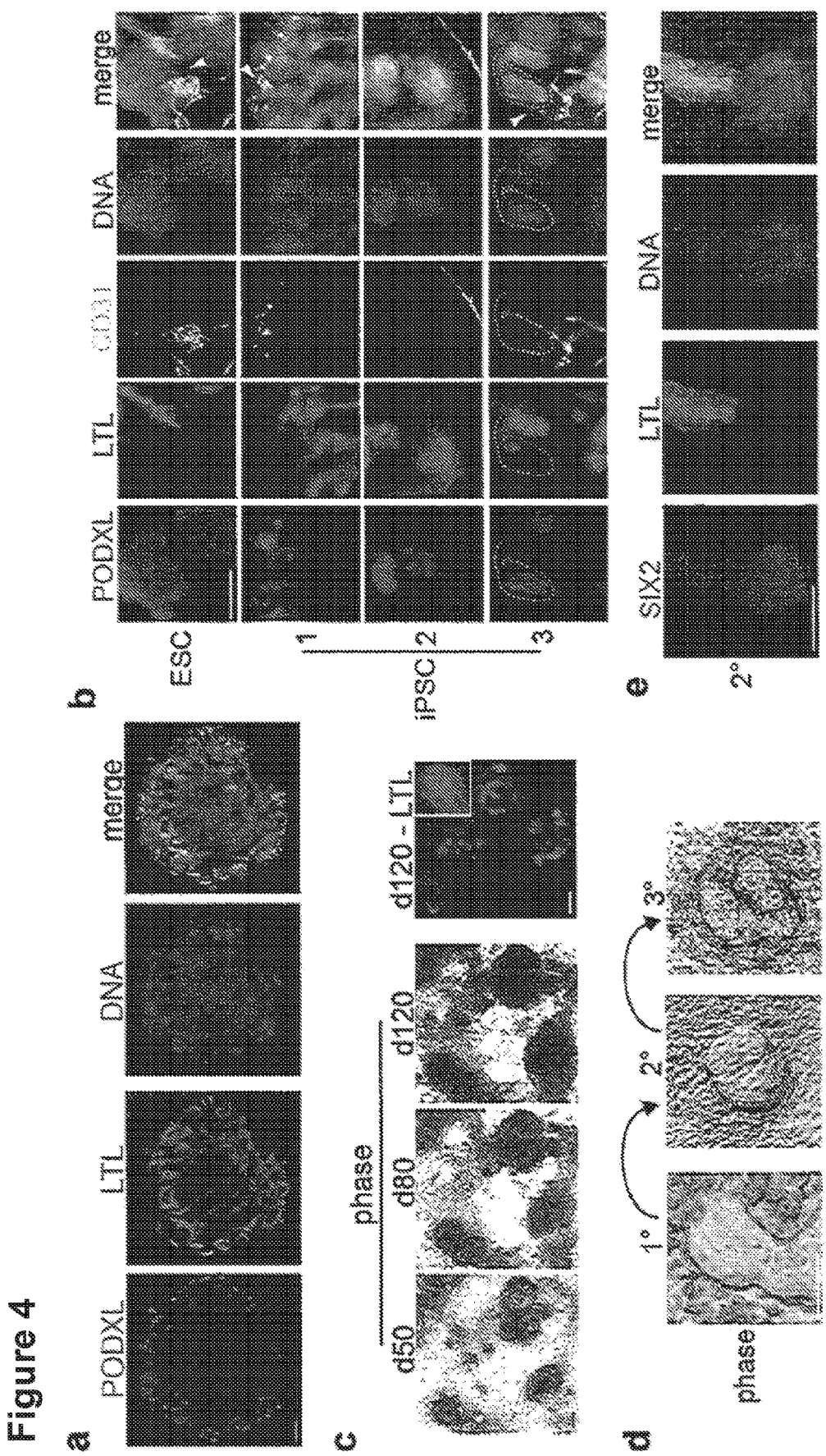
Figure 4:
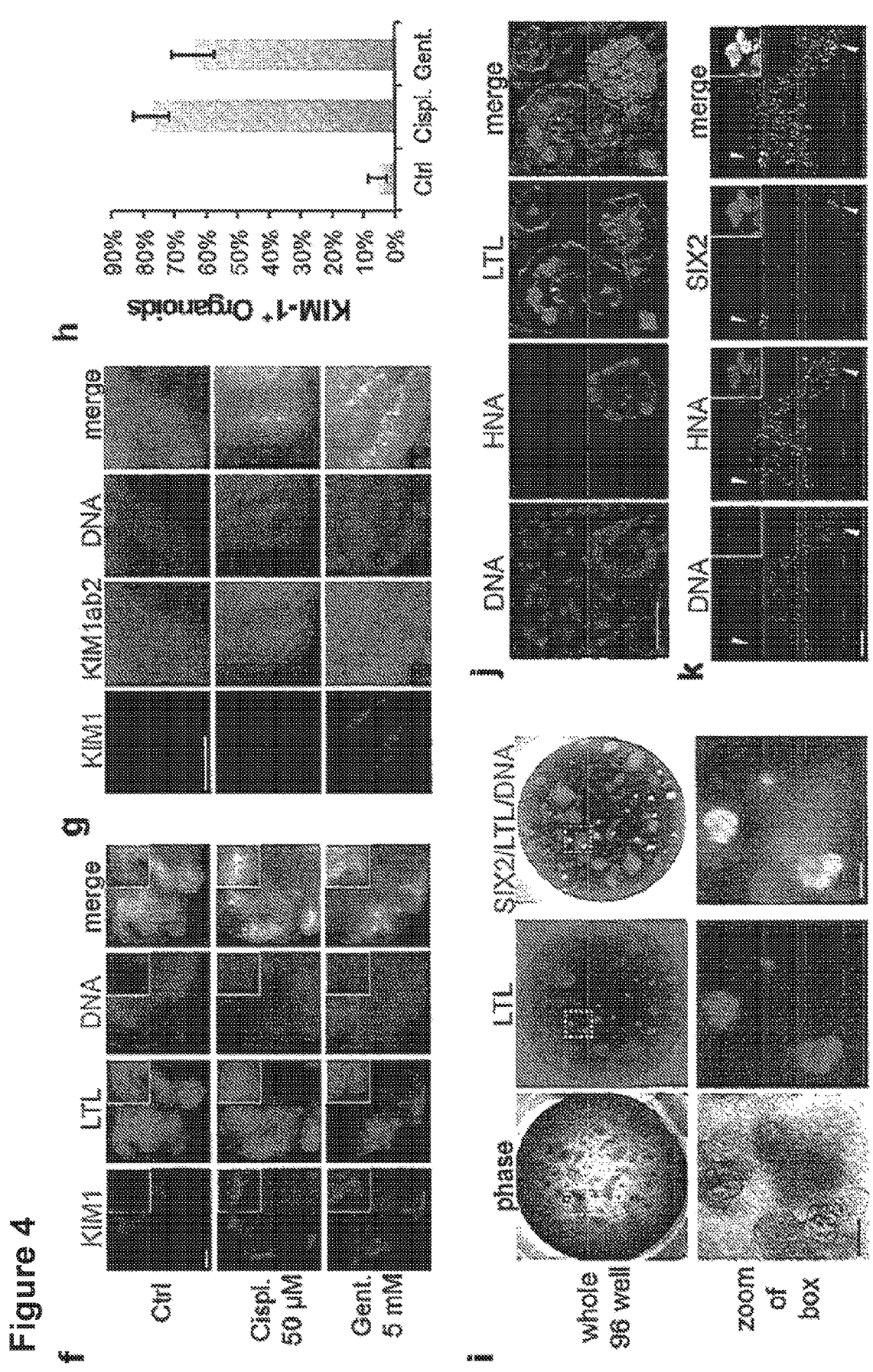

FIG. 4. Tubular organoids survive long term and model kidney physiology. (a) Large kidney organoid with kidney-like patterning derived from hiPSCs. (b) Organoids derived from hESCs or hiPSCs reprogrammed from three different patients, showing interactions between tubular, podocyte-like, and endothelial compartments (white arrowheads). White dashed outline highlights a representative tubular terminus. (c) Phase contrast time course and LTL immunofluorescence in tubules after 120 days of culture (d120). (d) Phase contrast images of primary (1°) tubules and daughter tubules (2° and 3°) arising after dissociation and serial passaging (arrows). (e) SIX2 and L TL immunofluorescence in 2° tubules. (f) Co-localization of KIM-1 with LTL or (g) a second KIM-1 antibody (KIM1 ab2). (h) Quantification of organoids expressing KIM-1 after treatment with nephrotoxic chemicals (n=3). (i) Whole well of a 96-well plate showing kidney organoids. (j) Confocal images of organoid-derived growths (HNN) expressing L TL or (k) SIX2 progenitors (arrowheads) after three weeks of growth in developing mouse kidneys. Scale bars, 100 μm or 50 μm (d-e, g). Error bars, s.e.m.

Figure 5:
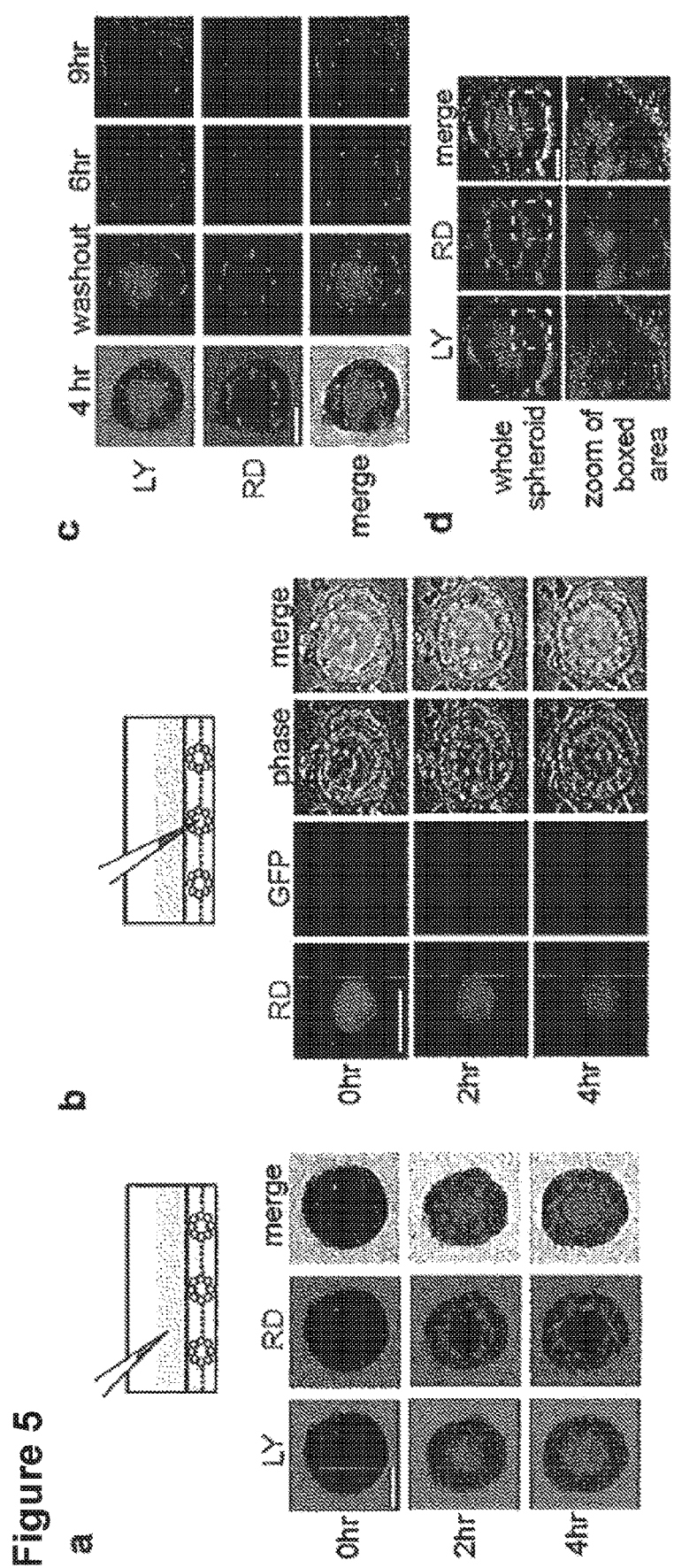
Figure 5:
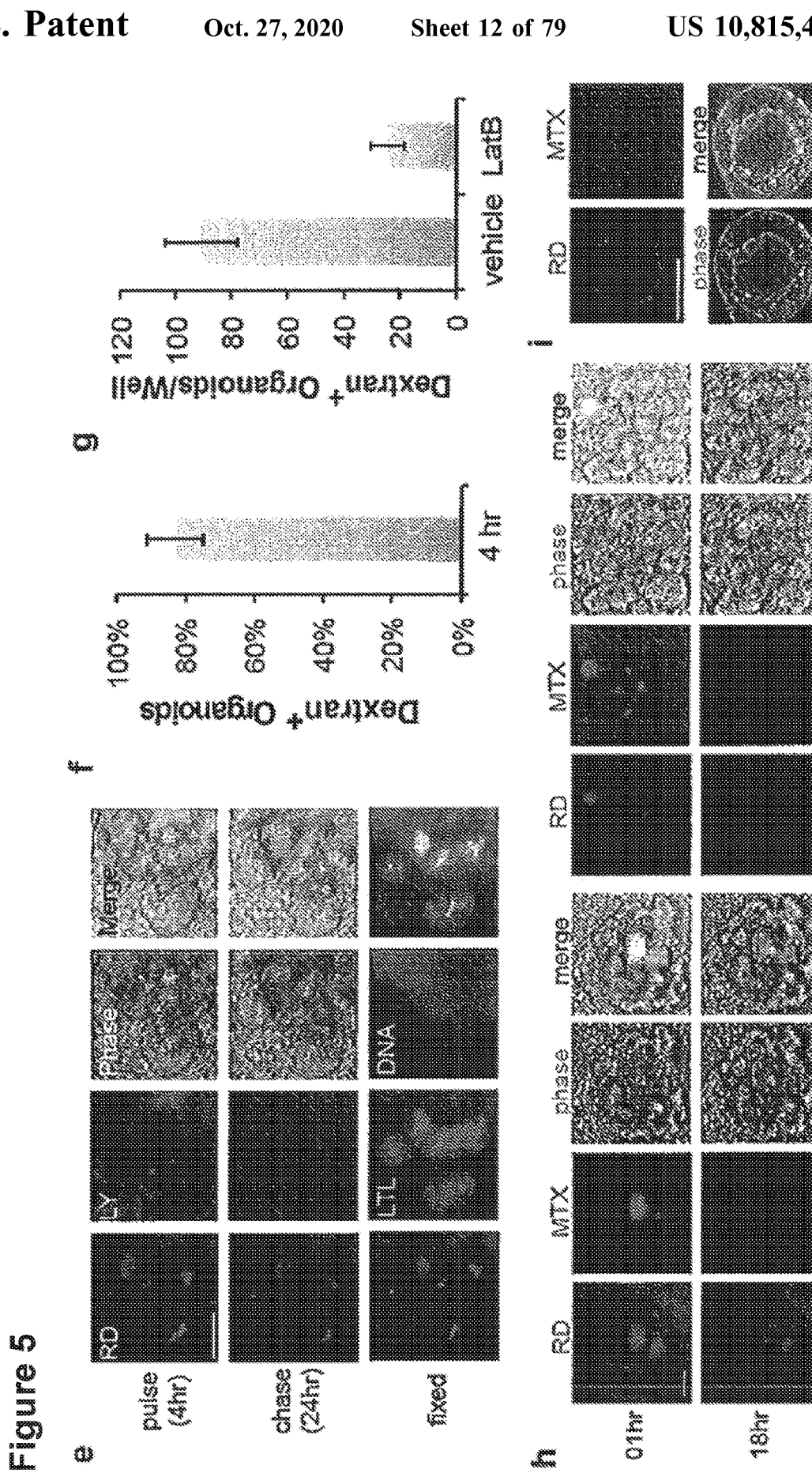

FIG. 5. Differential accumulation of fluorescent cargoes in epiblast spheroids versus kidney tubules. (a) Experimental schematic and confocal time-lapse images showing hPSC spheroids incubated with L Y and RD. (b) Experimental schematic and wide-field time course of an hPSC spheroid cavity after microinjection with RD. No autofluorescence is detected (GFP channel). (c) Time course of hPSCs incubated with molecular dyes for four hours, after which the media was changed (washout). (d) Cavity lining cells imaged immediately after washout. Lower panel shows zoom of boxed region. (e) Representative time course of a tubular organoid incubated with RD and L Y followed by washout (pulse), incubation (chase), fixation, and co-localization with L TL. (f-g) Quantification of tubular organoids that accumulated RD, with or without 2 μM LatB (n=3). (h) Fluorescein-MTX and RD distributions in two representative live organoids 1 hour and 18 hours after washout or (i) an hPSC spheroid immediately after washout. Scale bars, 50 μm (a-d) or 100 μm (e-i). Error bars, s.e.m.

Figure 6:
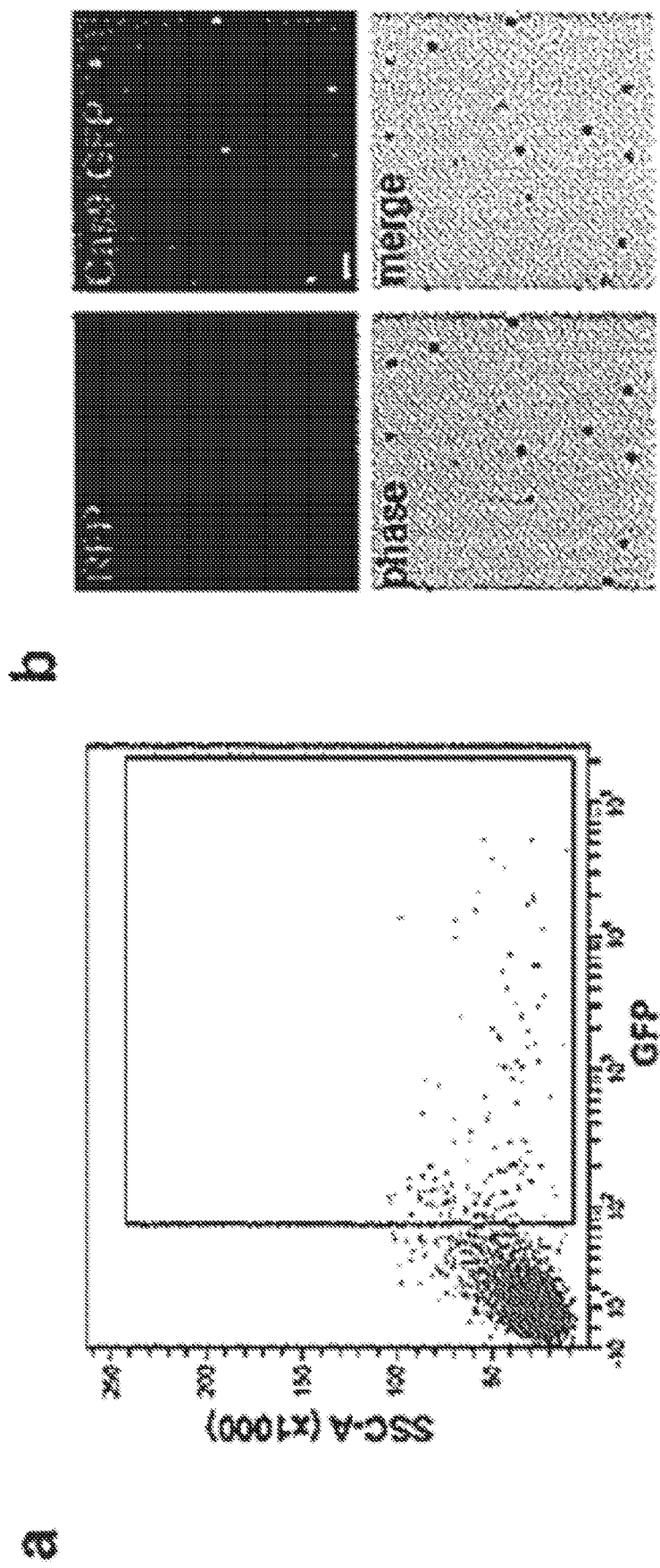
Figure 6:
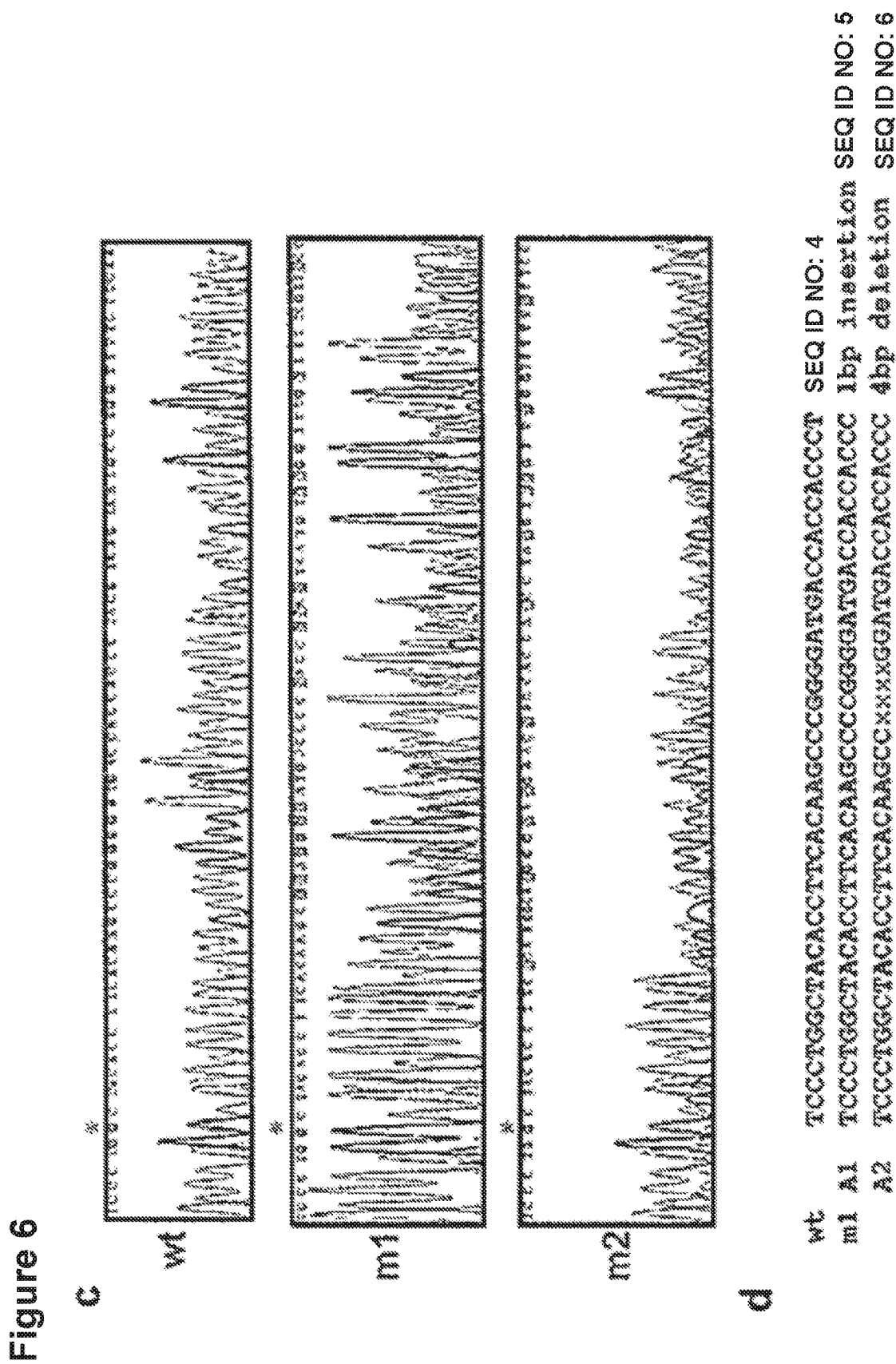
Figure 6:
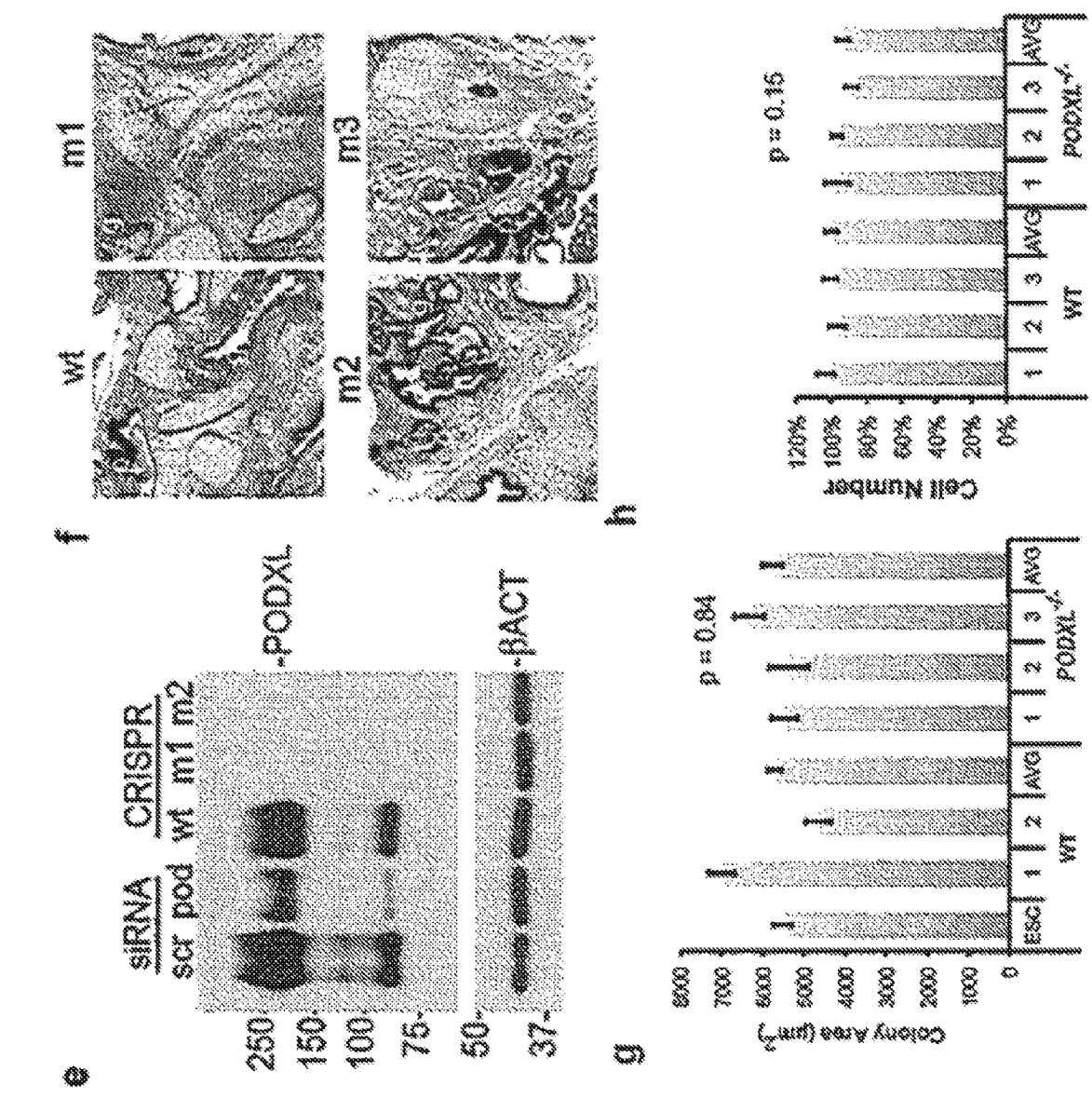
Figure 6:
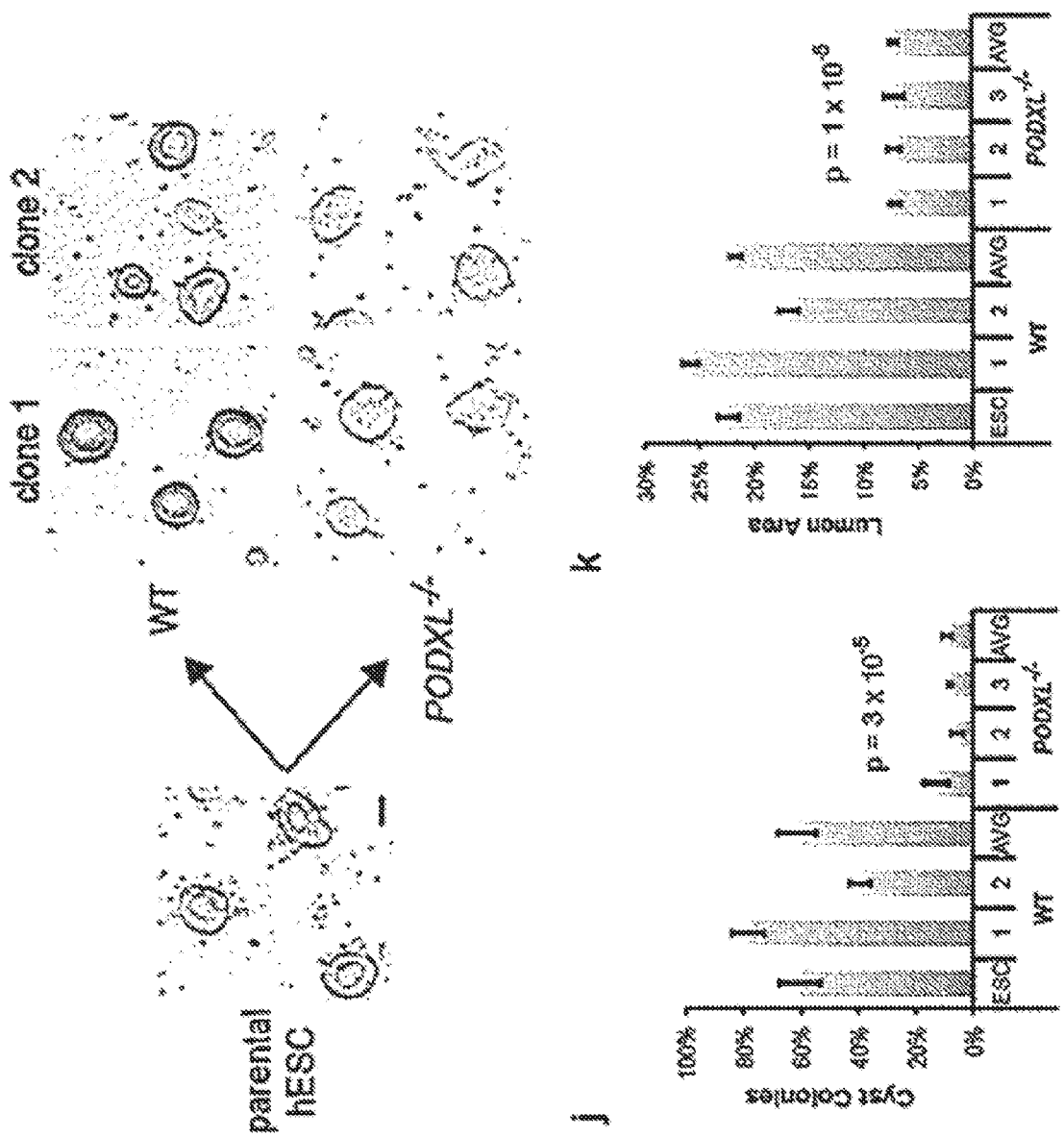
Figure 6:
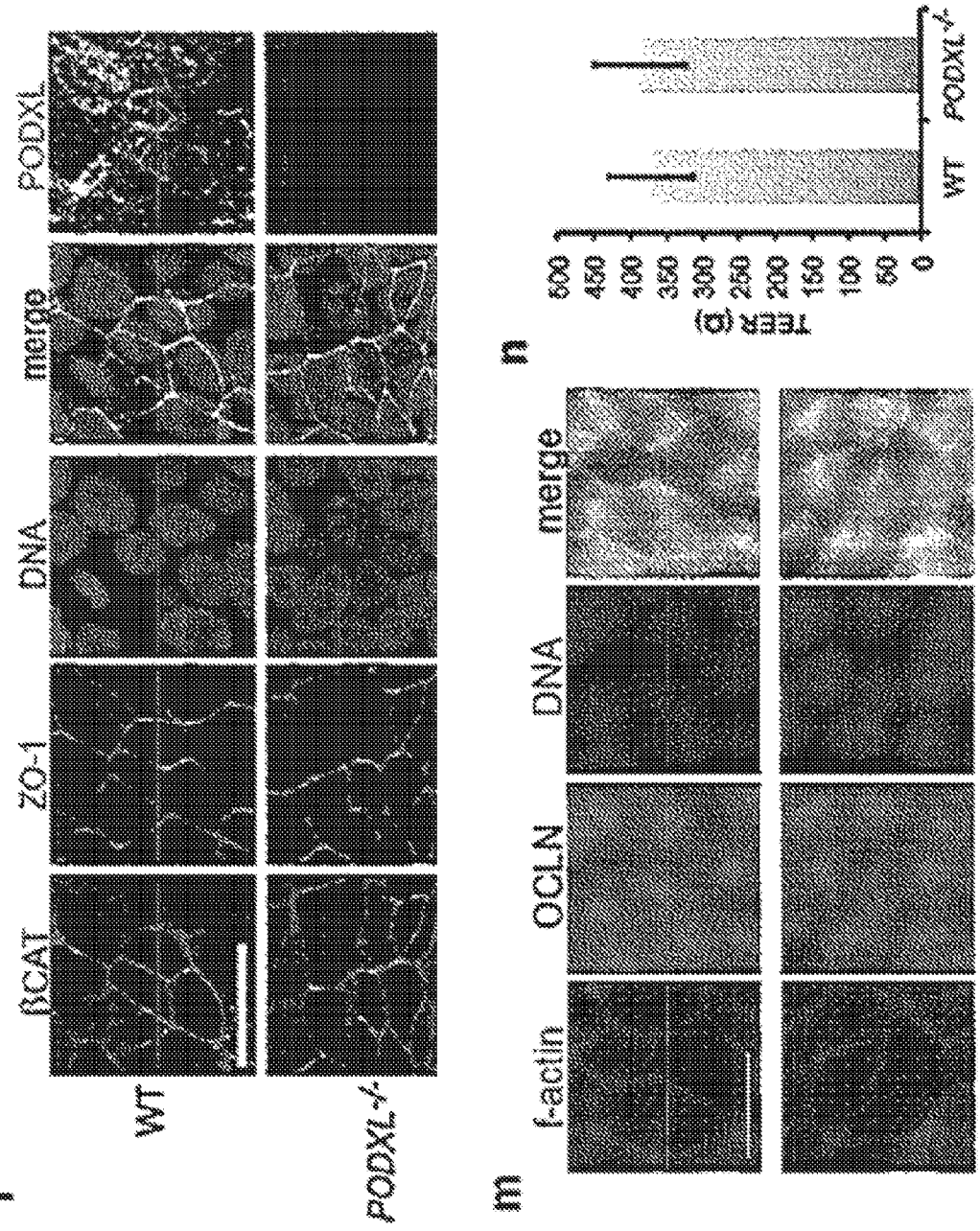

FIG. 6. Podocalyxin promotes lumenogenesis in epiblast spheroids. (a) Representative FACS plot of H9 ESCs transfected with pCas9-GFP and PODXL gRNA plasmid. Boxed region with purple events were plated for clonal expansion. (b) Fluorescence micrographs one day after flow sorting. (c) Aligned chromatograms of a CRISPR/Cas9 clone which sequenced as wild-type (wt) and two distinct podocalyxin mutants (m1 and m2). Pink asterisk marks the beginning of the gRNA sequence. (d) Interpreted chromatogram for mutant m1, showing separated alleles (A1 and A2) aligned against the wild-type sequence. (e) immunoblot for podocalyxin protein in representative PODXL$^{-/-}$ hPSC mutants (m1 and m2), compared to CRISPR/Cas9 non-mutant clones (wt) or cells subjected to scrambled (scr) or podocalyxin (pod) siRNA knockdown. (f) Teratomas from wild-type or PODXL-/——hPSCs showing ectodermal pigmented epithelium (p), mesodermal cartilage (c), and endodermal gut-like epithelium (g). (g) Total area per epiblast spheroid colony (AVG pooled from ≥7 experiments/SO colonies). (h) Dissociated cell number after ~7 days growth in escapee 0/VT) and PODXL-/- hPSCs in 2D culture (AVG pooled from ≥14 experiments). Each experiment was normalized to the wild-type. (i) Brightfield images of sandwiched parental ESCs compared to mutant or WT CRISPR/Cas9 clones. (j) Cavitated spheroids as a percentage of total colonies. Data from WT or mutant cell lines were pooled to determine group means (AVG, n≥9) and p values. (k) Lumen area as a percentage of total area in colonies with cavities (AVG pooled from ≥9 experiments/40 colonies). (I) Confocal z-sections of undifferentiated hPSCs showing localization of ZO-1 and P-catenin in unmodified 0/VT) or PODXL-/- colonies. (m) actin and occludin (OCLN) immunofluorescence in two undifferentiated WT or PODXL-/- clones. (n) Averaged TEER measurements in WT or PODXL-/-—monolayers (n≥3). Scale bars, 50 μm or (1-m) 20 μm. Error bars, s.e.m.

Figure 7:
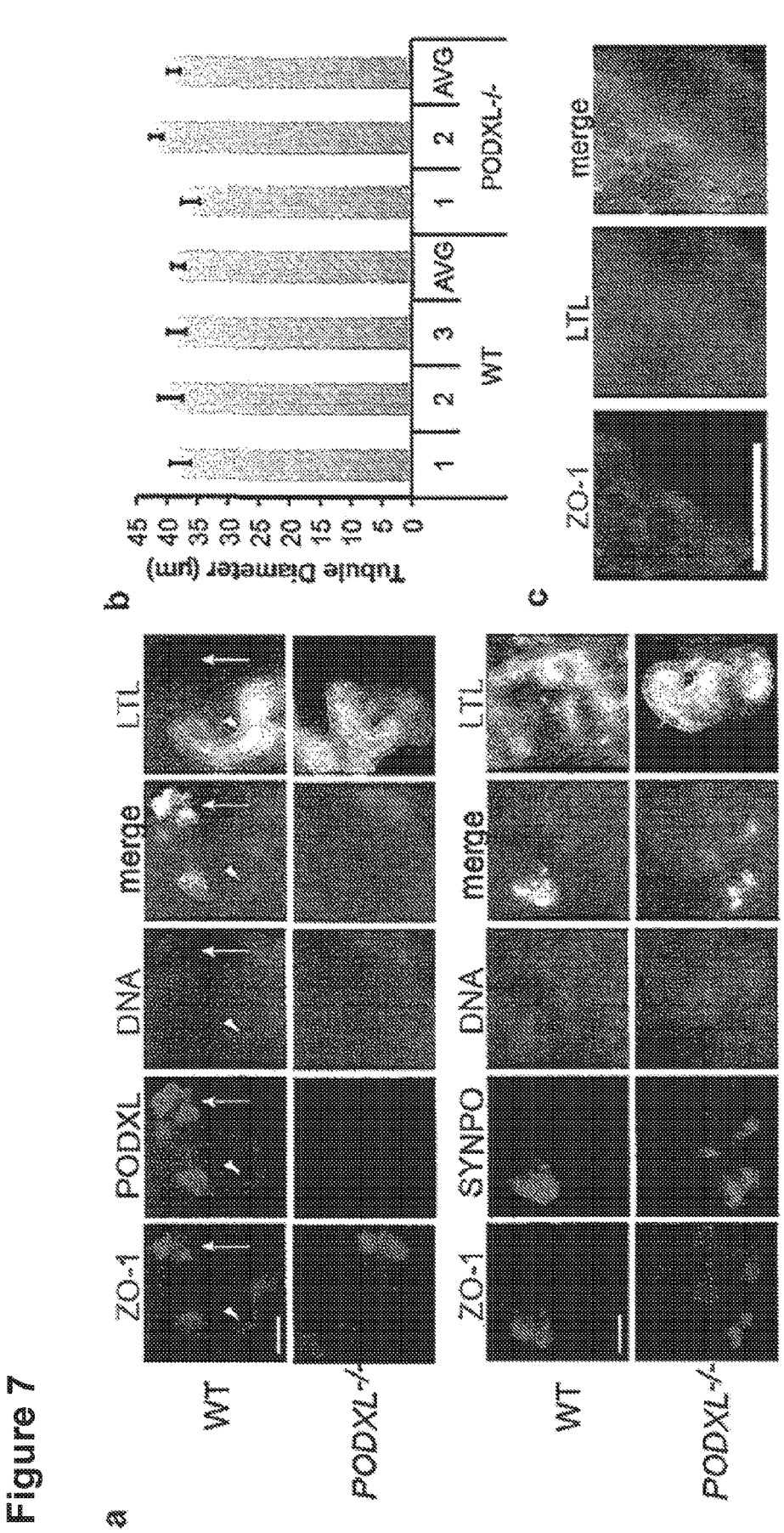
Figure 7:
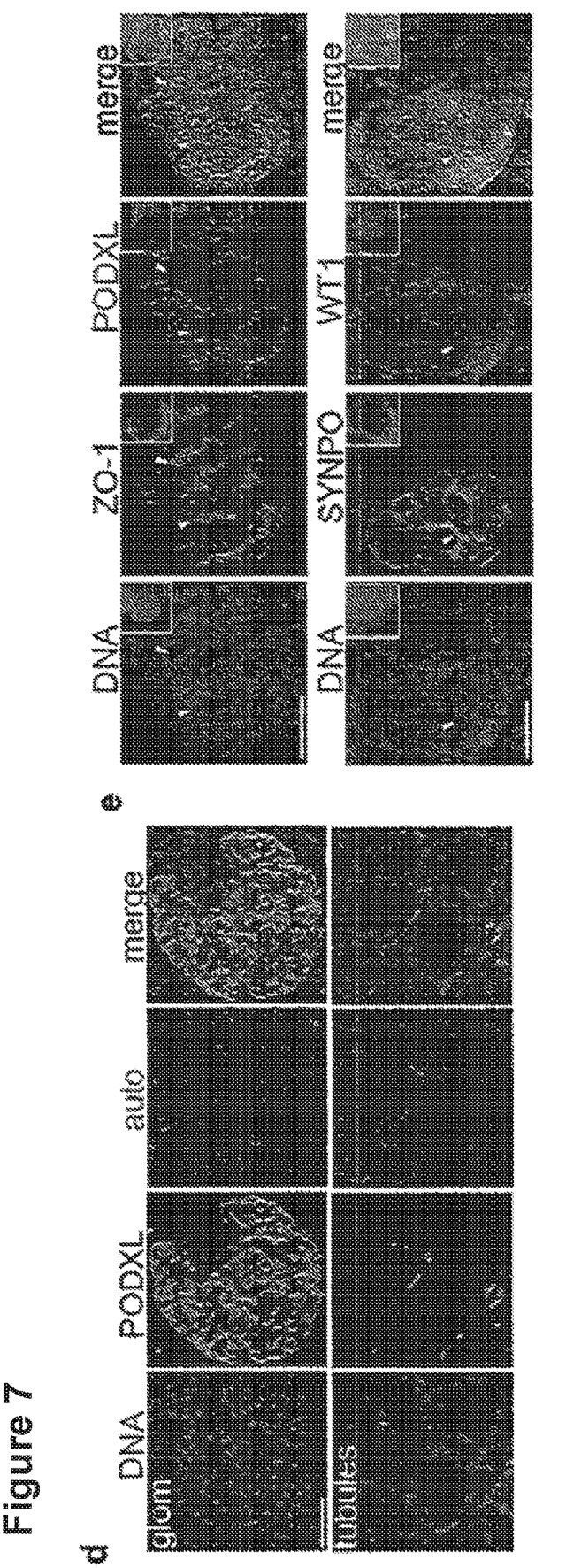
Figure 7:
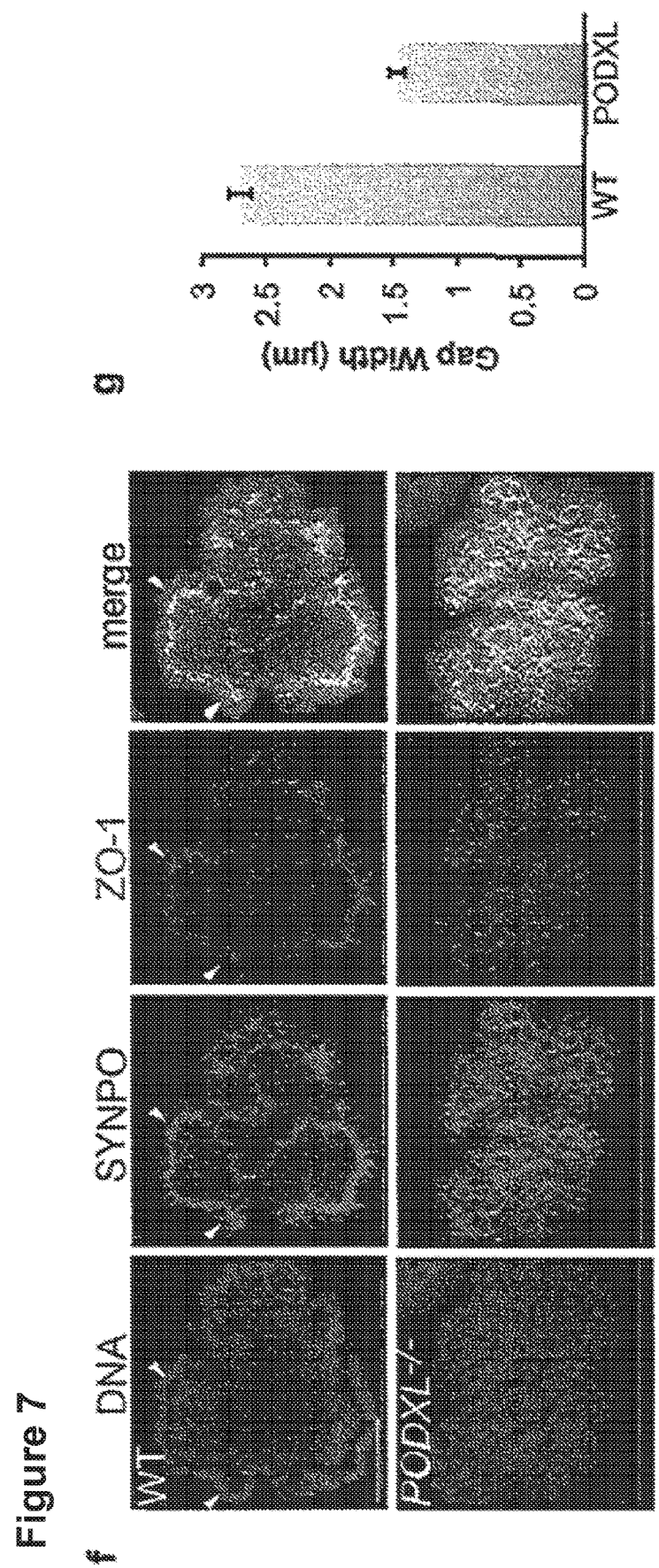

FIG. 7. Junctional complexes are disrupted in hPSC-derived PODXL$^{-/-}$ podocytes. (a) Immunofluorescence for tight junctions (ZO-1), proximal tubules (LTL), and podocytes (PODXL, SYNPO) in tubular organoids derived from PODXL$^{-/-}$—hPSCs or isogenic unmodified controls. In controls, podocalyxin is expressed strongly in podocytes (arrows) and faintly in tubules (arrowhead). (b) Tubule diameters in wild-type and PODXL$^{-/-}$ hPSCs (AVG pooled from ≥4 experiments/25 tubules). (c) Normal (cobblestone) ZO-1 immunofluorescence in a representative PODXL$^{-/-}$ kidney tubule. (d) Confocal optical section of adult human kidney. Podocalyxin is expressed in podocytes and peritubular capillaries, but is absent from tubules (arrowheads). (e) Confocal optical sections showing distributions of ZO-1 with podocalyxin, or SYNPO with WT1, in hPSC-derived podocyte clusters. Arrowheads highlight tracks of junctional complexes between podocytes. (f) Confocal sections of wild-type or PODXL$^{-/-}$ hPSC-podocyte clusters in tubular organoids. (g) Gap widths of tracks between adjacent podocyte nuclei in these cells (n≥100 gaps pooled from two experiments). Scale bars, 50 μm or (c) 20 μm. Error bars, s.e.m.

Figure 8:
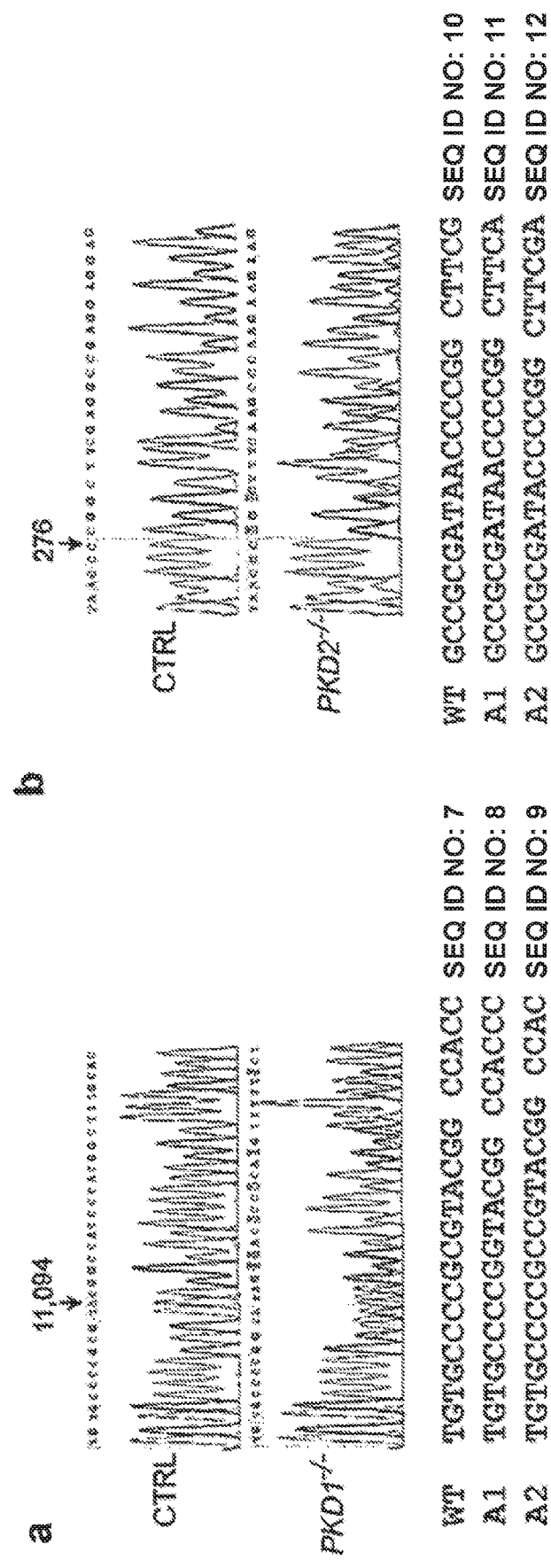
Figure 8:
Figure 8:
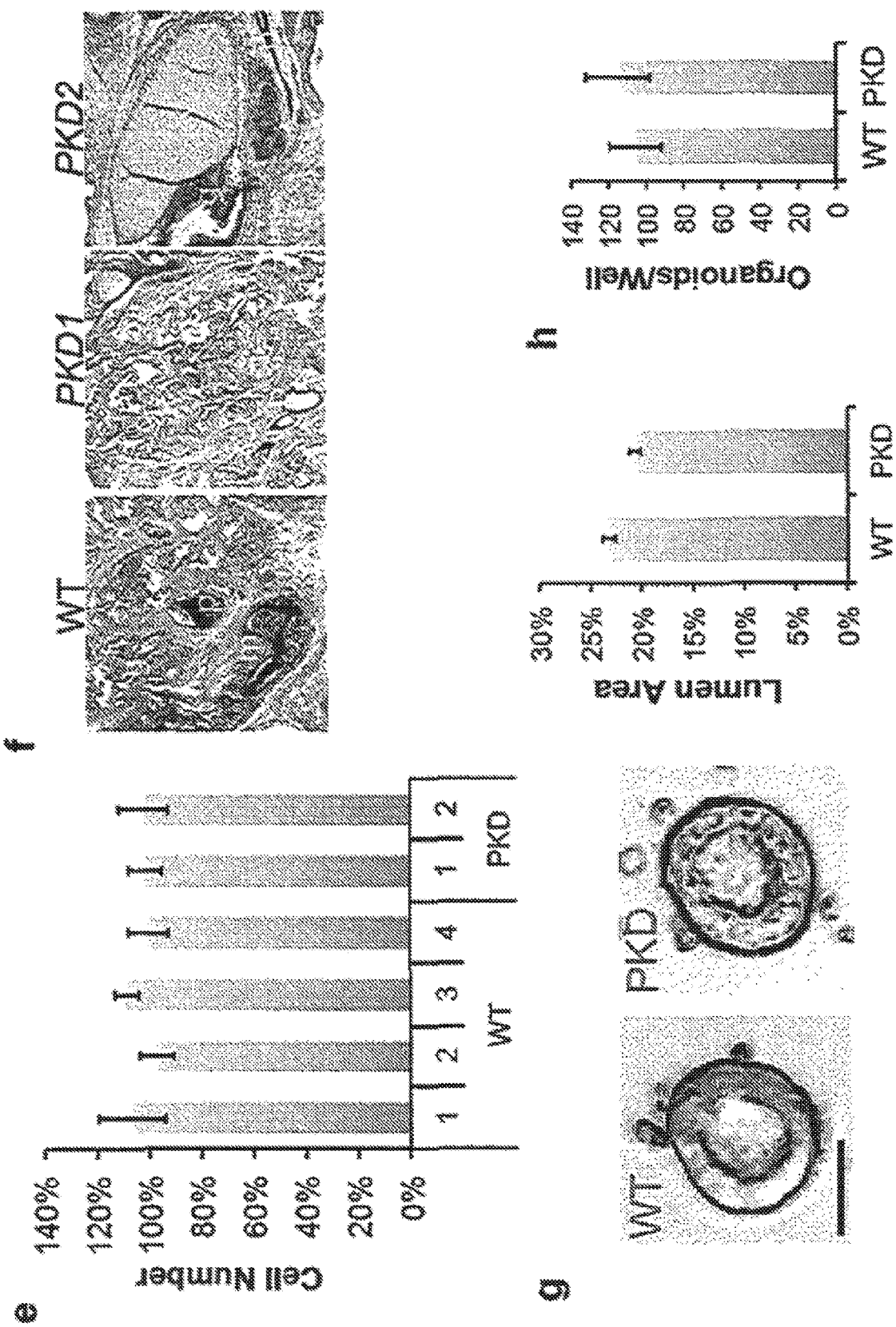

FIG. 8. PKD$^{-/-}$ and PKD$^{-/-}$ are dispensable for pluripotency and epiblast spheroid morphogenesis. (a and b) Chromatograms of control (CTRL) and PKD hPSCs. Shading marks 3' end of gRNA. Arrow indicates base pair number in the coding sequence. (b) PKD2 knockdown is shown for comparison. (c-d) lmmunoblots showing reduction in full-length PC1 or PC2 in PKD hPSCs, compared to isogenic controls. (e) Cell number in passages of WT and PKD hPSCs. (f) Teratomas showing ectodermal pigmented epithelium (p), mesodermal cartilage (c), and endodermal gut-like epithelium (g). (g) Epiblast spheroid morphology and quantification of proportional lumen area relative to whole spheroid (n≥90 spheroids, pooled from ≥5 experiments), and (h) organoid differentiation efficiency in WT and PKD hPSCs. p<0.01.

Figure 9:
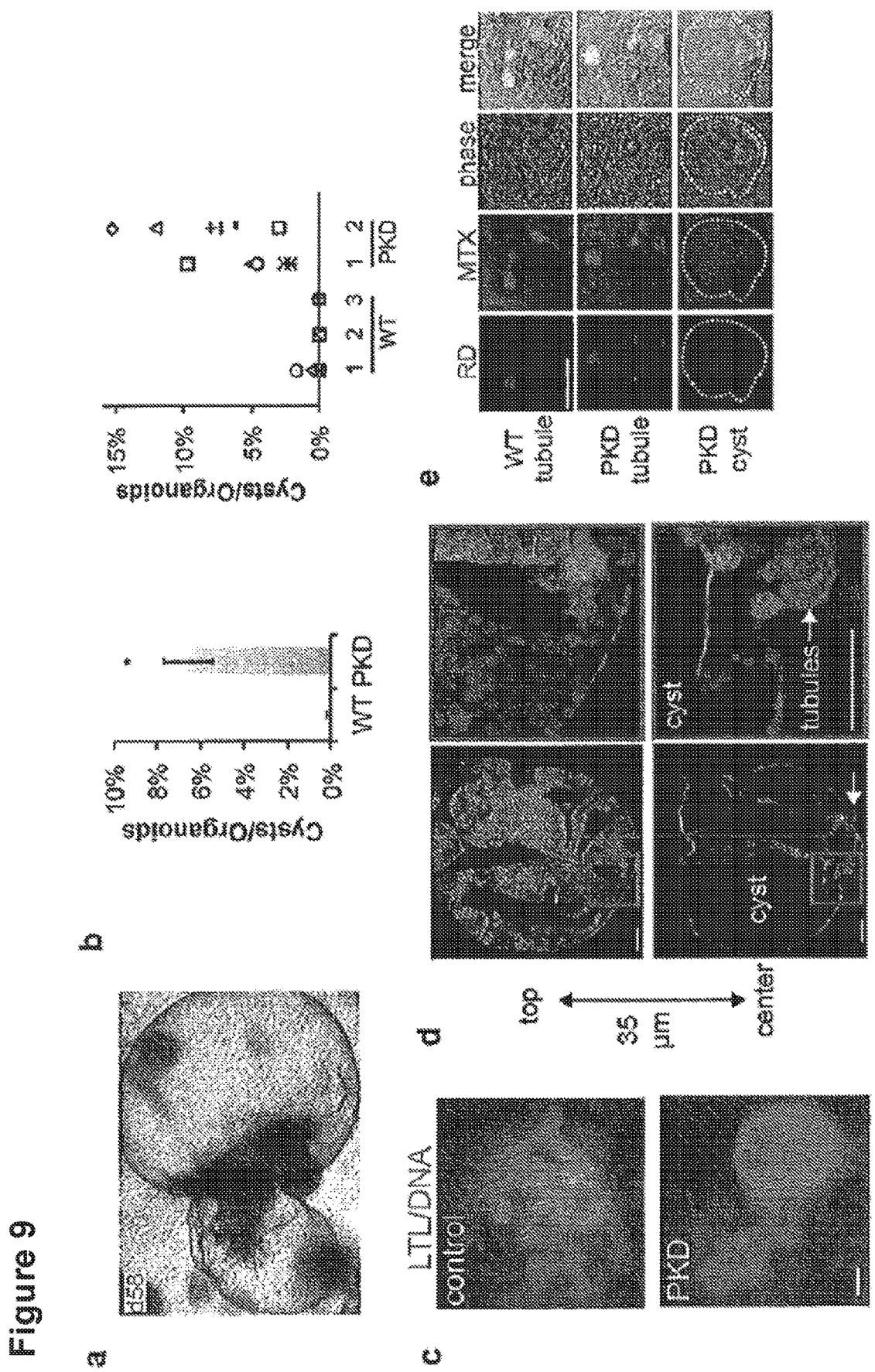

FIG. 9. PKD hPSCs model lineage-specific cyst formation. (a) Representative PKD cyst on day 58 of culture. (b) Quantification of cyst number per 24-well as averages (n>10 experiments) or scatter plots in PKD knockout organoids and isogenic WT controls. (c) Wide-field epifluorescence images and (d) confocal optical sections showing L TL reactivity in cysts. Representative z-sections show hollow center of cyst and associated tubular organoid (arrow). Zoom is shown of red boxed regions. (e) Accumulation of RD and MTX in WT and PKD lines. Dashed line outlines a PKD cyst. Scale bars, 100 µm. Errors, s.e.m. *, $p<0.01$.

Figure 10:
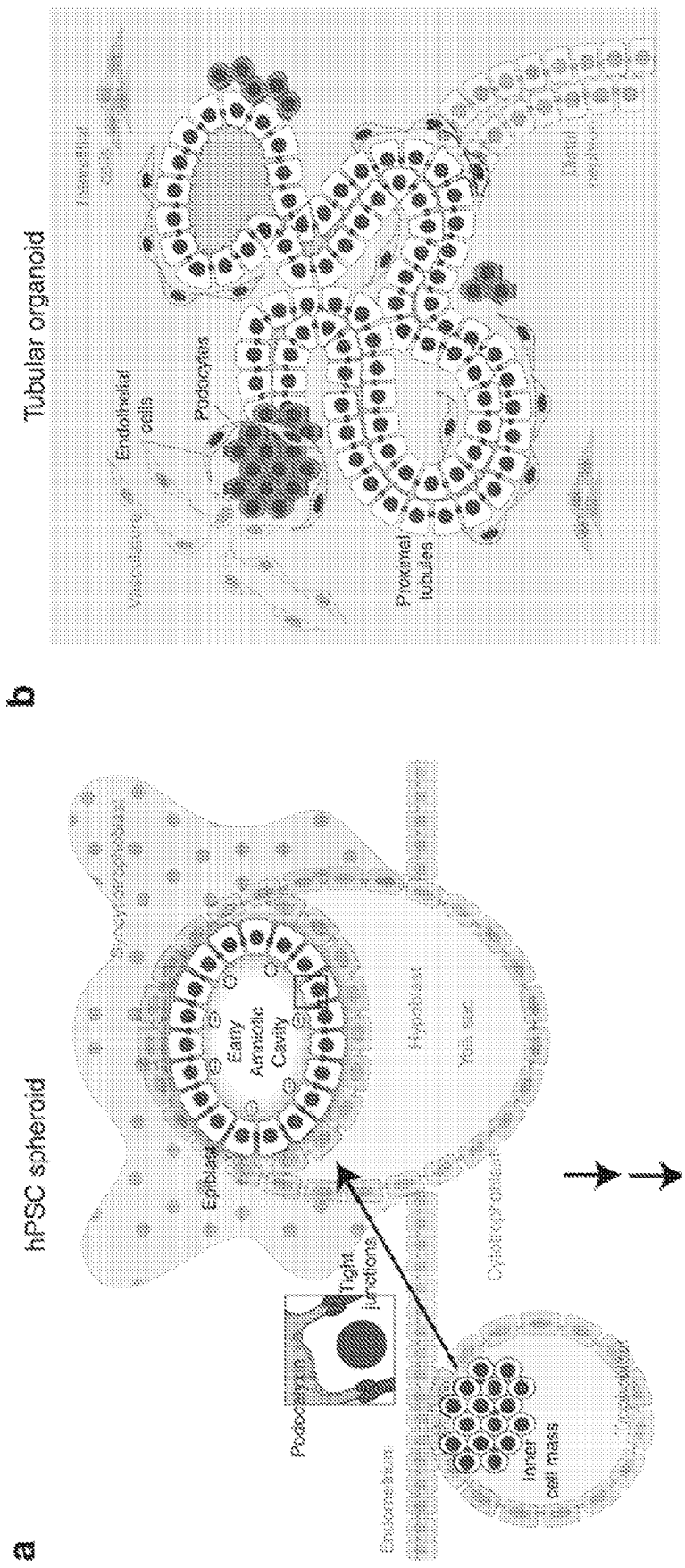

FIG. 10. Models of hPSC-derived epithelia. (a) Model of hPSC lumenogenesis. ICM-stage hPSCs lack polarized tight junctions, resulting in randomized aggregate formation. Epiblast-stage hPSCs are polarized with continuous tight junctions, and thus organize into a single-cell epithelium. In 3D growth, polarized accumulation of podocalyxin at the apical membrane results in charge repulsion (negative charges), promoting separation of the cells to form a lumen. Tight junctions segregate the apical membrane from environmental components, permitting the entry of small (green) molecules but excluding macromolecules (red), which accumulate in intercellular spaces. (b) Architecture of a proximal tubule within a kidney-like organoid. An elongated proximal tubule forms a simple columnar epithelium which binds L TL (green) on the apical surface. Surrounding podocyte-like cells express high levels of podocalyxin and form a less organized, aggregate structure at tubular termini. ZO-1 is expressed at a sub-apical position, restricted by podocalyxin. Endothelial cells interact closely with both tubular and podocyte-like compartments. Faded background structures place epithelial structures formed in vitro into their proposed context in vivo.

Figure 11:
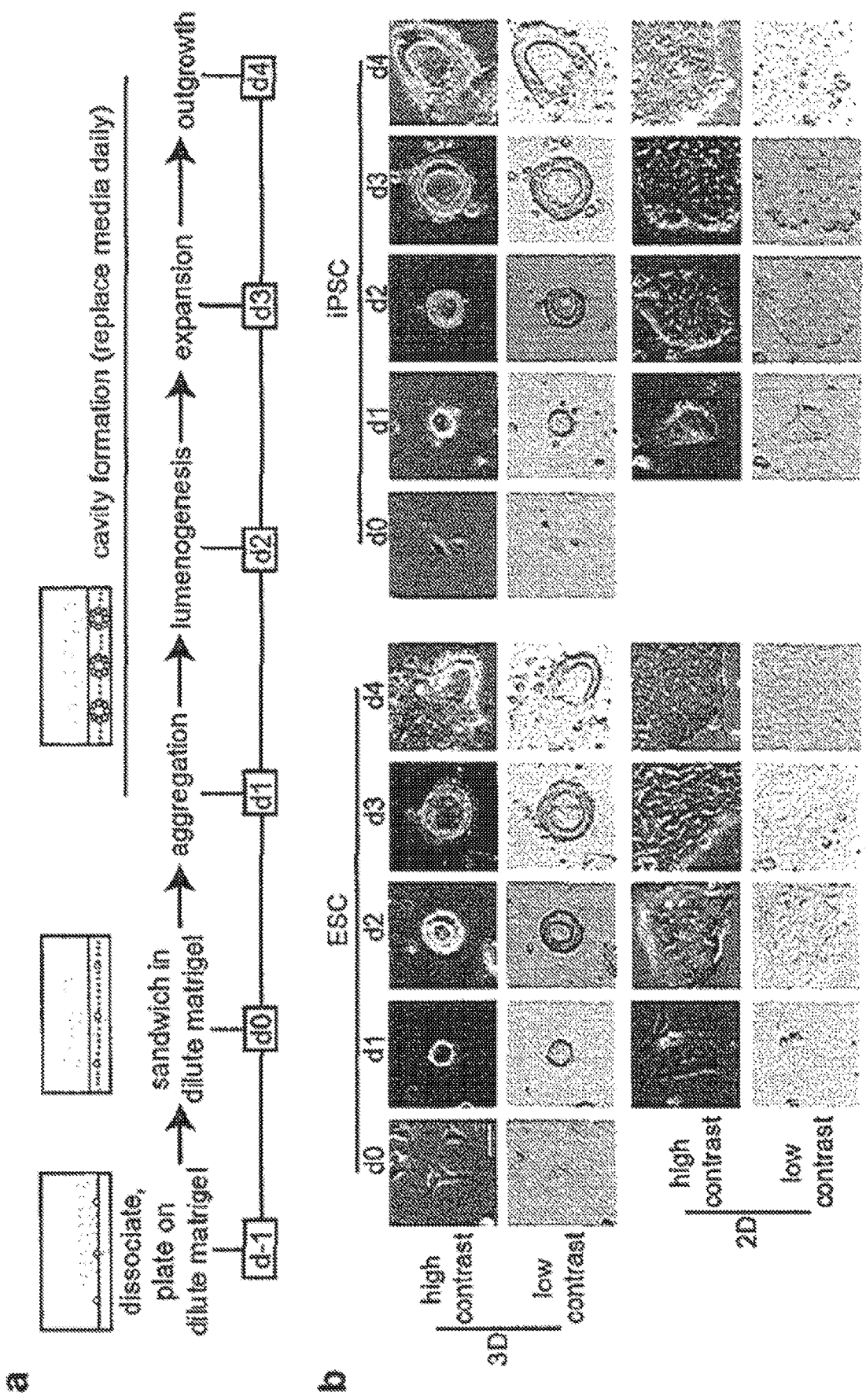
Figure 11:
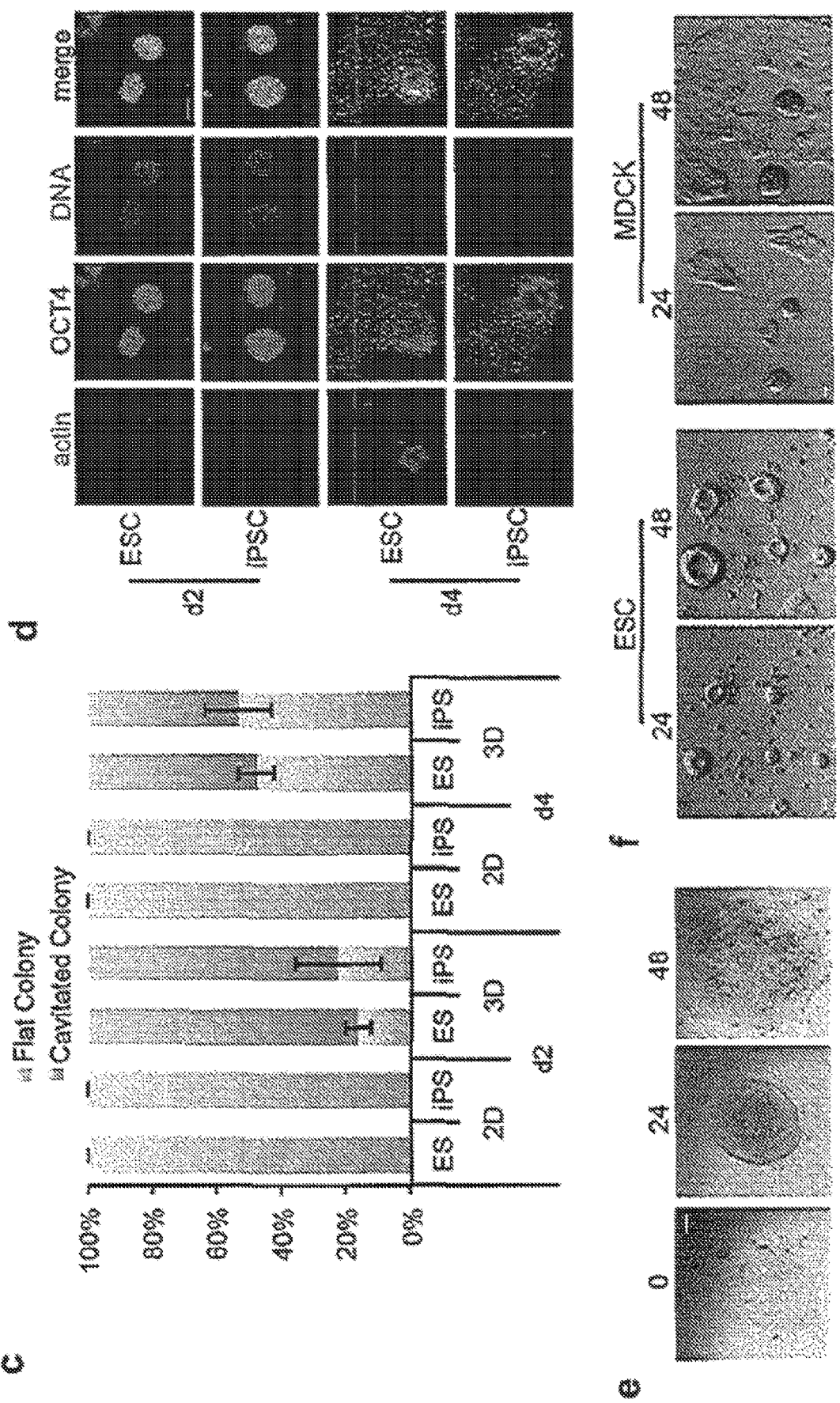

FIG. 11. hPSCs form spheroids in 3D culture. (a) Representative schematic and (b) high and low contrast brightfield images of hESCs or iPSCs growing in sandwich (3D) or monolayer (2D) cultures. Consecutive days are shown, with d0 indicating the time point immediately before sandwiching. (c) Percentage of flat versus cavitated colonies and (d) colocalization of filamentous actin and OCT4 in 2D and 3D cultures on days 2 and 4 after sandwiching. (e) Brightfield time course showing a whole hESC colony 0, 24, and 48 hours after sandwiching. (f) hESCs and MOCK cells 24 and 48 hours after sandwiching. Scale bars, 50 µm. Error bars, s.e.m.

Figure 12:
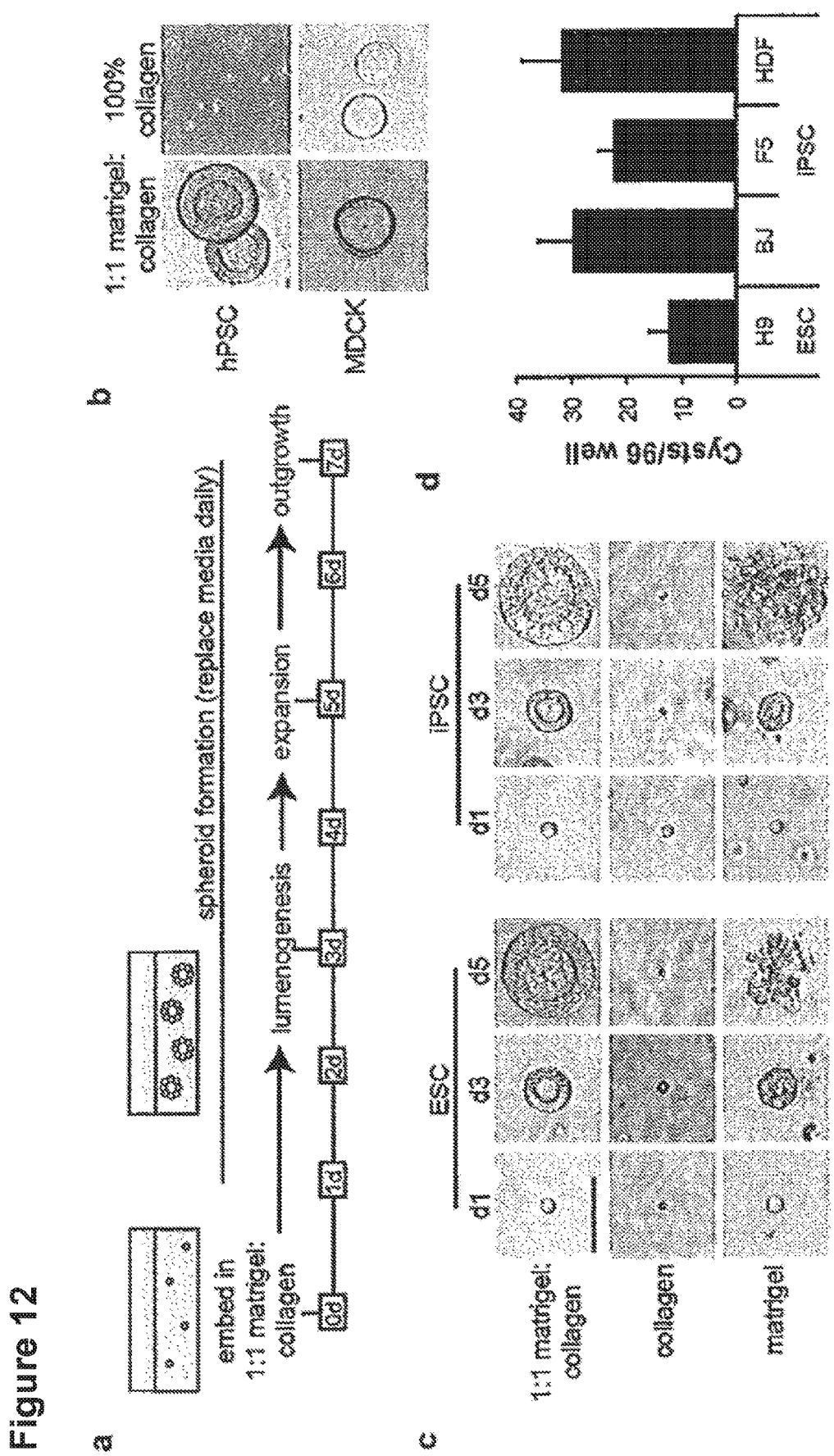
Figure 12:
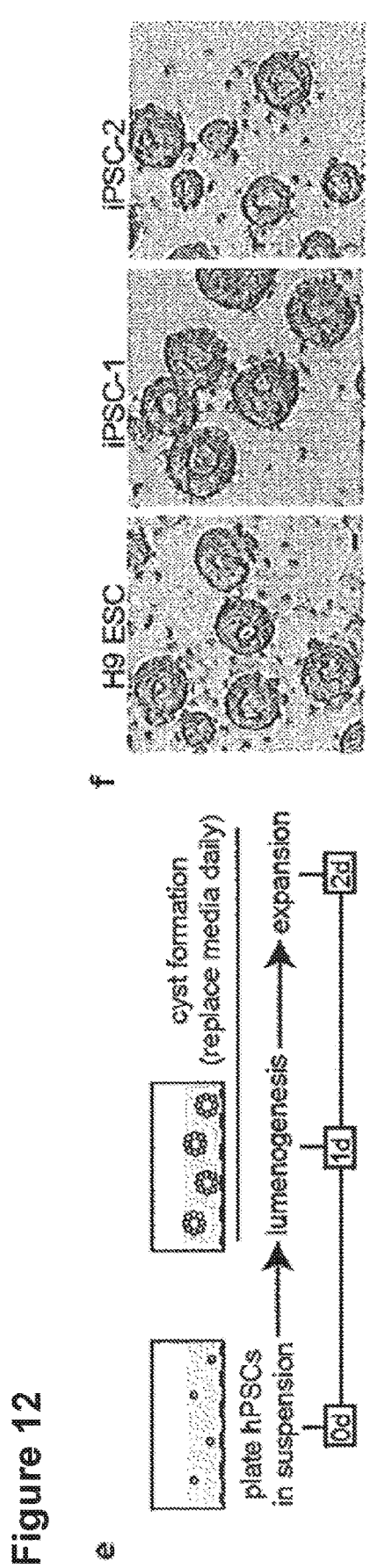

FIG. 12. 3D culture requirements of hPSC spheroid cavity formation. (a) Schematic timecourse of hPSC spheroid formation in 1:1 MATRIGEL™:collagen thick gels. (b) Representative brightfield images of hPSCs or MOCK cells after 7 days in thick gels. (c) Representative timecourse of hPSC growth in thick gels. (d) Quantification of cavitates spheroids/well of a 96-well plate for hESCs and iPSCs cultured for 6 days in 1:1 MATRIGEL™:collagen. (e) Schematic of cyst formation in suspension culture. (f) Representative suspension culture cysts from hESCs or iPSCs from two patients. Scale bars, 20 µm. Error bars, standard error.

Figure 13A:
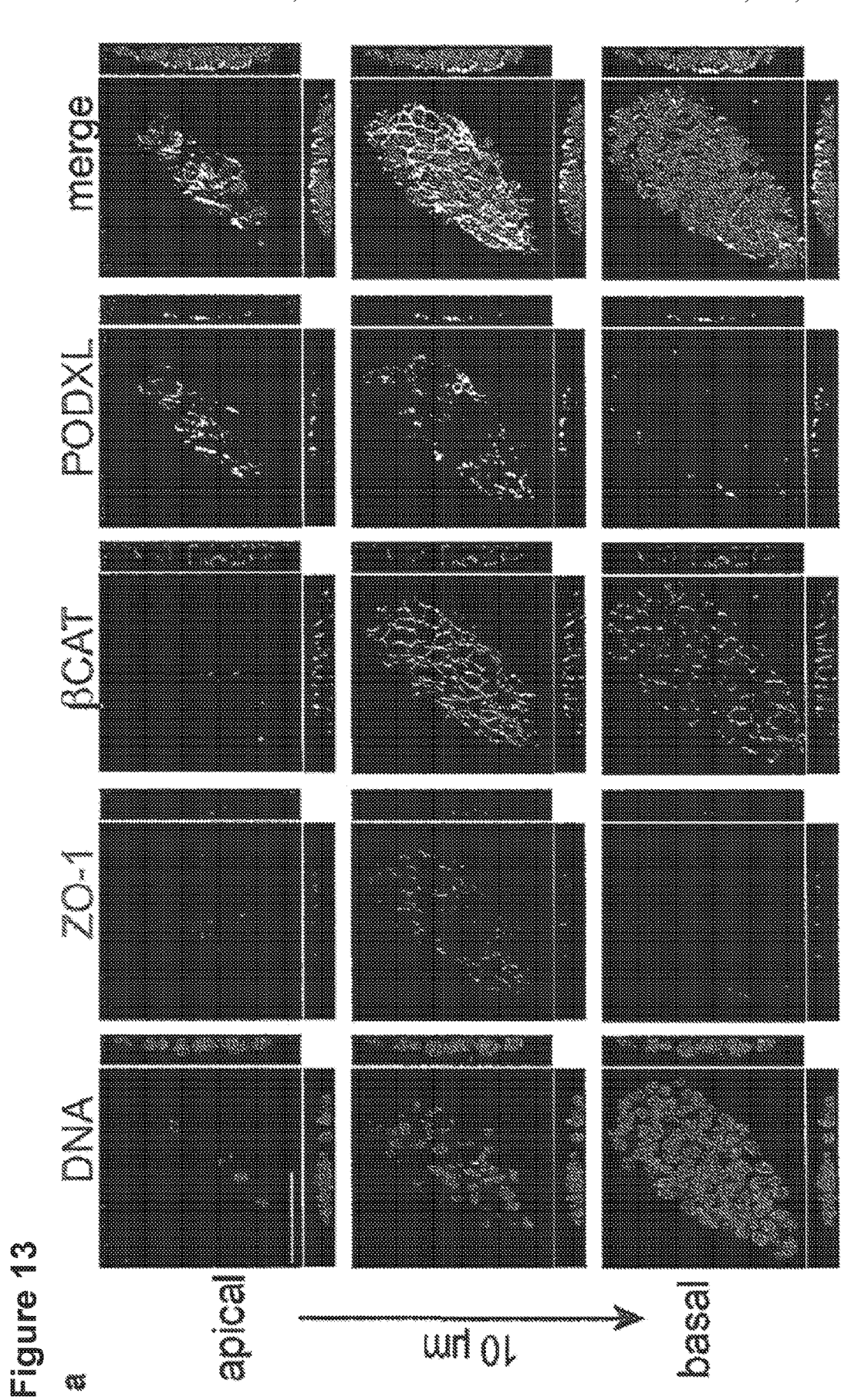
Figure 13:
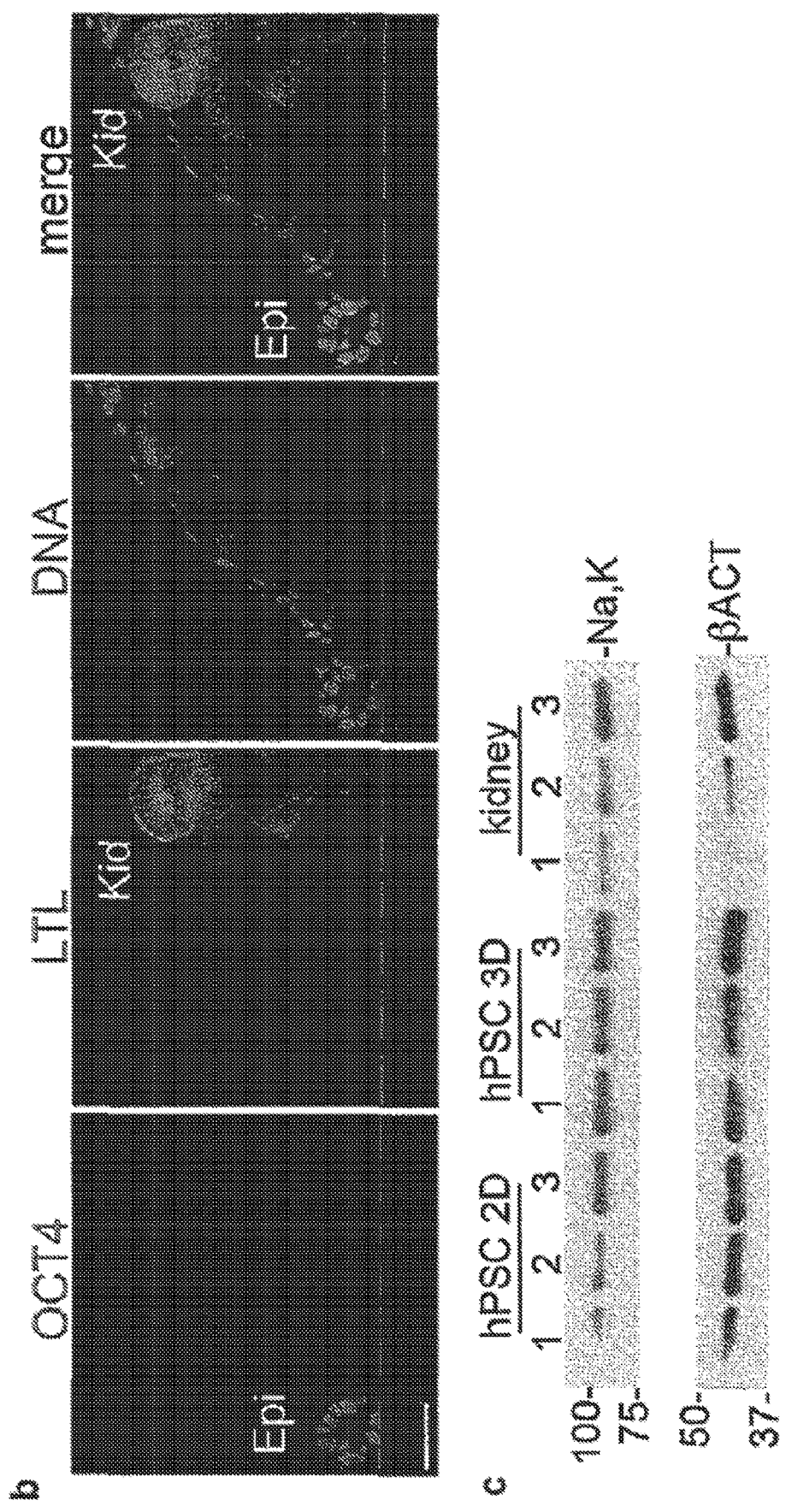

FIG. 13. Epithelial marker expression in hPSCs and tubular organoids. (a) Confocal z-stack showing podocalyxin, ZO-1, and β-catenin immunofluorescence through a representative hPSC monolayer colony. Three optical sections through a single colony are shown, from the apical side to the basal side. Podocalyxin is the most apical marker, as shown in the most apical optical section, where it can be seen even in areas of the colony where ZO-1 is not evident. In the middle optical section, ZO-1 appears in a cobblestone pattern at cell-cell contact points. In the most basolateral section, only β-catenin is visible. The sections are accompanied by orthogonal 3D reconstructions of the entire z-stack, which show that ZO-1 is strongly concentrated at areas of cell-cell contact. Vertical distance from top to bottom row is shown at left. (b) Confocal optical section showing co-localization of OCT 4 and LTL in epiblast spheroid (Epi) and kidney organoid (Kid) co-culture. Kidney organoids were picked, transferred to cultures of spheroids from the same iPSC line, and allowed to adhere overnight before fixation and processing for immunofluorescence. (c) Na,K-ATPase immunoblot with β-actin loading control in three different hPSC clones. 2D and 3D cultures of undifferentiated hPSCs were plated identically. Kidney organoids were isolated manually and lysed. Scale bars, 50 µm.

Figure 14:
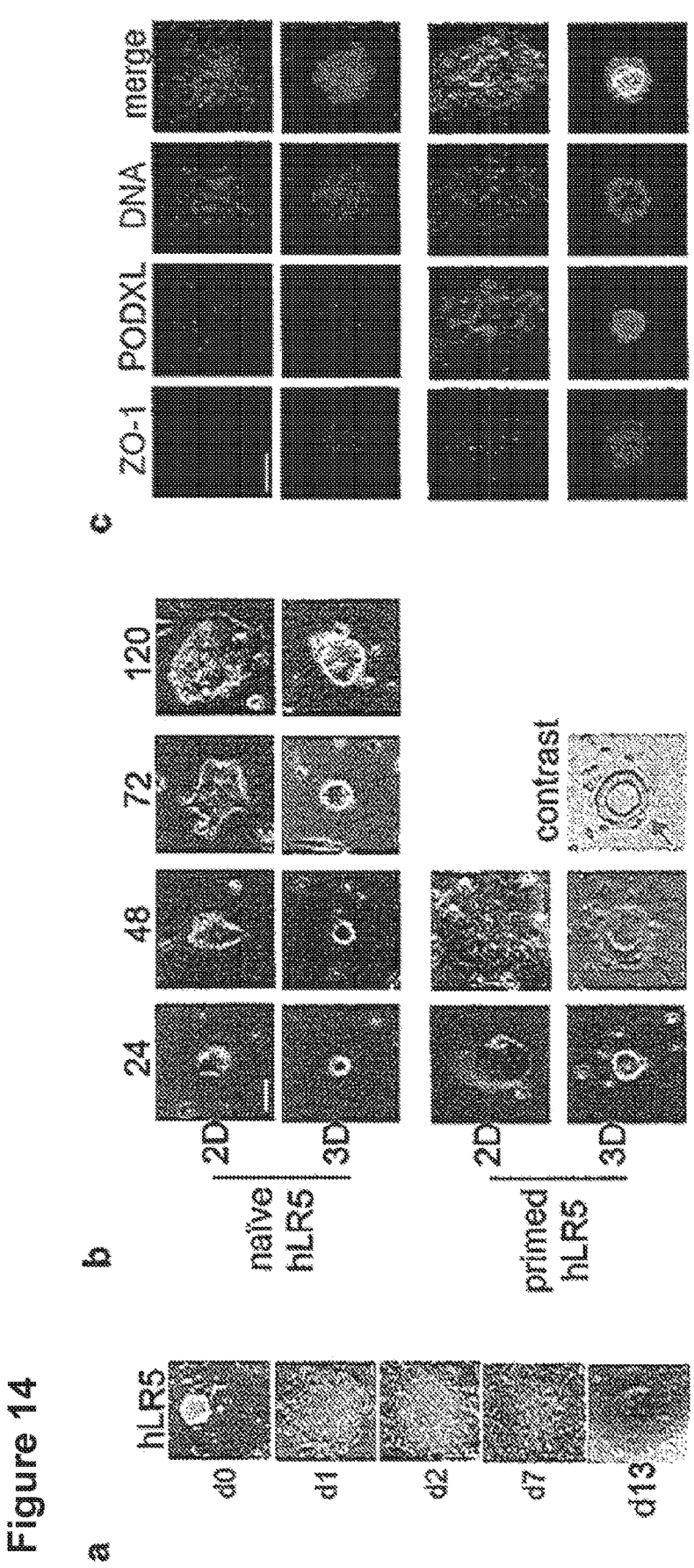
Figure 14:
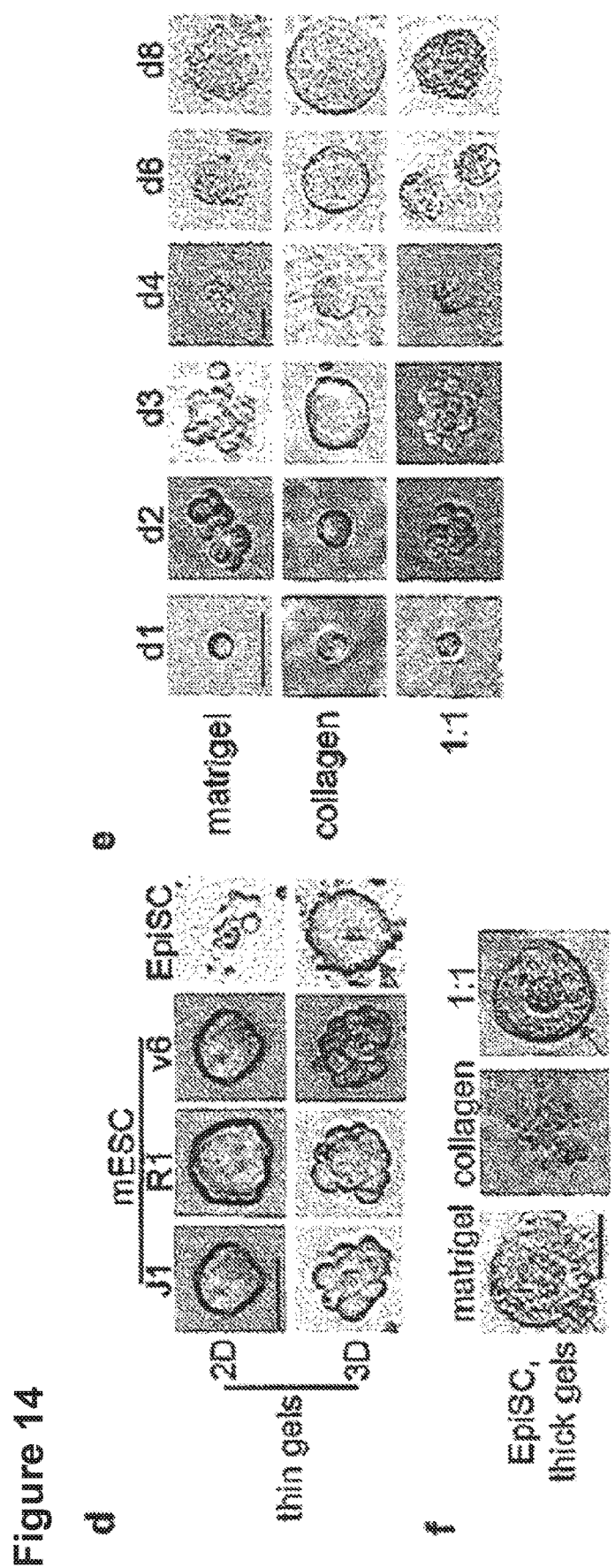
Figure 14:
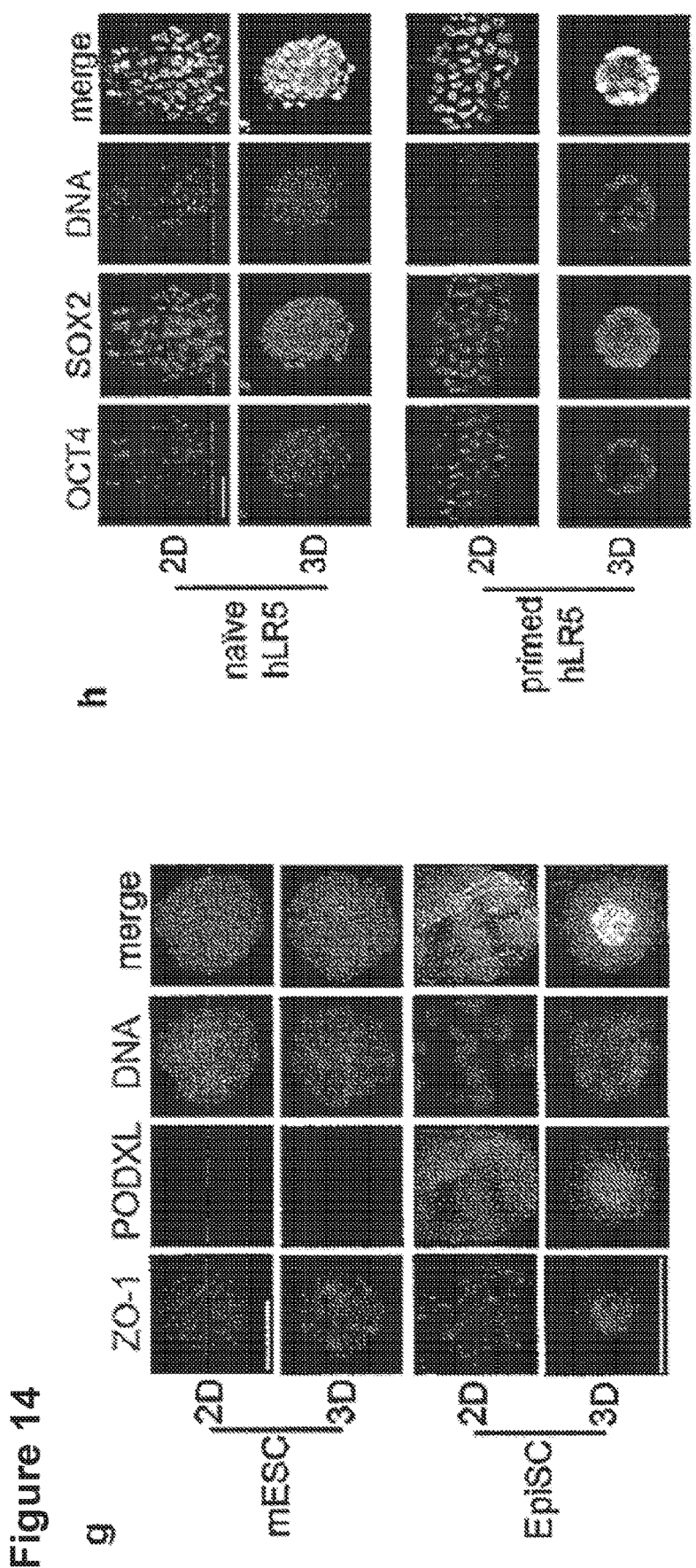

FIG. 14. Cavity formation is restricted to epiblast-stage PSCs. (a) Time course showing transition of naive hLR5 iPSCs to primed LD-hLR5. (b) Naive and primed hLR5 morphologies with corresponding (c) ZO-1 and podocalyxin immunofluorescence in 20 and 3D cultures. (d) Brightfield morphology of mESCs or EpiSCs in thin gels 48 hours after sandwiching. Red arrows indicate structures initiating lumenogenesis. Time points (24, 48, etc) represent hours after sandwiching and show different colonies. (e) mESC colonies grown from single cells in thick gels of either MATRIGEL™, buffered collagen, or a 1:1 mixture of the two (1:1). Similar results were obtained from three separate mESC lines. (f) Mouse EpiSCs in thick gels 120 hours after plating. (g) ZO-1 and PODXL immunofluorescence in mESCs and EpiSCs, scaled identically. (h) OCT4 and SOX2 immunofluorescence in naive and primed hLR5 iPSCs. Scale bars, 50 µm.

Figure 15:
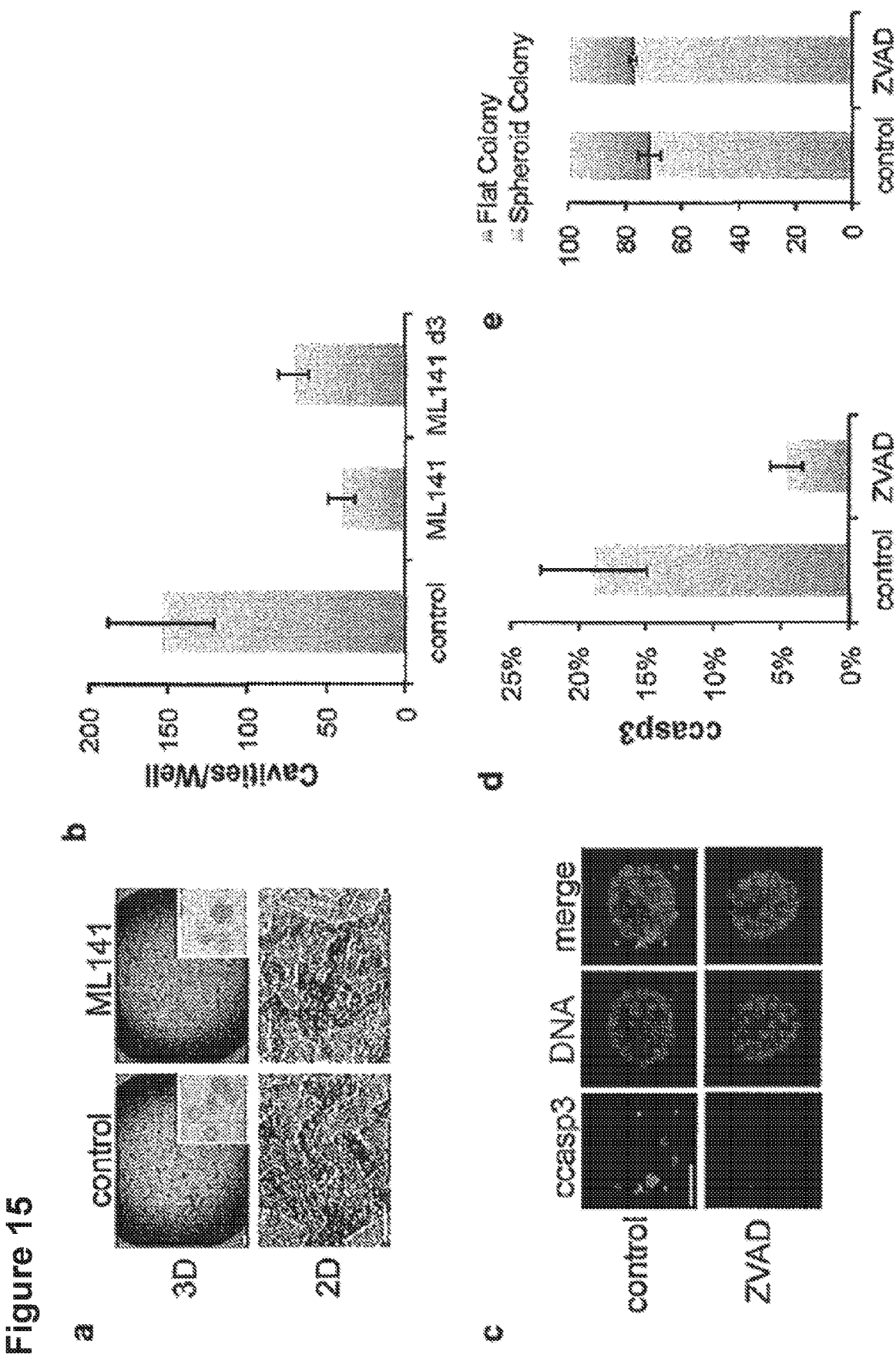

FIG. 15. Epiblast-stage hPSCs undergo polarized lumenogenesis. (a) Brightfield images and (b) quantification of cavitation in hPSCs plated in 96-wells (top) or 24-well monolayers (bottom) and treated with µM of the CDC42 inhibitor ML 141 or vehicle control. (c) Representative immunofluorescence, (d) percentage of cells expressing cleaved caspase-3 (ccasp3), and (e) cavity counts in hPSC spheroids treated with 50 µM of the caspase inhibitor ZVAD(-fluoromethylketone) or vehicle control. Scale bars, 50 µm. Error bars, s.e.m.

Figure 16:
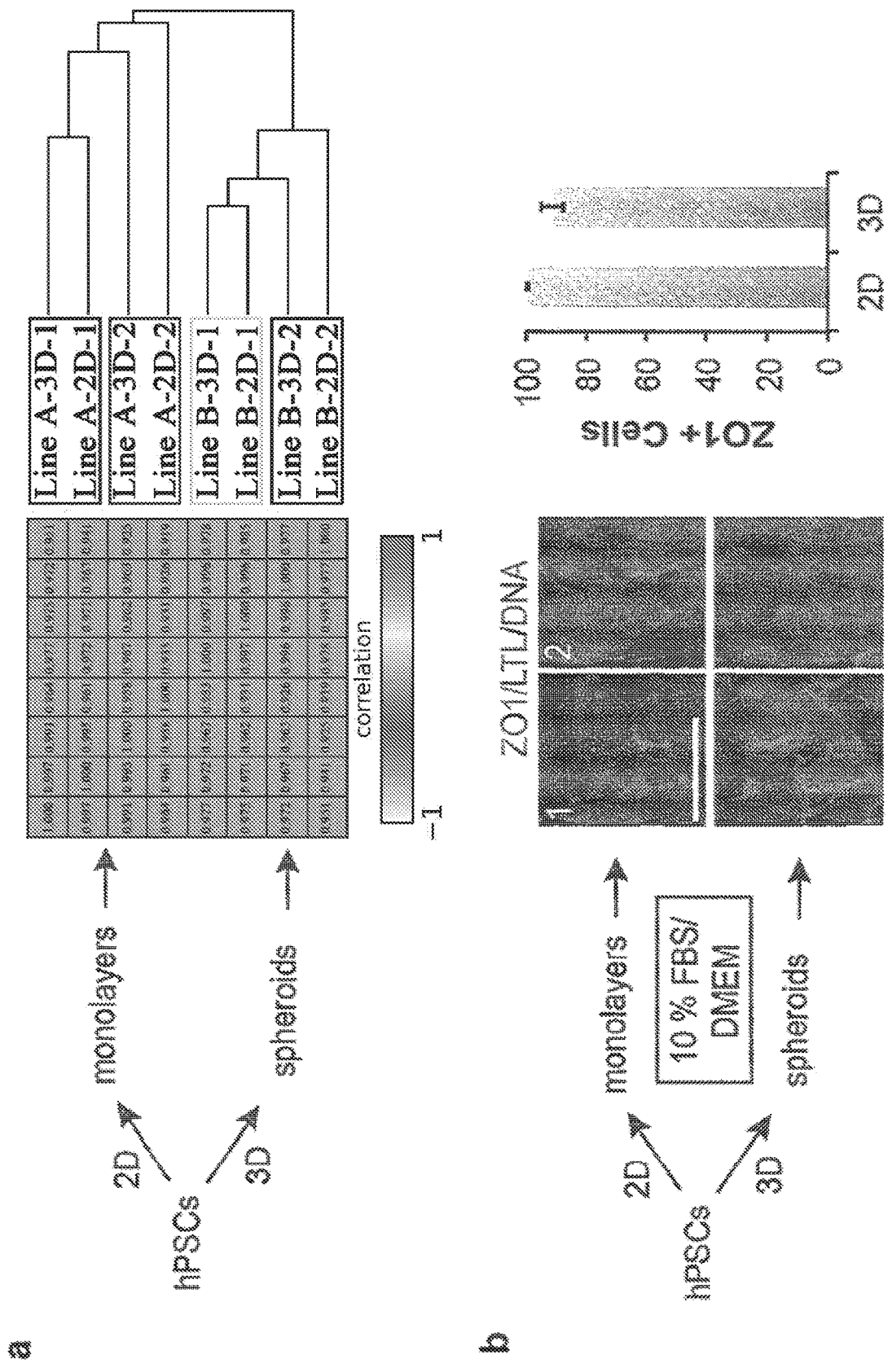
Figure 16:
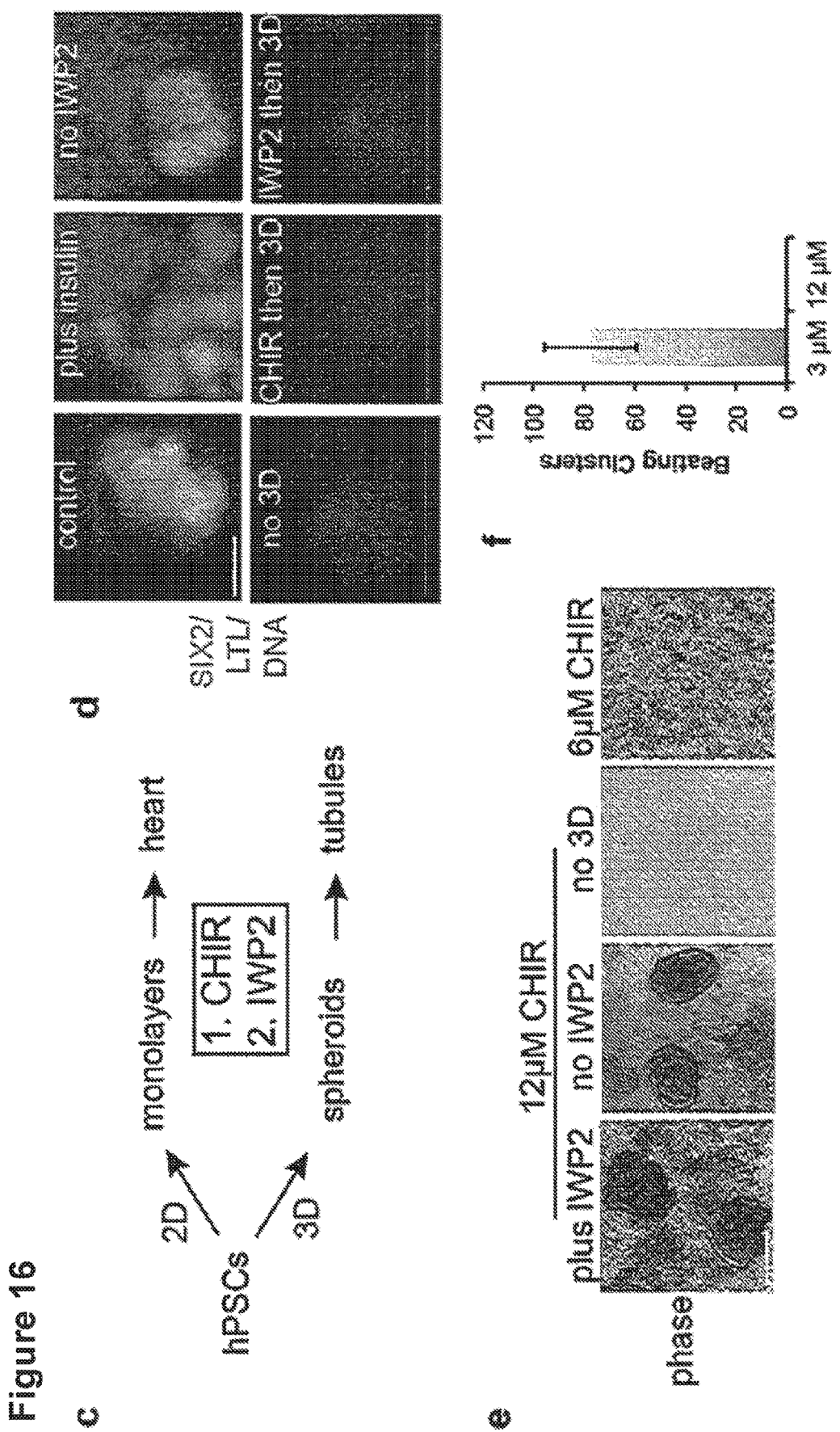

FIG. 16. Generation of kidney-like tubular organoids in 3D cultures. (a) Schematic of RNA-Seq experiment and resultant hierarchical clustering of hPSCs in 2D monolayers and 3D spheroids. Two lines are shown (A and B) on two different dates (−1 and −2). Samples in the plot are arranged according to highest correlation as further demonstrated by the dendrogram on the right side. The heatmap grid demonstrates the extent of correlation and is composed of the corresponding RA2 values. (b) Schematic of stochastic differentiation protocol and representative images from two hPSC lines after 21 days. Quantification of ZO-1+ cells is shown at right. (c) Schematic of original 2D cardiomyocyte differentiation protocol and application to 3D spheroids. (d) Day 22 structures representing identically-plated hPSC spheroids treated with the described cardiomyocyte differentiation protocol (control) or the following variations (from left): use of B27 supplement including insulin, no IWP2 treatment, no sandwiching, sandwiching after CHIR treatment, sandwiching after IWP2 treatment. (e) Day 22 structures representing identically-plated cultures treated with CHIR in RPMI with the labeled variations. (f) Beating clusters per 24 well obtained in 3D cultures plated identically and treated with different dose of CHIR. Error bars, s.e.m. (n≥3 separate experiments). Scale bars, 20 µm (b) or 100 µm (d-e).

Figure 17:
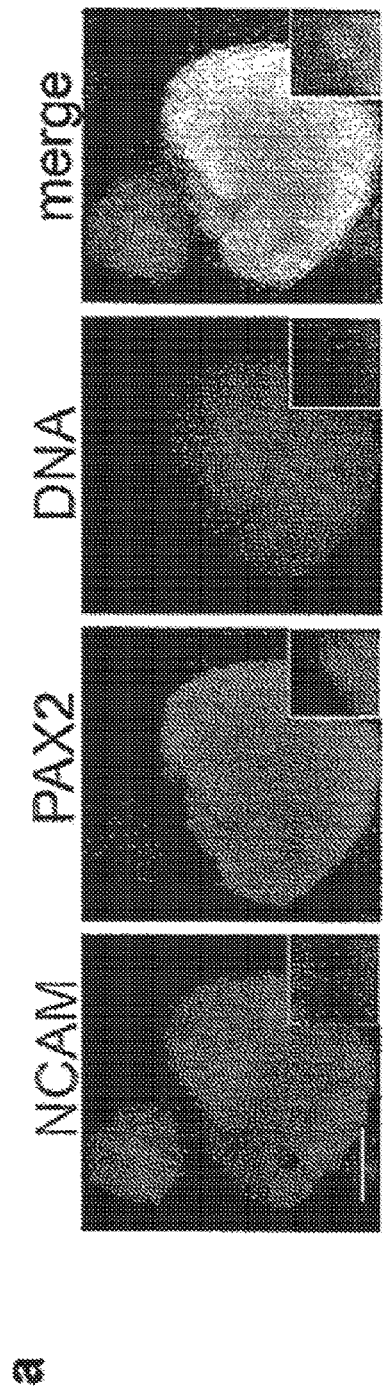
Figure 17:
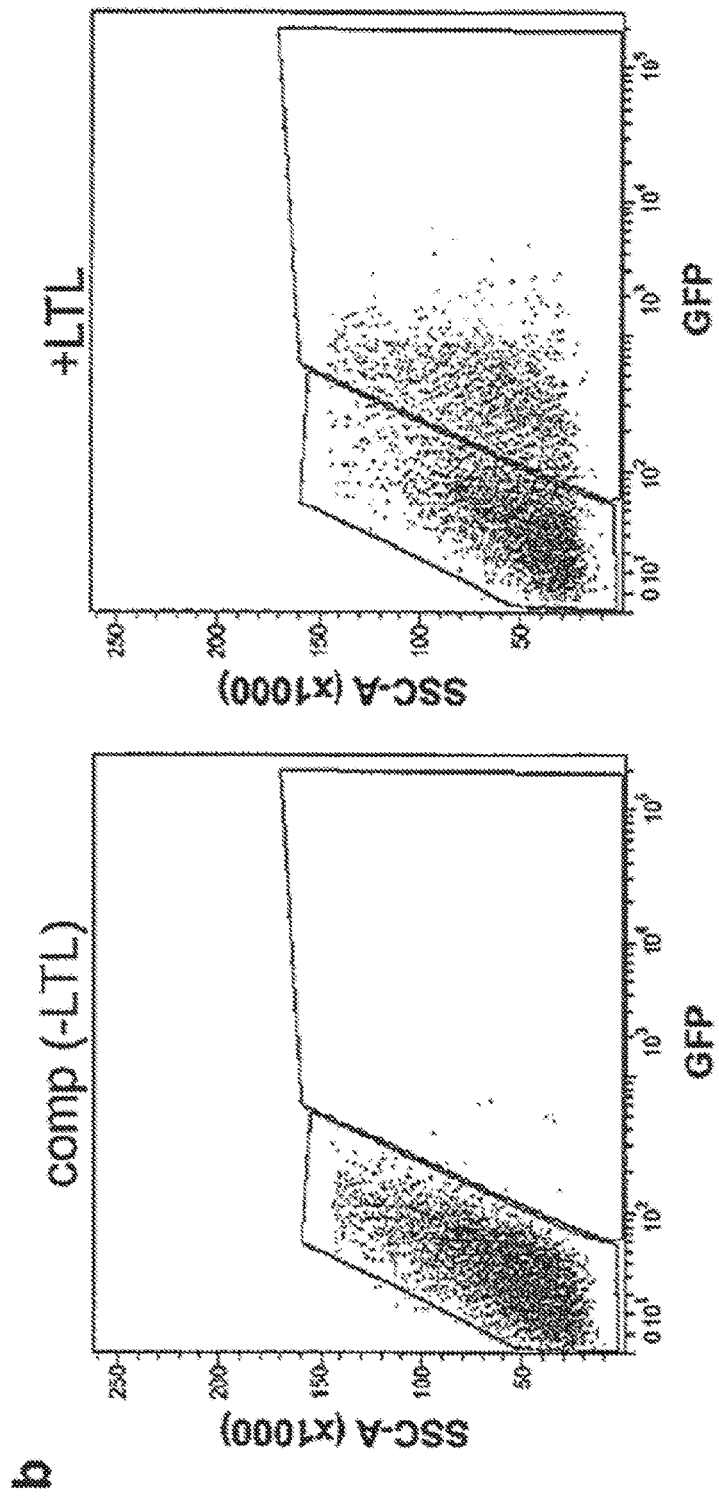
Figure 17:
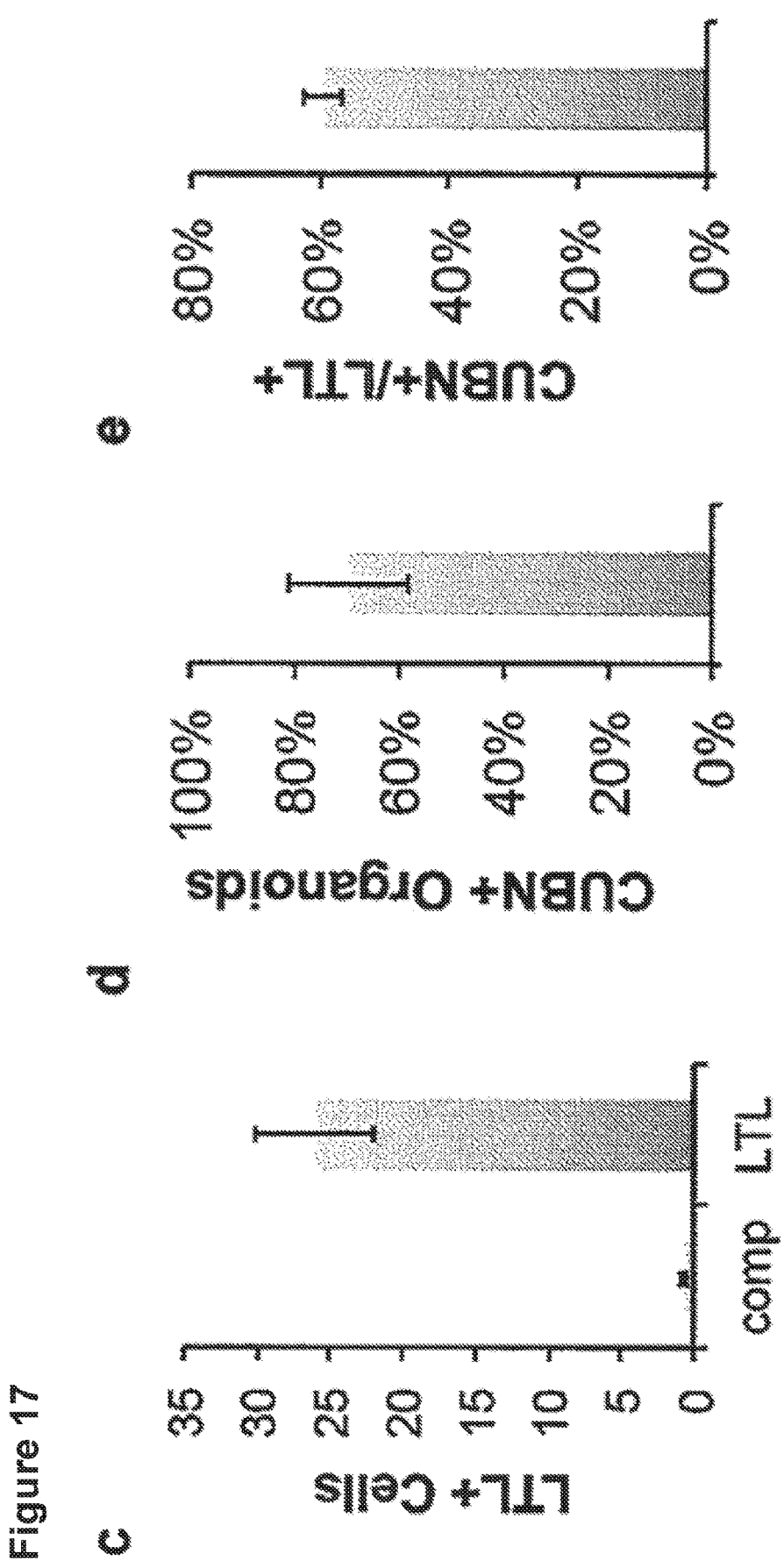

FIG. 17. Quantification of kidney organoid differentiation. (a) Nephron progenitor marker expression in a representative organoid. (b) Flow cytometry analysis of LTL binding in kidney organoid cells as a percentage of the population. Identically-plated wells of kidney organoids were incubated with LTL or without LTL as a compensation control (comp). Cells were then dissociated and subjected to flow cytometry. (c) Percentage of all cells that were LTL+ by FACS. (d) Percentage of LTL+organoids with detectable tubular CUBN. (e) Fraction of LTL+tubular length that co-expressed CUBN. Error bars, s.e.m. (n≥separate experiments and ~90 organoids examined per experiment).

Figure 18:
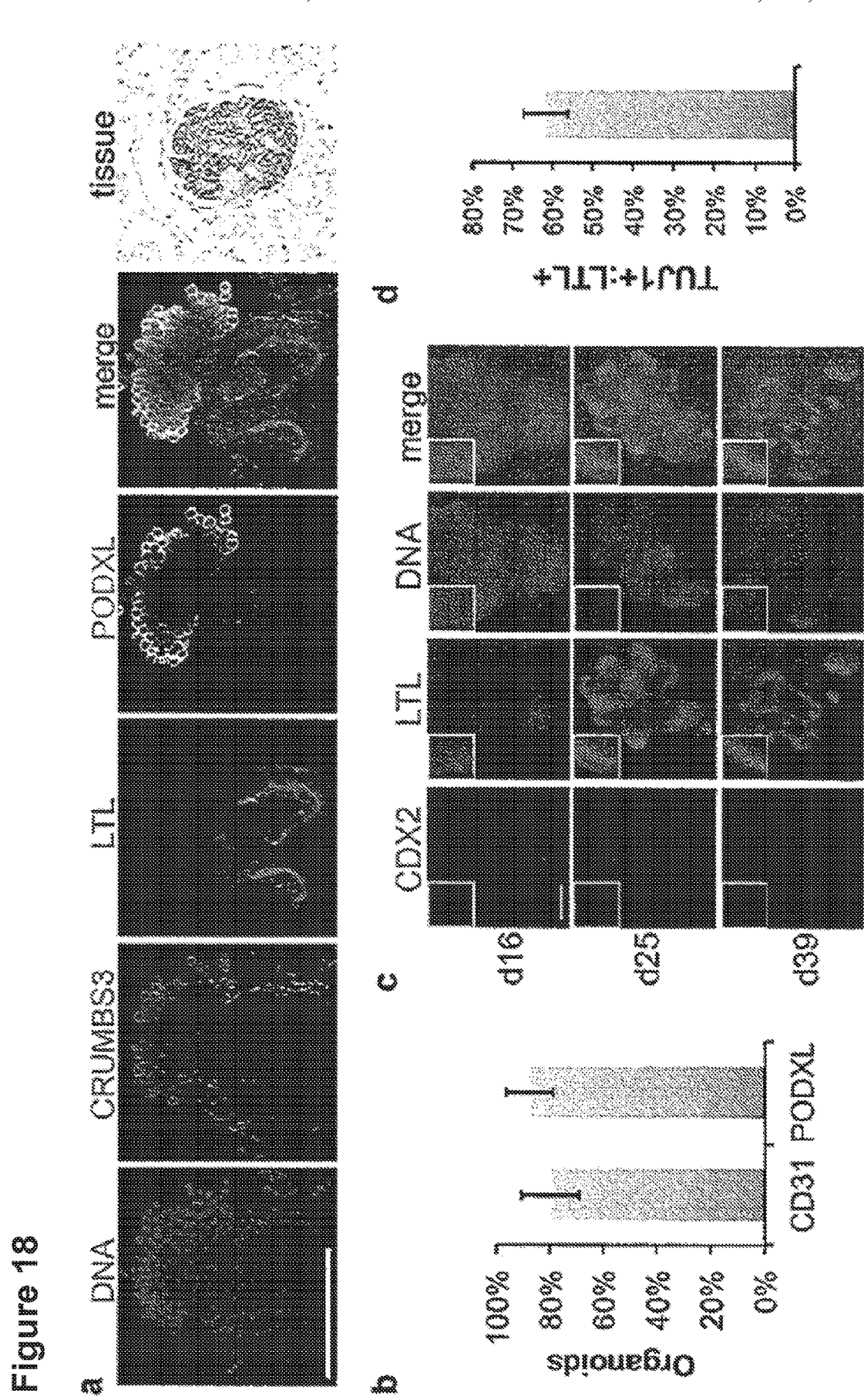
Figure 18:
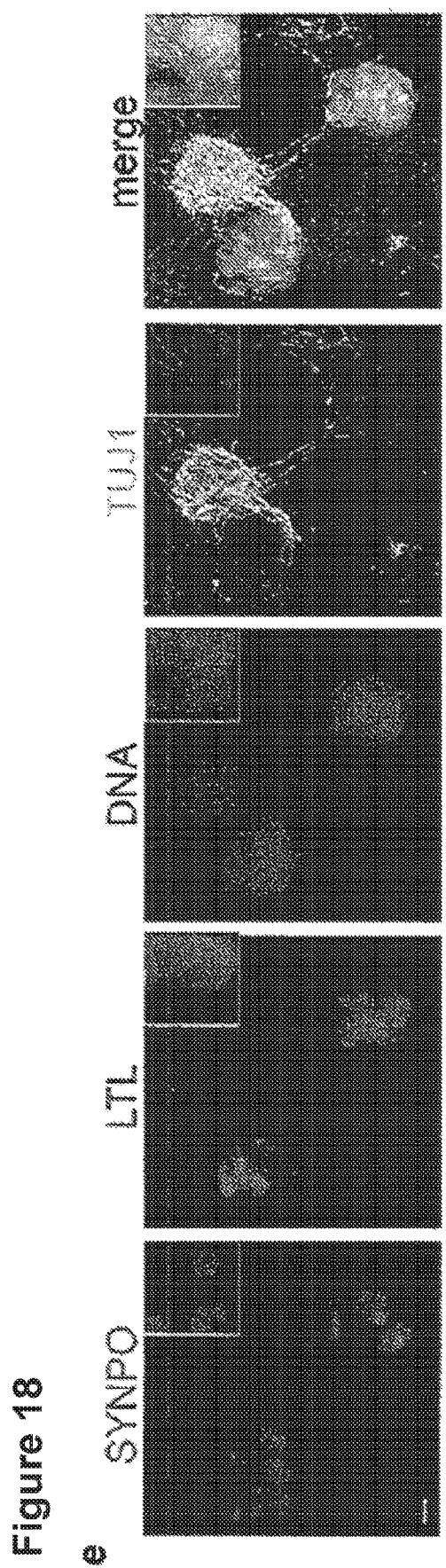

FIG. 18. Quantification of kidney organoid differentiation. (a) Crumbs 3 expression in hPSC-derived kidney organoids (left) and human kidney tissue (right). (b) Percentage of LTL+organoids associated with CD31+ and PODXL+ cell types. (c) Time course in organoid cultures (rows indicate days of culture) showing absence of LTL co-staining with the intestinal marker CDX2. (d) Average ratio of neural (TUJ1+) clusters to kidney (LTL+) organoids in these cultures. (e) Wide-field low-resolution images showing neural clusters at low magnification. Error bars, s.e.m. (n≥3 separate experiments and ~30 organoids examined per experiment).

Figure 19:
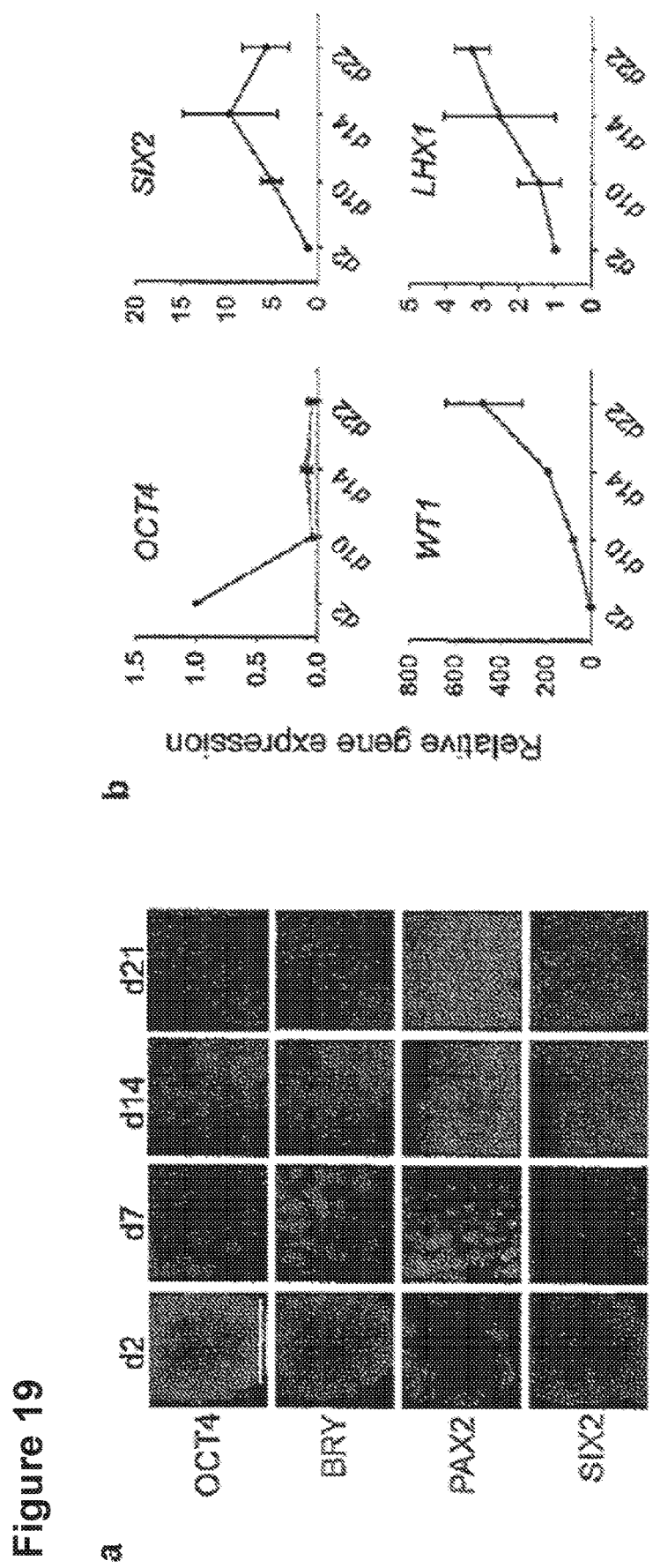
Figure 19:
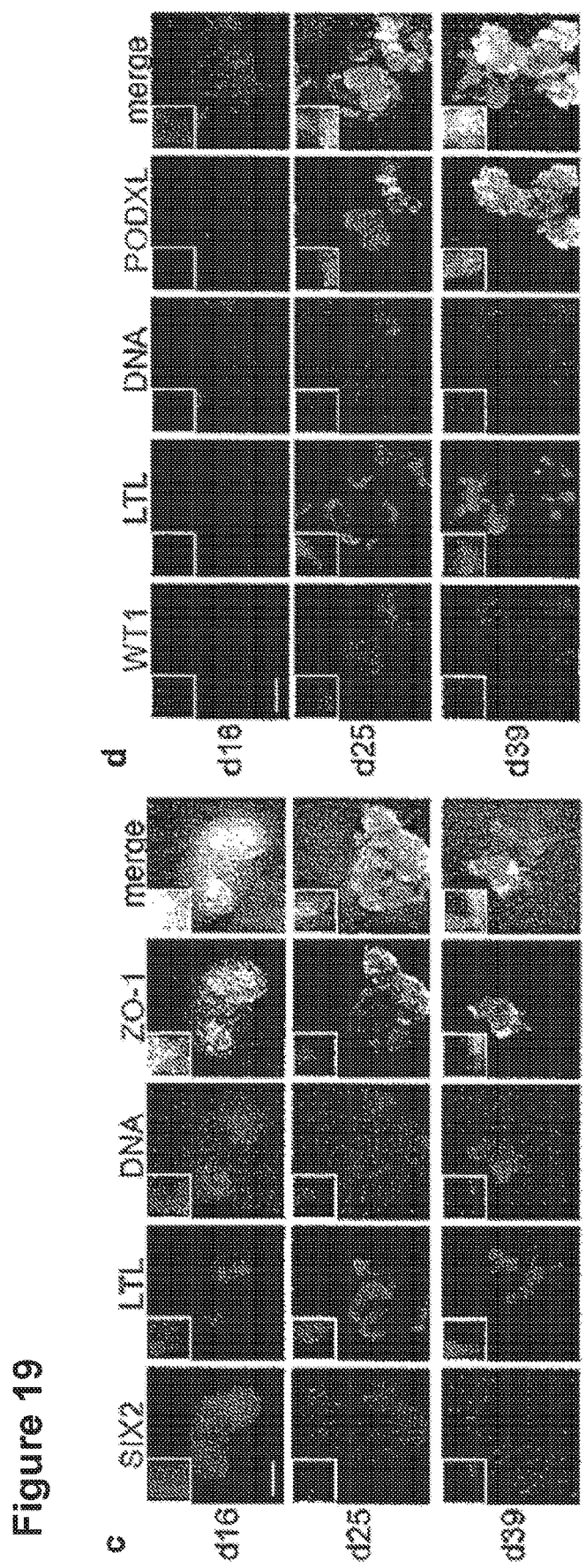
Figure 19:
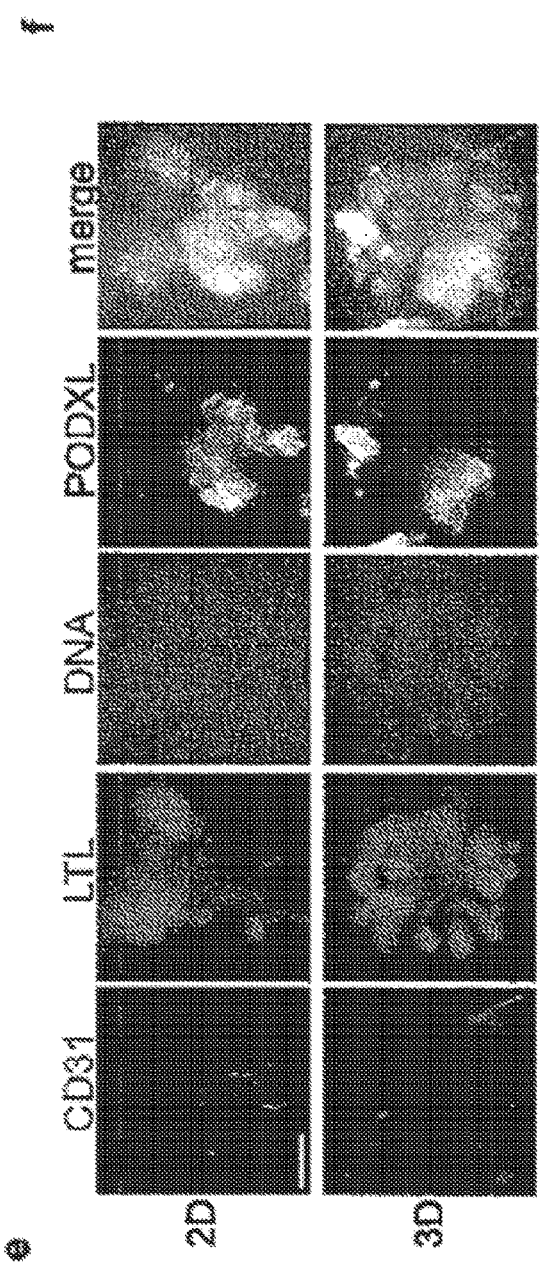
Figure 19:
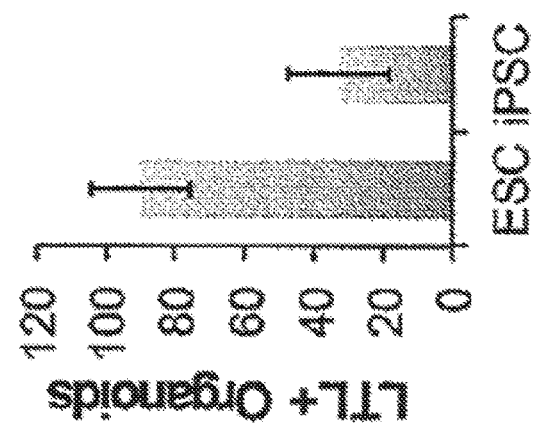

FIG. 19. Time course of differentiation of hPSCs into kidney tubular organoids. (a-b) Immunofluorescence or (b) quantitative RT-PCR time courses sequential expression of stage-specific developmental markers for pluripotency (OCT4), primitive streak (BRY), intermediate mesoderm (PAX2), nephron progenitor (PAX2, SIX2, LHX1, WT1), and podocytes (WT1). d2 represents epiblast spheroids on day 2 after sandwiching, just before CHIR treatment. (c) Time course in organoid cultures (rows indicate days of culture) showing LTL co-staining with SIX2 and ZO-1, or (d) PODXL and WT1. (e) Marker expression in tubular organoids derived using a published 20 protocol for kidney differentiation, compared to tubular organoids produced in 3D using the protocol described here. Cells were plated identically and processed simultaneously for immunofluorescence on the same day of differentiation. (f) Tubular organoid formation in iPSCs compared to ESCs. Scale bars, 50 µm (a) or 100 µm (c-e). Error bars, s.e.m (n=3).

Figure 20A:
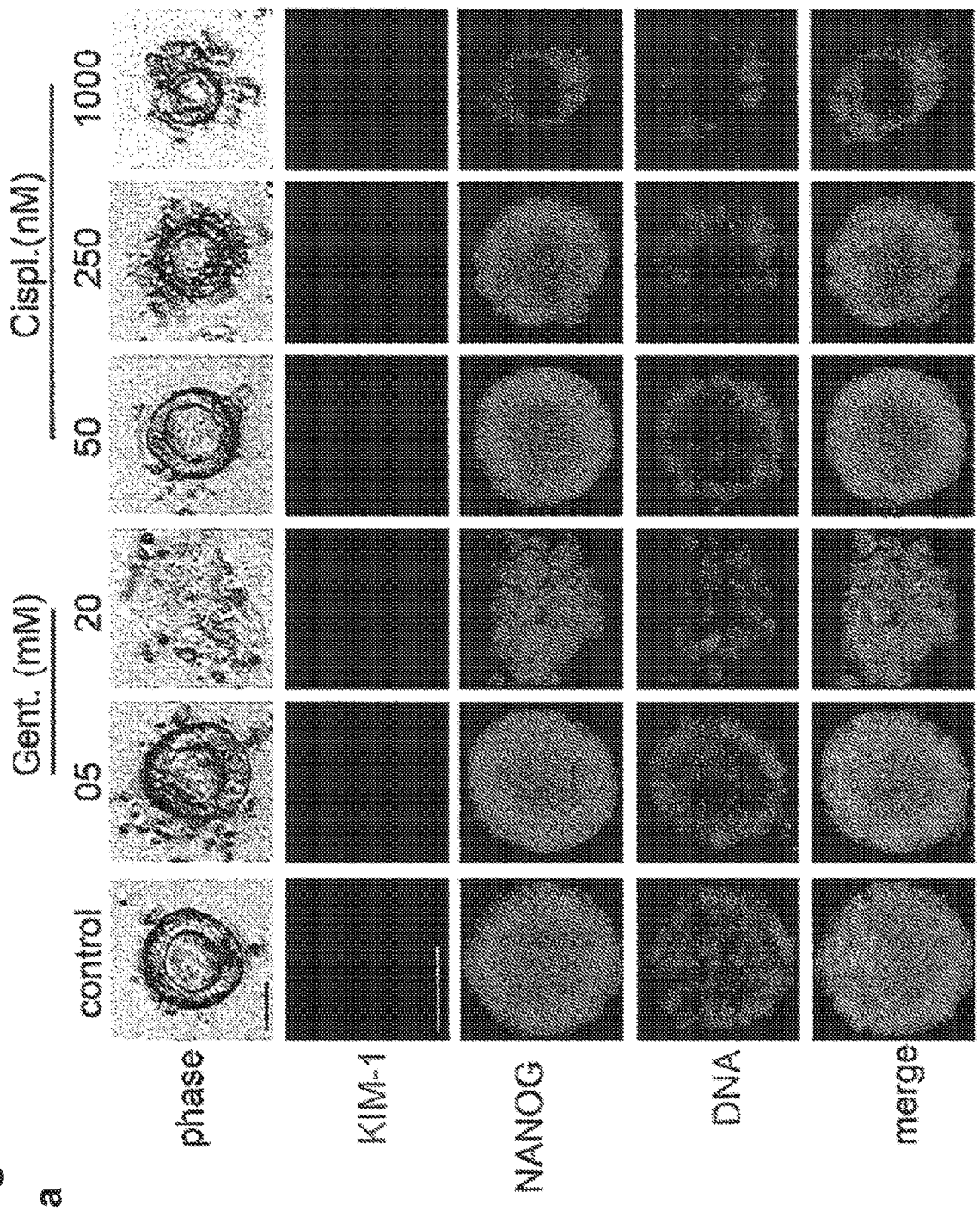

FIG. 20. Epiblast spheroids do not express KIM-1. (a) Phase contrast of living cells, or KIM-1 and NANOG immunofluorescence, in epiblast spheroids treated with titrations of cisplatin and gentamicin. No KIM-1 expression is observed at doses ~5 mM gentamicin, a concentration sufficient to induce KIM-1 in kidney organoids. Scale bars, 50 µm.

FIG. 21. Generation of kidney lineages in vivo. (a) Confocal sections of of kidneys grafted neonatally with cells from tubular organoids and grown for four weeks. The human PODXL antibody does not react with mouse podocalyxin. Scale bars, 50 µm.

Figure 22:
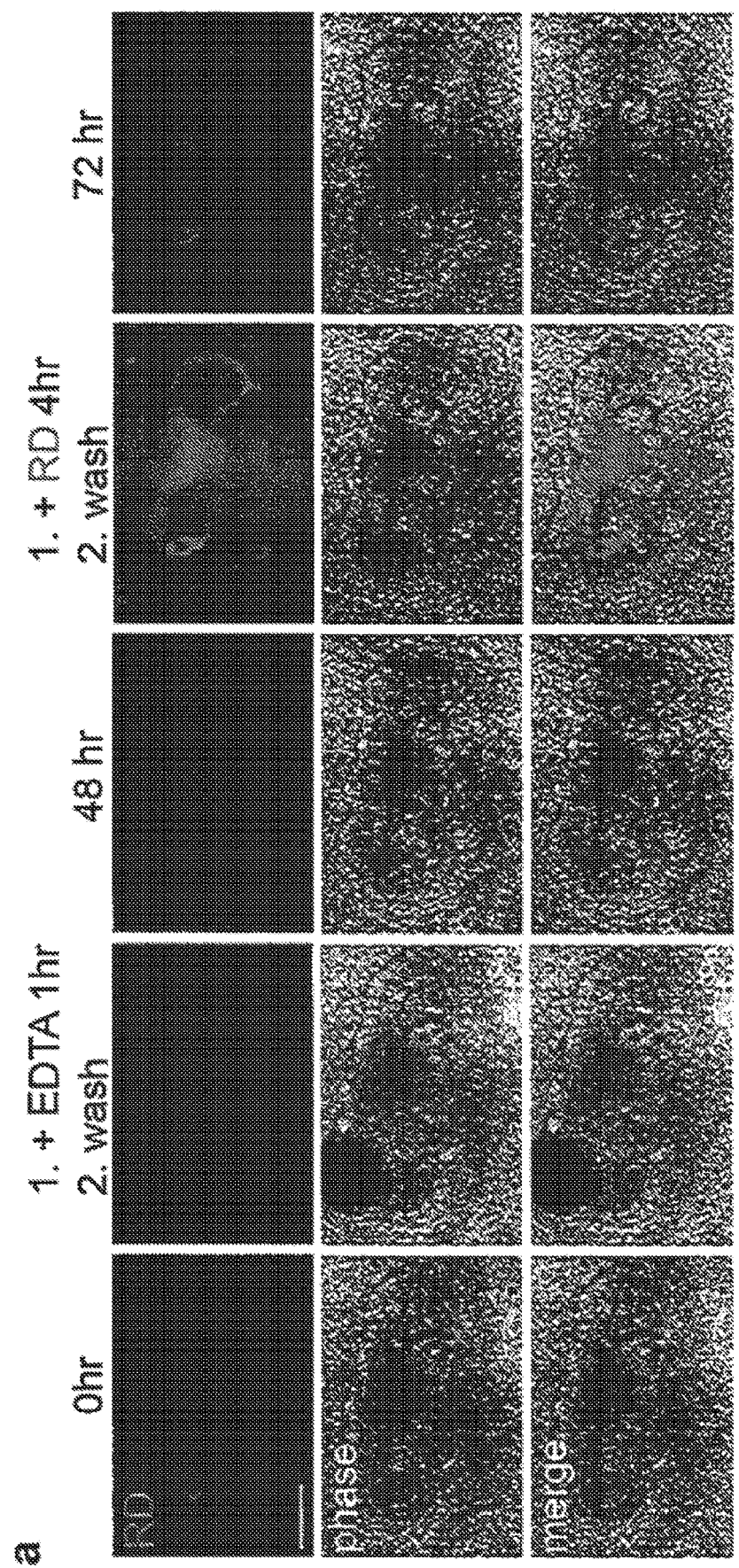
Figure 22:
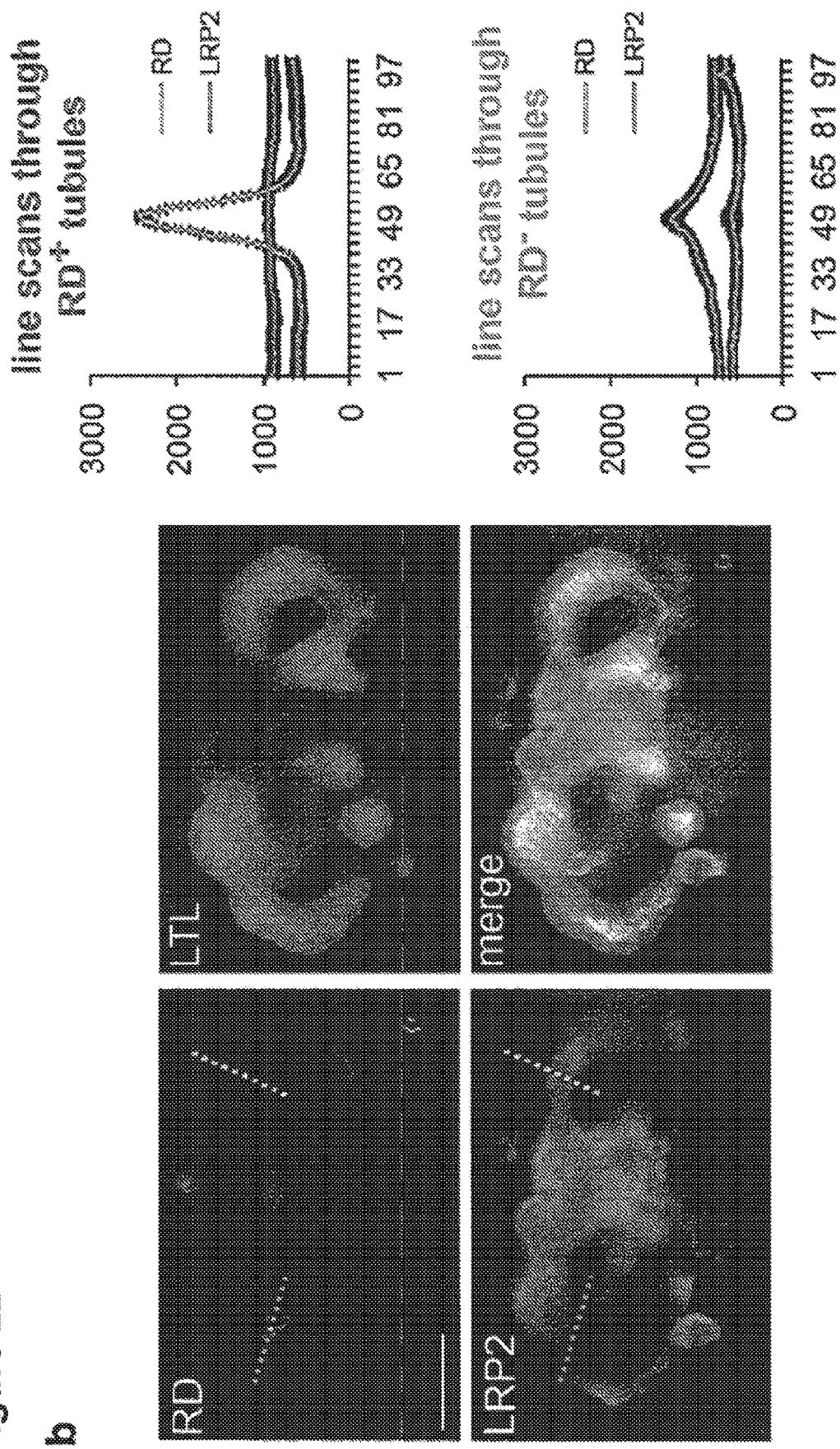

FIG. 22. RD accumulates in tubular segments not expressing LRP2. (a) Time course showing tubules after RD accumulation (0hr), followed by EDTA treatment and RD re-accumulation. An air bubble is visible immediately after the wash. (b) Left: The same organoid fixed and processed for LRP2 immunofluorescence. To quantify fluorescence intensities, line scans were drawn perpendicular to tubule segments containing RD (green dotted line) or not containing RD (orange dotted line). Right: Averaged fluorescence intensities of RD and LRP2 in line scans through tubular regions containing RD (top) or not containing RD (bottom), with black error bars (n=14 tubules per condition). Scale bars, 100 µm. Error bars, s.e.m.

Figure 23:
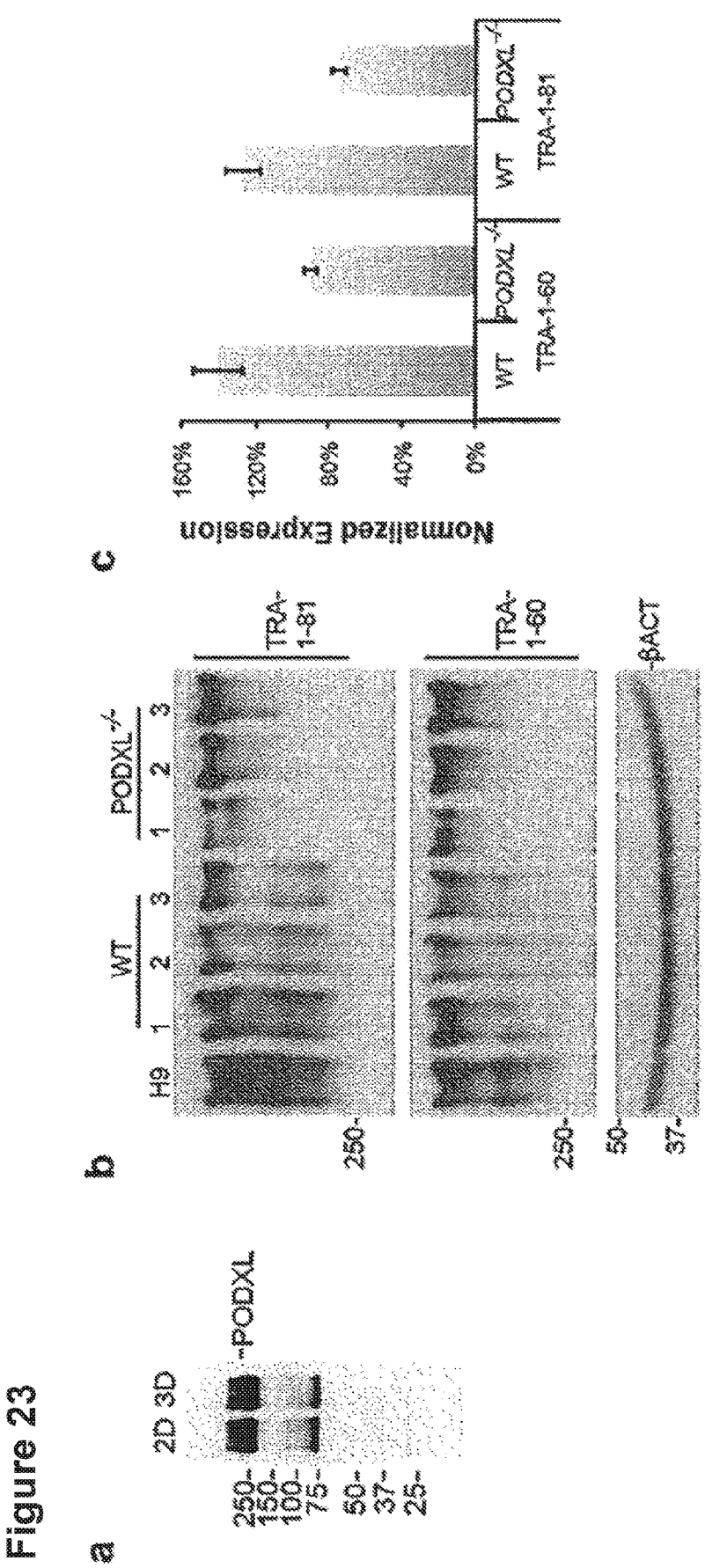
Figure 23:
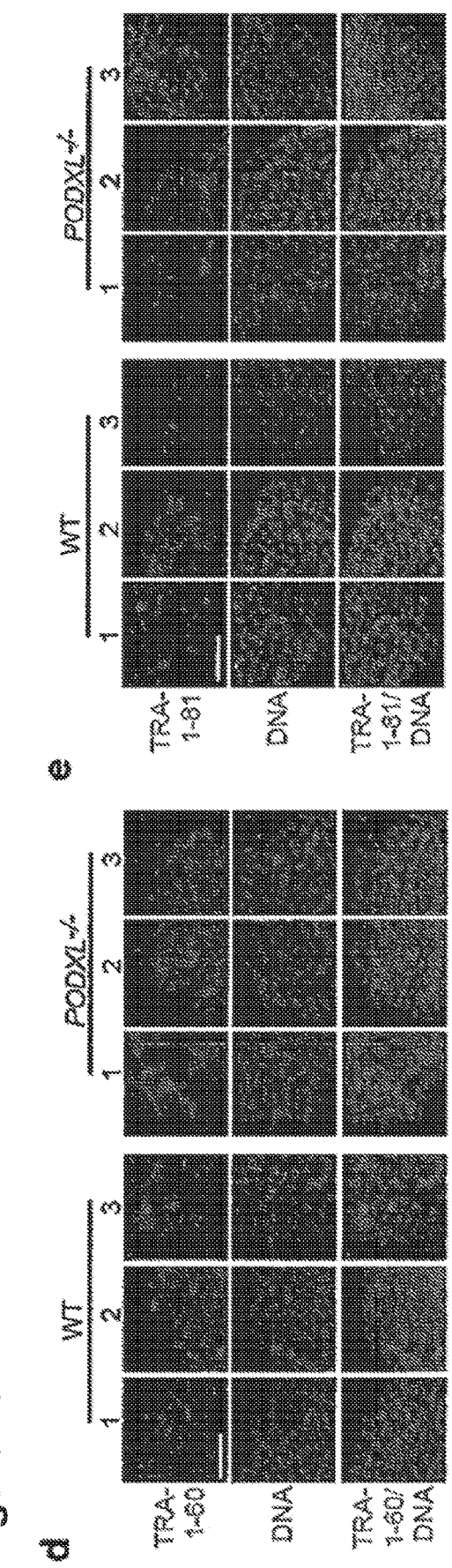

FIG. 23. Characterization of podocalyxin and TRA-1-60/81 in undifferentiated hPSCs. (a) Podocalyxin immunoblot in hPSC monolayers (2D) and spheroids (3D). (b) Immunoblots showing TRA-1-60 and TRA-1-81 (multiple bands>250 kDa), with β-actin loading control. (c) Quantification of band intensities, normalized to β-actin, averaged from 3-4 clones of wild-type or PODXL-/- hPSCs. (d-e) Marker immunofluorescence in representative wild-type and knockout clones. Scale bar, 50 µm. Error bars, s.e.m.

Figure 24:
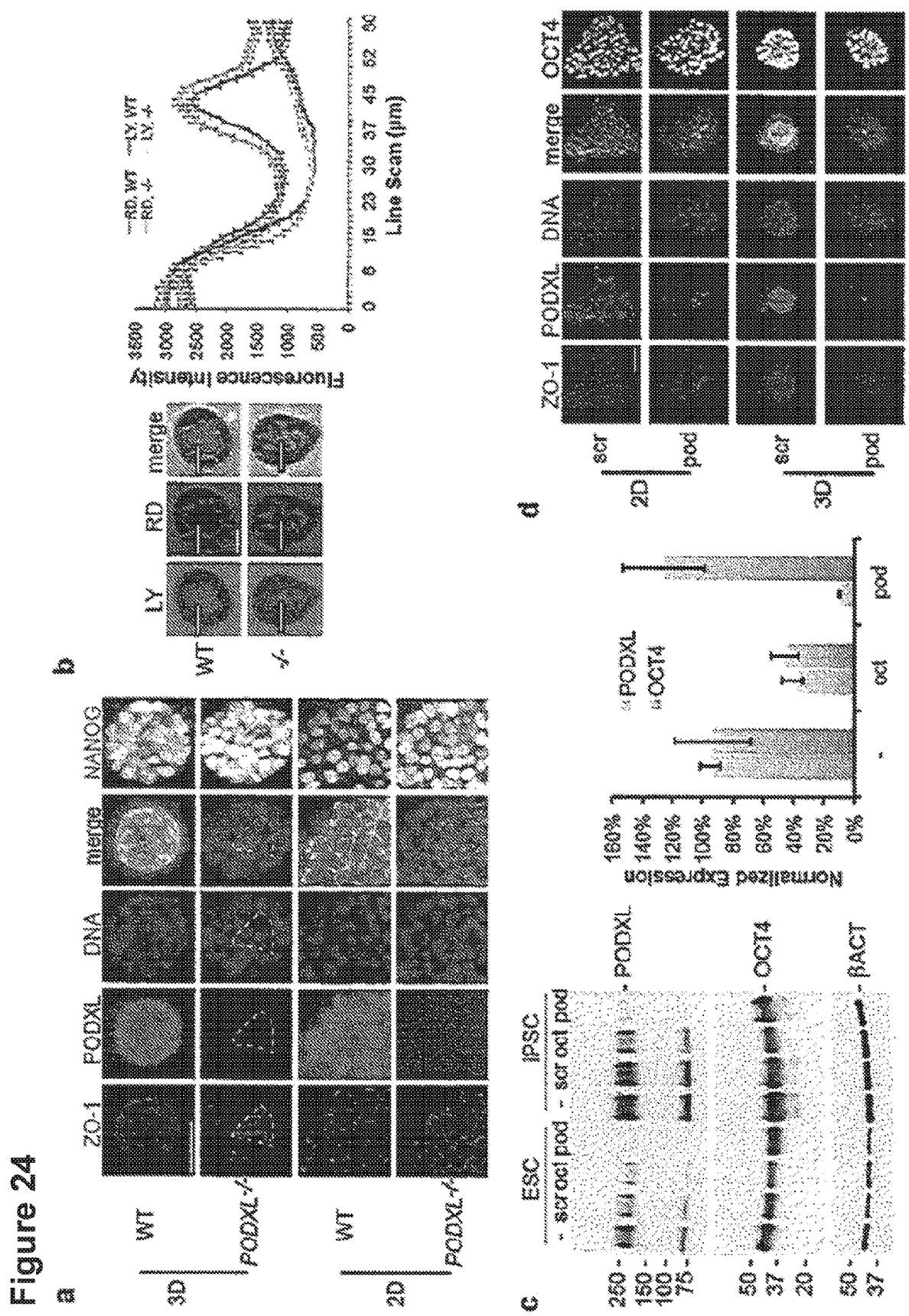
Figure 24:
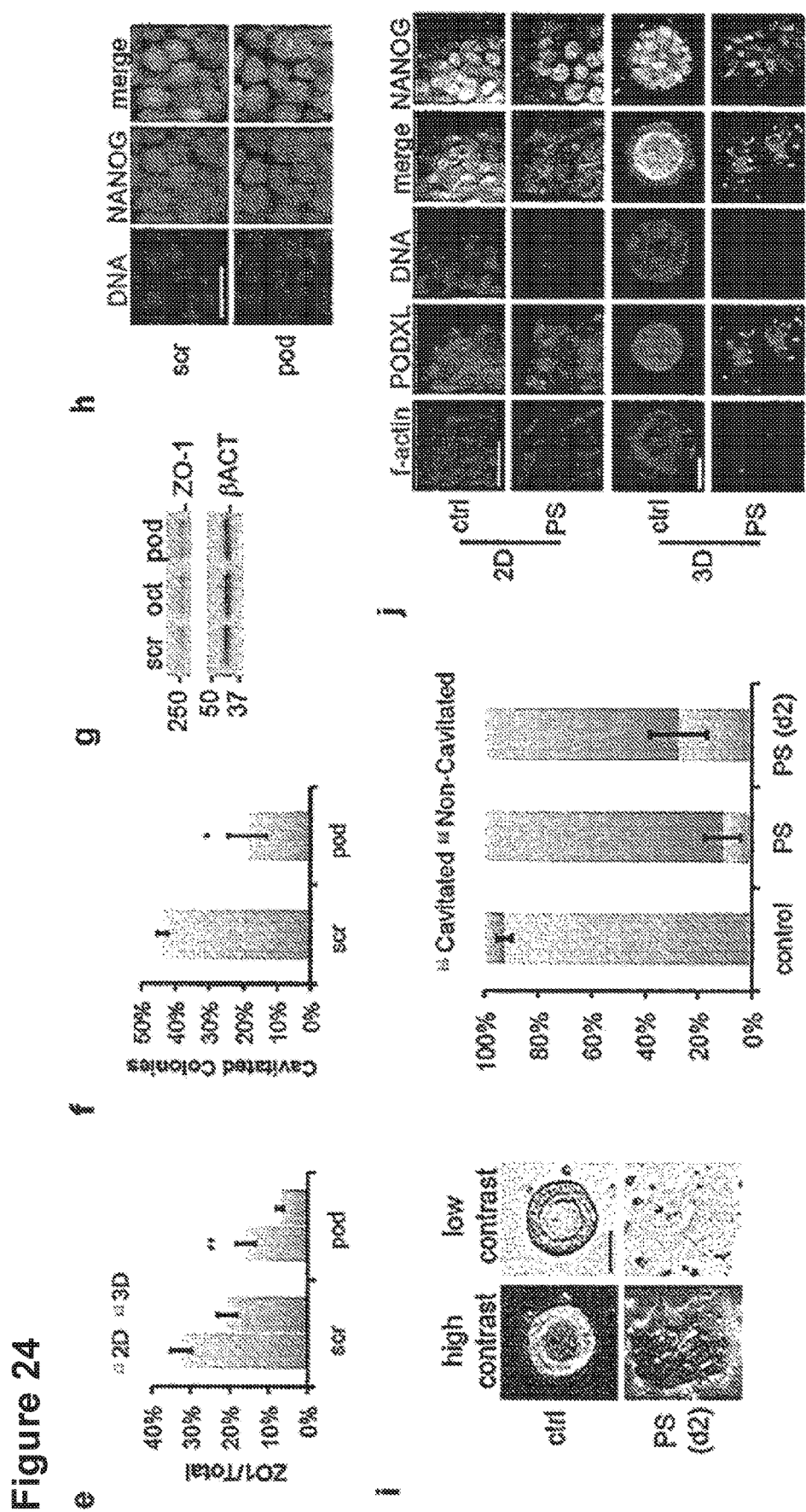

FIG. 24. Podocalyxin is dispensable for hPSC tight junction organization. (a) ZO-1, podocalyxin, and NANOG immunofluorescence images of CRISPR!Cas9 clones in 2D and 3D culture. A small lumen-like structure is observed in the PODXL-/- hPSC 3D aggregate (white dashed lines). (b) Representative images (left) and corresponding quantification (right) of wild-type or PODXL-/- spheroids after incubation with RD and LY for four hours. Line scans (bordered white rectangles in images) from outside to inside representing 25 wild-type or PODXL-/- spheroids pooled from ~2 hESC lines were averaged and plotted. (c) lmmunoblots (left) and corresponding band quantification (right) for PODXL, OCT4, and loading control (~ACT) in protein lysates from hPSCs transfected with siRNAs directed against PODXL (pod), OCT4 (oct), or a scrambled control sequence (scr). lmmunoblot intensities from hPSC lysates were normalized to their individual loading controls and averaged (n=2). (d) Immunofluorescence images and (e) colony surface area expressing ZO-1 of hPSCs transfected with these siRNAs and cultured under monolayer (2D) or sandwich (3D) conditions. (f) Percentage of colonies forming cavities with brightfield lumens. (g) lmmunoblots for ZO-1 in hPSCs subjected to siRNA with β-actin loading control. (h) Representative NANOG immunofluorescence in these cultures. Images are scaled identically. (i) Brightfield images (left) and quantification (right) of hPSCs treated with 8 µg/ml protamine sulfate from the time of sandwiching (PS), the day after sandwiching (PS d2), or untreated controls. (j) PODXL localization in hPSCs treated with PS. Scale bars, 50 µm.

Figure 25:
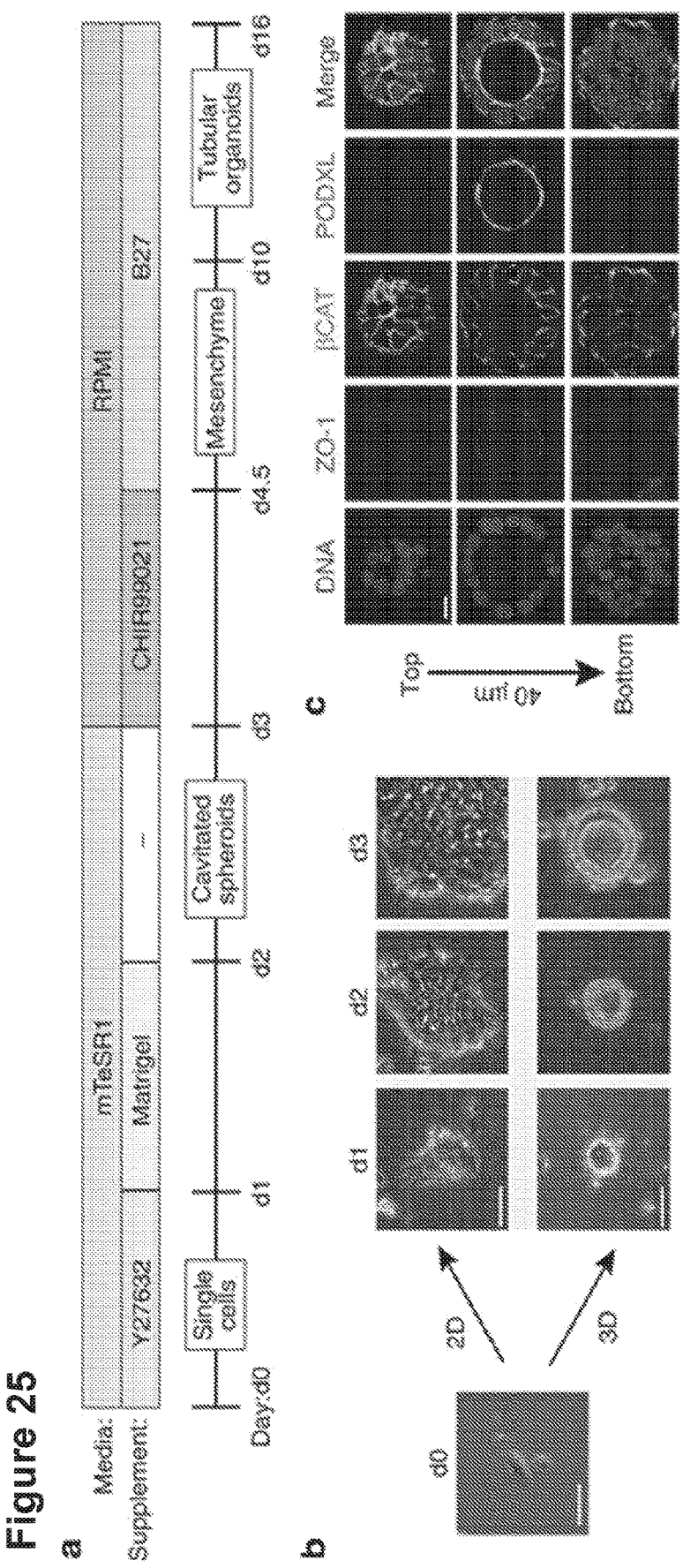
Figure 25:
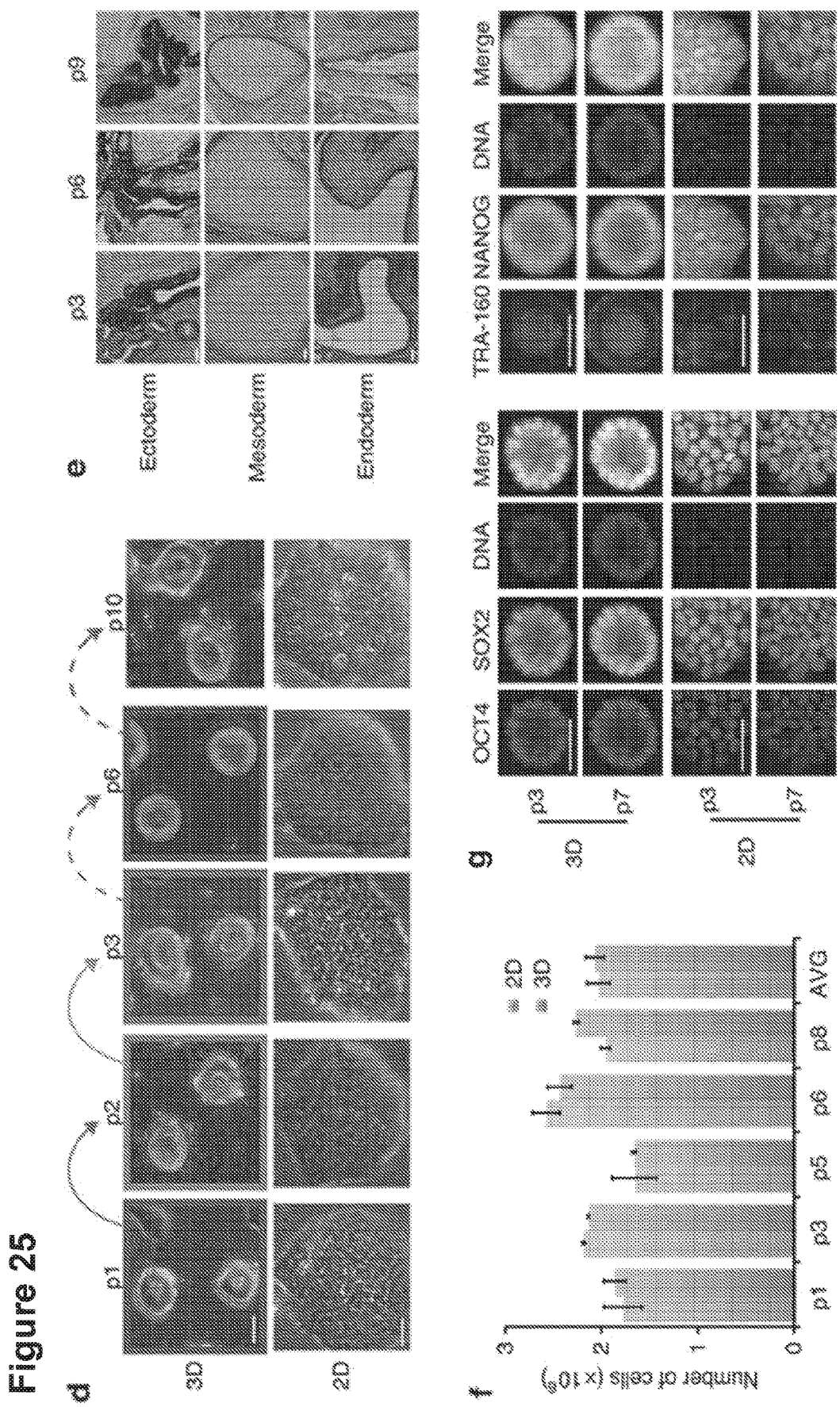

FIG. 25. hPSCs form cavitated spheroids in 3D culture. (a) Schematic of spheroid-to-organoid culture protocol. (b) Phase contrast images of ESCs in sandwich (3D) or monolayer (2D) cultures. Consecutive days are shown, with d0 indicating the time point immediately before sandwiching. (c) Confocal optical sections showing PODXL, ZO-1 and βCAT immunofluorescence through a representative spheroid with cavity. Vertical distance from top to bottom row is shown at left. (d) Representative brightfield images of hPSCs in 3D cultures that were dissociated (colored frames) and passaged (matching colored arrows). Dashed arrows represent serial passages in the 3D condition. Lower row shows cells plated into 2D cultures from dissociated spheroids from each passage. (e) Hematoxylin and eosin-stained sections of teratomas generated from hPSC serial 3D passages p3, p6 and p9 showing pigmented epithelium (ectoderm), cartilage (mesoderm) and glandular epithelium (endoderm). (f) Cell number (average of duplicate counts for each time point, or AVG of all five time points shown in the last column) in 2D and 3D cultures 72 h after plating. (g) Representative immunofluorescence images showing OCT4 and sex-determining region Y box-2 (SOX2) or tumor rejection antigen 1-60 (TRA-1-60) and NANOG localization in p3 and p7 serially sandwiched hPSCs. Scale bars, 100 µm. Error bars, s.e.m.

Figure 26:
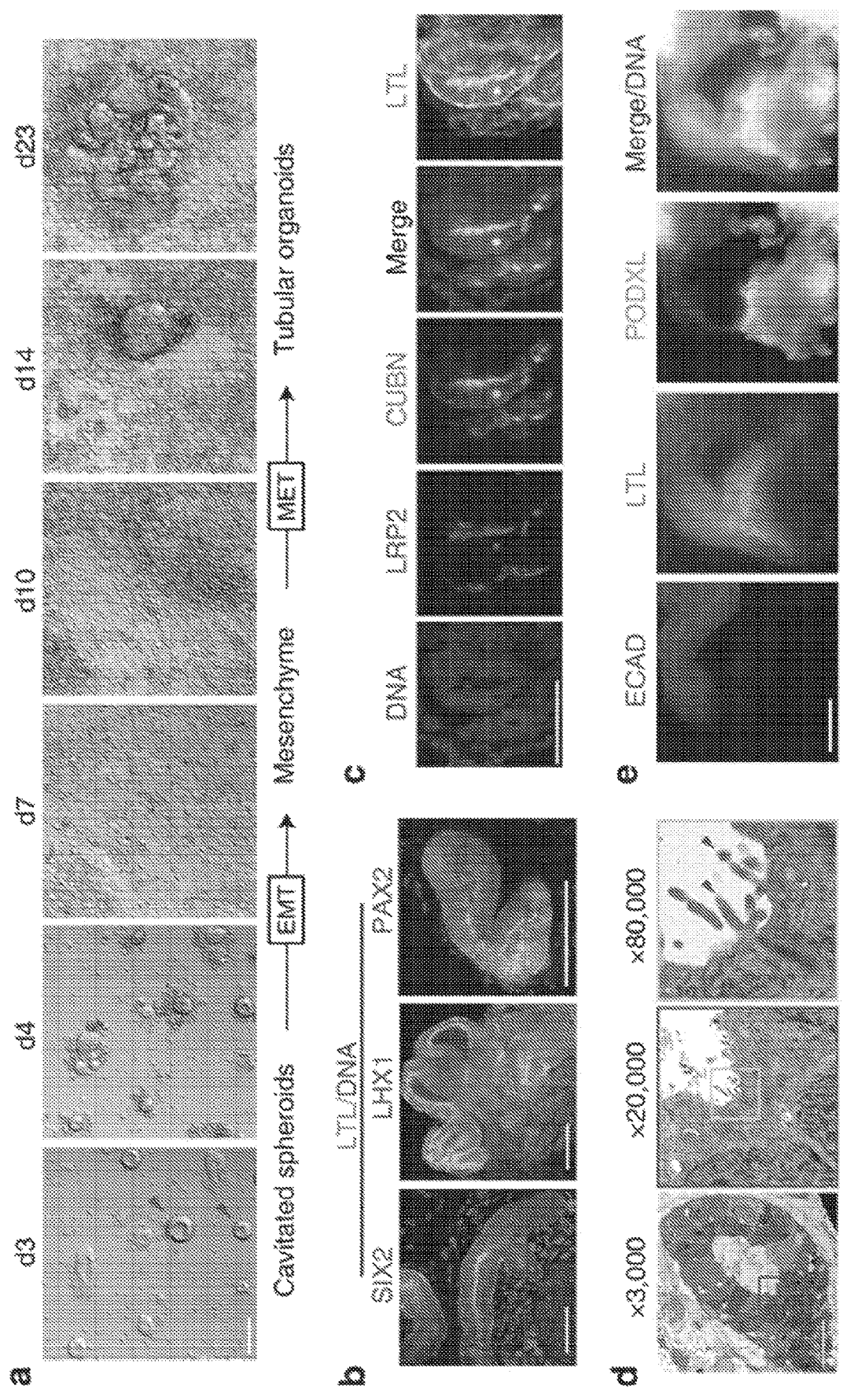
Figure 26:
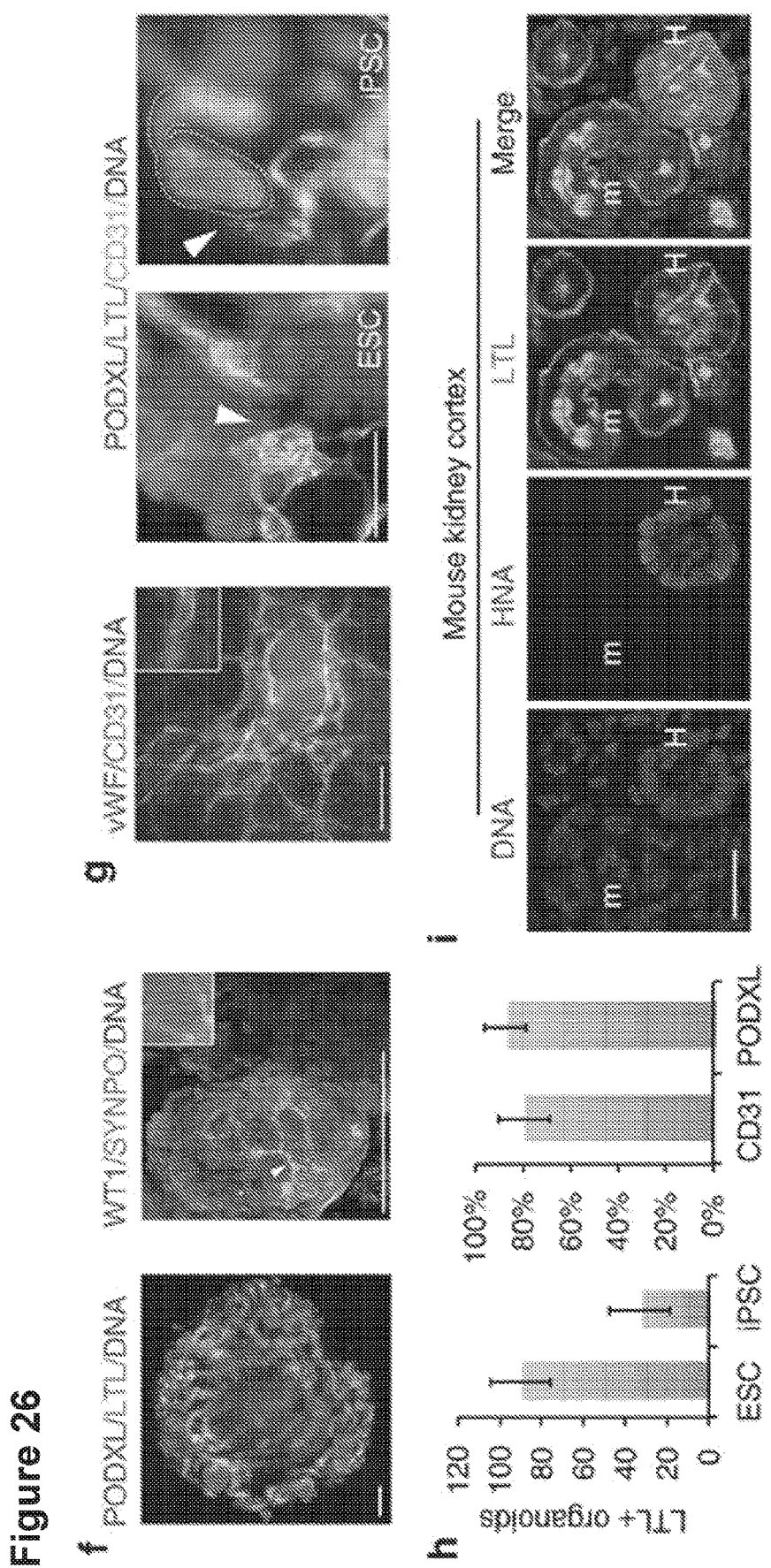

FIG. 26. Tubular organoids recapitulate kidney development and architecture. (a) Phase contrast images of spheroid differentiation into tubular organoids. Red arrowheads highlight epithelia. (b) Confocal optical sections showing LTL with nephron progenitor markers Sine oculis homeobox homologue 2 (SIX2), Lin11-Isl1-Mec3 (LIM) homeobox 1 (LHX1), paired box gene 2 (PAX2) and (c) proximal tubule markers low density lipoprotein-related protein 2/megalin and cubilin in tubular organoids. (d) Electron micrographs of a representative tubule, with progressive magnifications of regions in colored boxes highlighting apical microvilli (arrowheads) and tight junctions (arrows). (e) Wide-field images showing tubule anatomical progression from E-cadherin (ECAD)$^+$ to LTL$^-$ to PODXL$^+$ organoid segments. (f) Low-magnification image of organoid with interlacing tubules and peripheral PODXL$^+$ aggregates (left) and high-magnification confocal optical section showing co-localization of synaptopodin (SYNPO) and Wilms tumour protein (WT1) in organoid podocyte-like cells (right). (g) Wide-field immunofluorescence showing co-localization of CD31 with von Willebrand factor (vWF, left), or with nephron markers in tubular organoids derived from hESCs and iPSCs (right). White arrowheads show interactions between tubular, podocyte-like and endothelial compartments. White dashed outline highlights a representative tubular terminus. Images are representative of one hESC line and three iPSC lines from different patients. (h) Number of tubular organoids formed per unit surface area in cultures of hESCs and iPSCs (left) and percent of these LTL$^+$ organoids associated with CD31$^+$ and PODXL$^+$ cell types within the organoid (right). (1) Confocal images of organoid-derived human tubule (H) with LTL reactivity after 3 weeks of growth inside the developing mouse kidney cortex (m). Scale bars, 100 Error bars, s.e.m (n>3 experiments).

Figure 27:
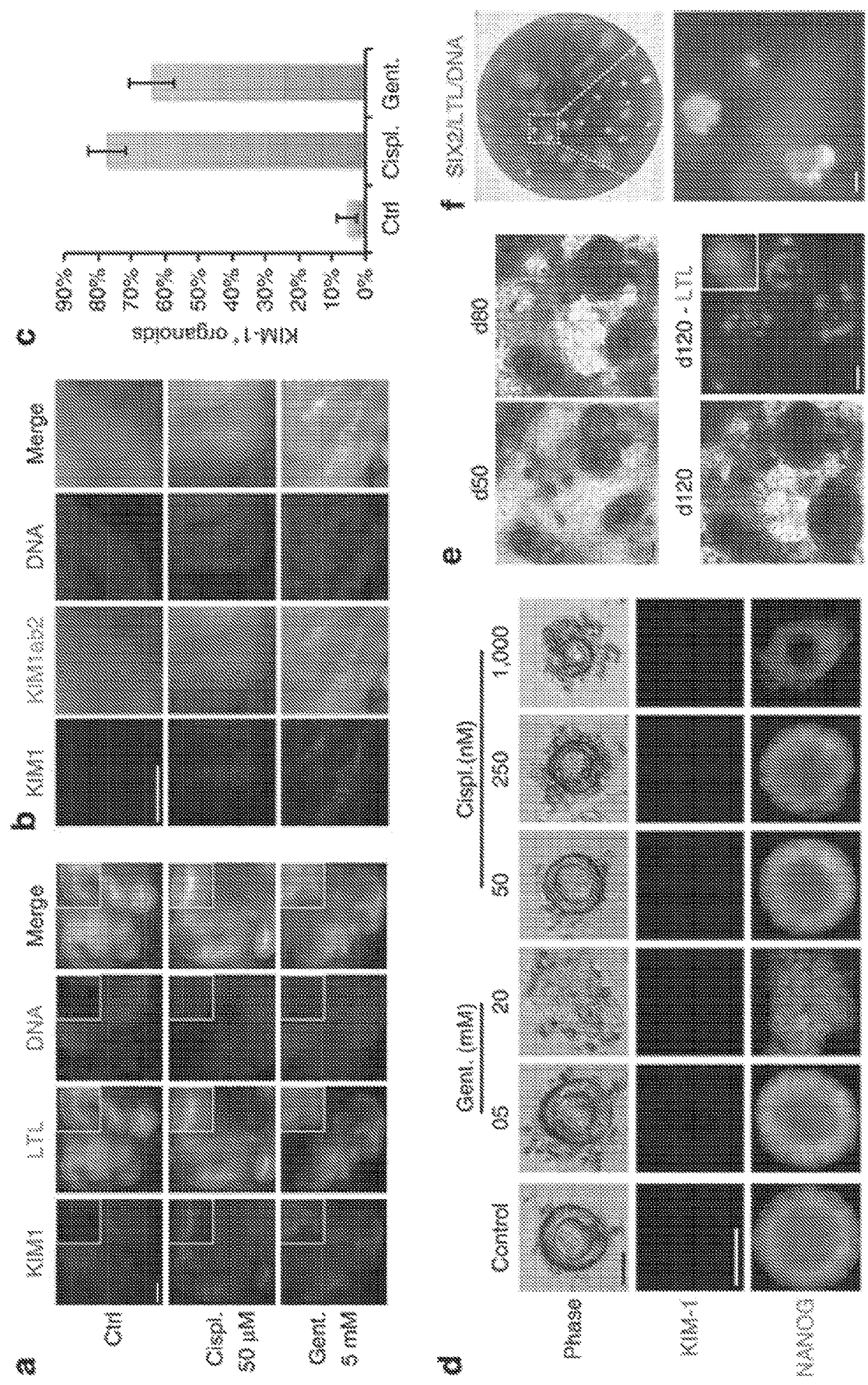

FIG. 27. Tubular organoids create a microphysiological model for kidney nephrotoxicity studies. (a) Co-localization of KIM-1 antibody AKG7 with LTL or (b) with a second KIM-1 antibody (KIMlab2). (c) Quantification of organoids expressing KIM-1 after treatment with 50 μM cisplatin (Cispl.) or 5 mM gentamicin (Gent.), compared with vehicle-treated controls (n=3/condition, >50 organoids/experiment). (d) Phase contrast of living cells, or KIM-1 and NANOG immunofluorescence, in epiblast spheroids treated with titrations of cisplatin and gentamicin. No KIM-1 expression is observed at any dose including 5 mM gentamicin, a concentration sufficient to induce KIM-1 upregulation in kidney organoids. Cisplatin was toxic to spheroids at concentrations>1 μM. (e) Phase contrast time course of tubules in culture. After 120 days of culture (d120), tubules were fixed and stained for LTL. (f) Whole well of a 96-well plate showing kidney organoids. Scale bars, 50 μm. Error bars, s.e.m.

Figure 28:
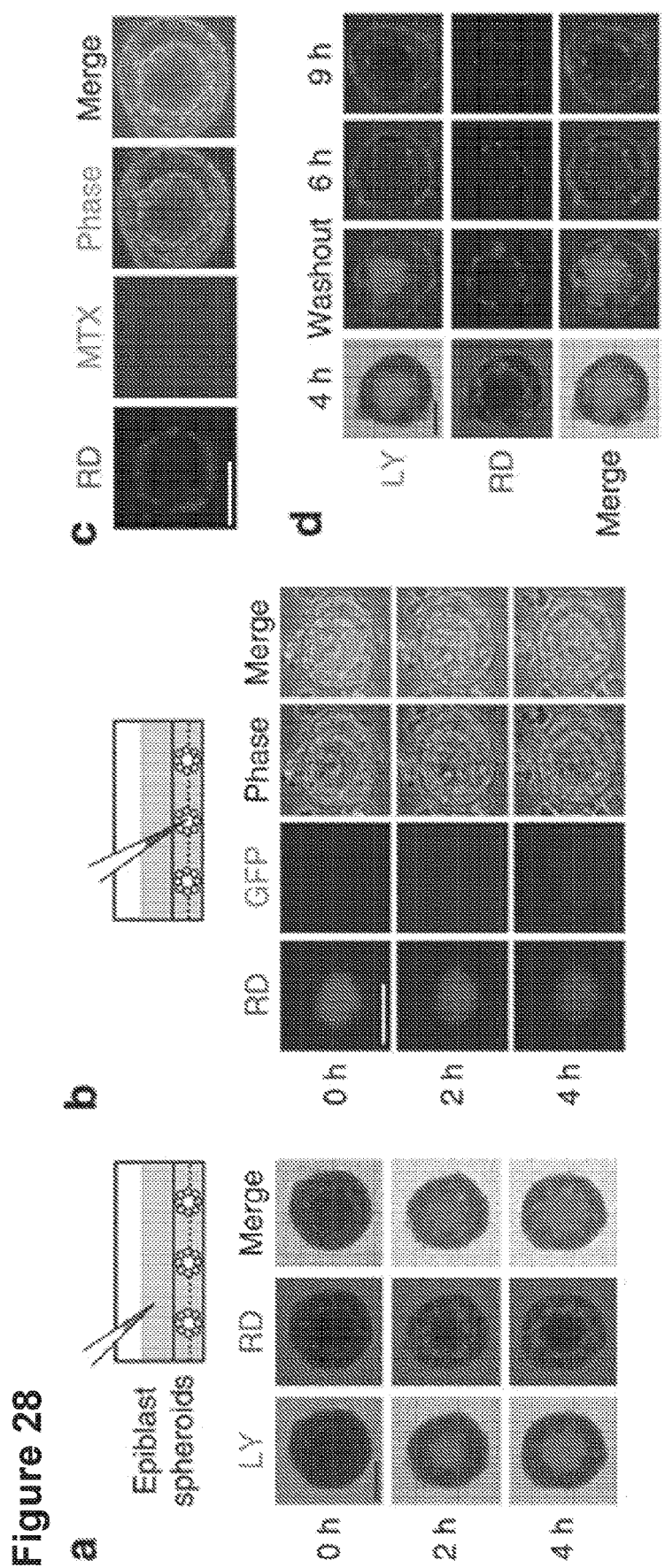
Figure 28:
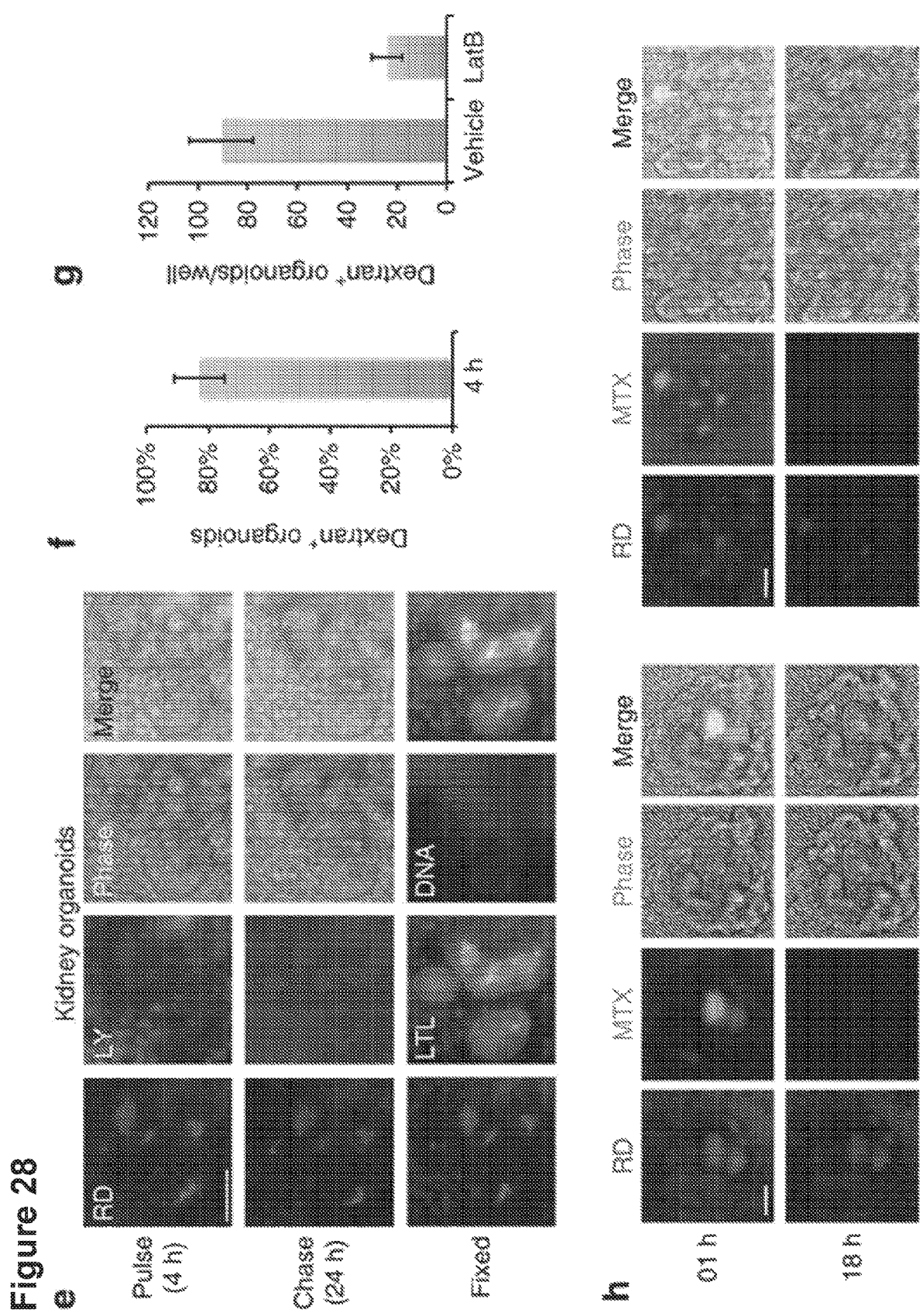

FIG. 28. Differential accumulation of fluorescent cargoes in epiblast spheroids versus kidney organoid tubules. (a) Experimental schematic and confocal time-lapse images showing hPSC spheroids incubated with Lucifer yellow™ (LY) and rhodamine-conjugated dextran (RD). (b) Experimental schematic and wide-field time course of an hPSC spheroid cavity after microinjection with RD. No autofluorescence is detected (green fluorescent protein channel). (c) An hPSC spheroid treated with fluorescein methotrexate for 4 h, immediately after washout. (d) Time course of an hPSC spheroid incubated with LY or RD molecular dyes for 4 h, after which the media was replaced without dyes (washout). (e) Representative time course of a tubular organoid incubated with RD and LY for 4 h (pulse), followed by incubation in fresh media without dyes (chase), fixation and co-localization with LTL. (f, g) Quantification of tubular organoids that accumulated RD, with or without 2 μM Latrunculin B (n=3). (h) Fluorescein methotrexate and RD distributions in two representative live organoids 1 h and 18 h after washout. Scale bars, 50 μm (a-d) or 100 μm (e-h). Error bars, s.e.m.

Figure 29:
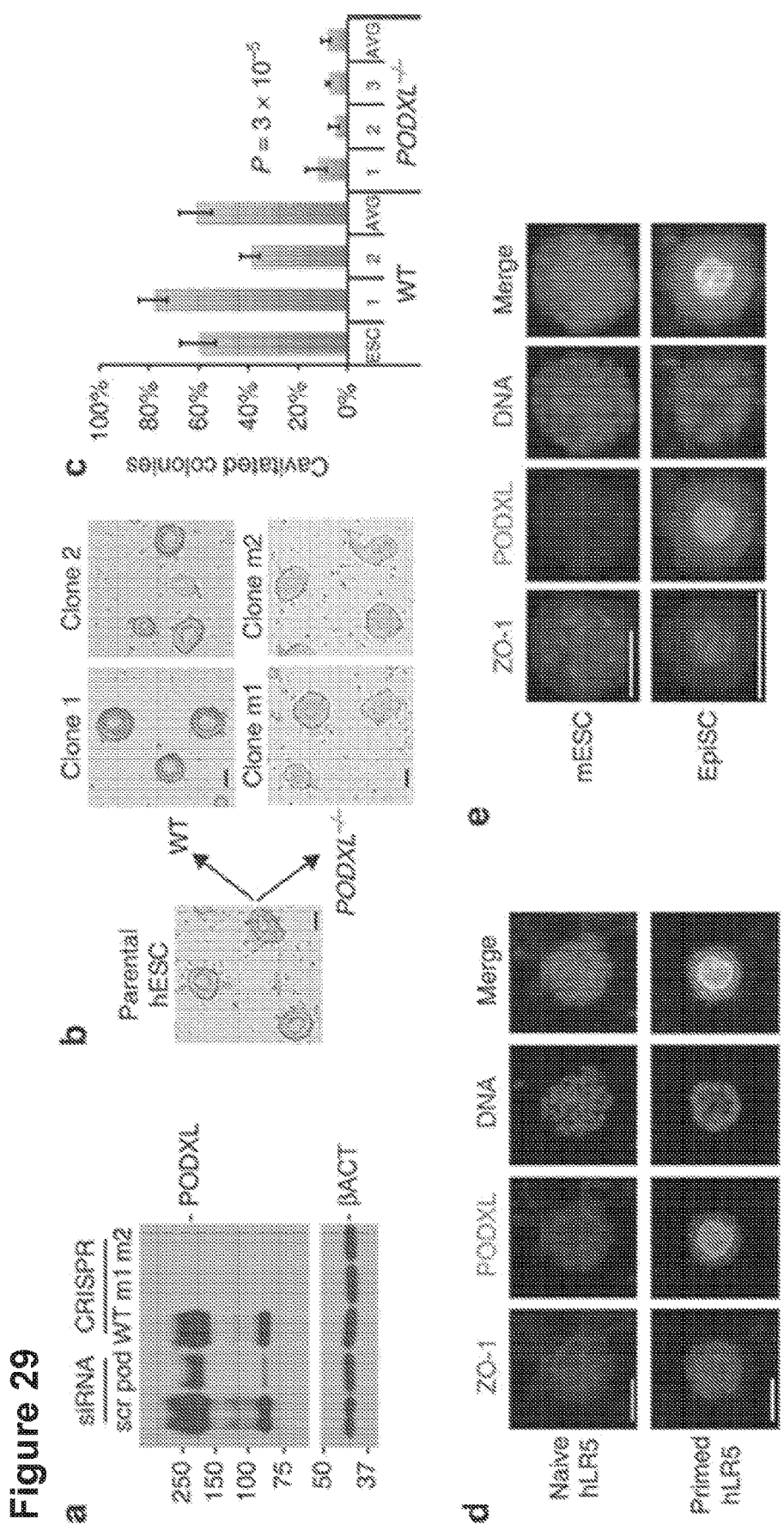
Figure 29:
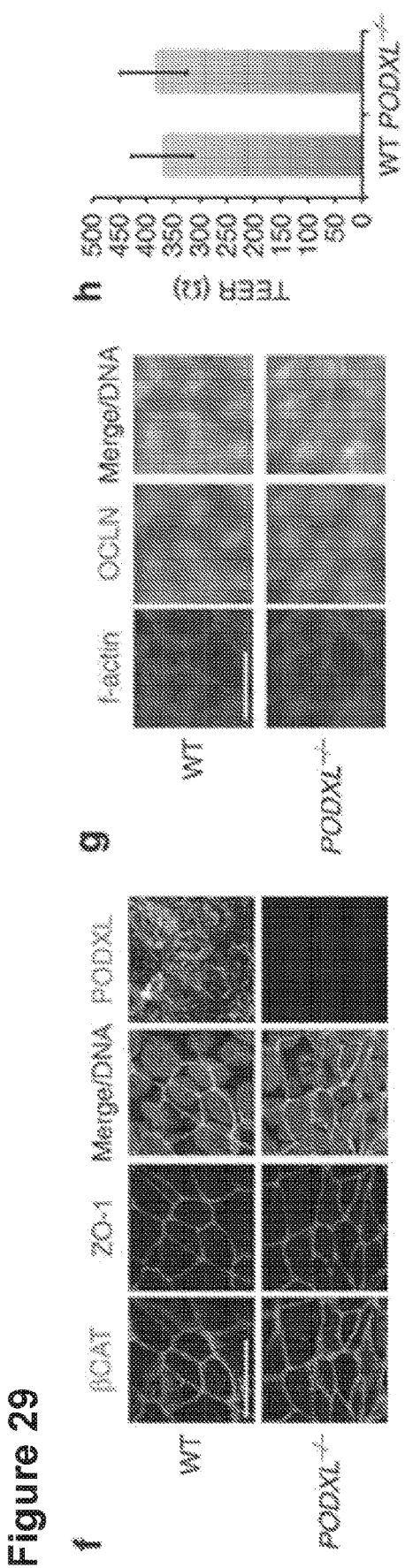

FIG. 29. Podocalyxin promotes lumenogenesis in epiblast spheroids. (a) Immunoblot for podocalyxin protein in two representative PODXL$^{-/-}$ hPSC mutant clones (m1 and m2), compared with CRISPR/Cas9 non-mutant wild-type clones (WT) or cells subjected to scrambled (scr) or podocalyxin (pod) siRNA knockdown. (b) Brightfield images of sandwiched parental ESCs were compared with two mutant or two WT CRISPR/Cas9 clones. (c) Cavitated spheroids as a percentage of total colonies. Data from pools of WT or mutant cell lines were averaged to determine group means (AVG, n≥9) and P values. (d) Podocalyxin and ZO-1 immunofluorescence in naive and primed hLR5 hPSCs or (e) mESCs and EpiSCs. (f) Confocal z-sections of undifferentiated hPSCs showing localization of ZO-1 and βCAT in unmodified (WT) or PODXL$^{-/-}$ colonies. (g) Filamentous actin (f-actin) and occludin (OCLN) immunofluorescence in undifferentiated WT or PODXL$^{-/-}$ clones. (h) Averaged TEER measurements in WT or PODXL$^{-/-}$ monolayers (n≥3). Scale bars, 50 μm or (f, g) 20 μm. Error bars, s.e.m.

Figure 30:
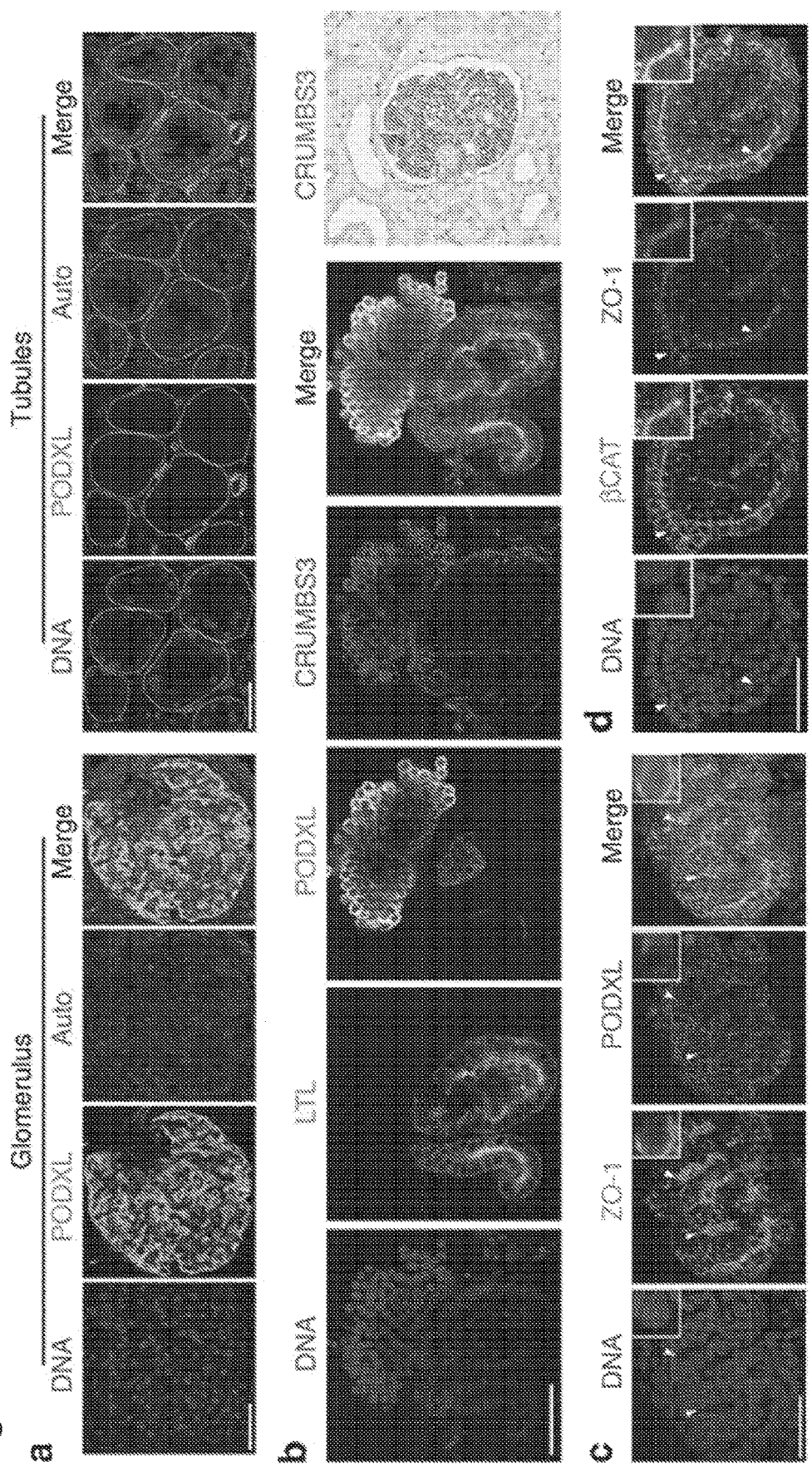
Figure 30:
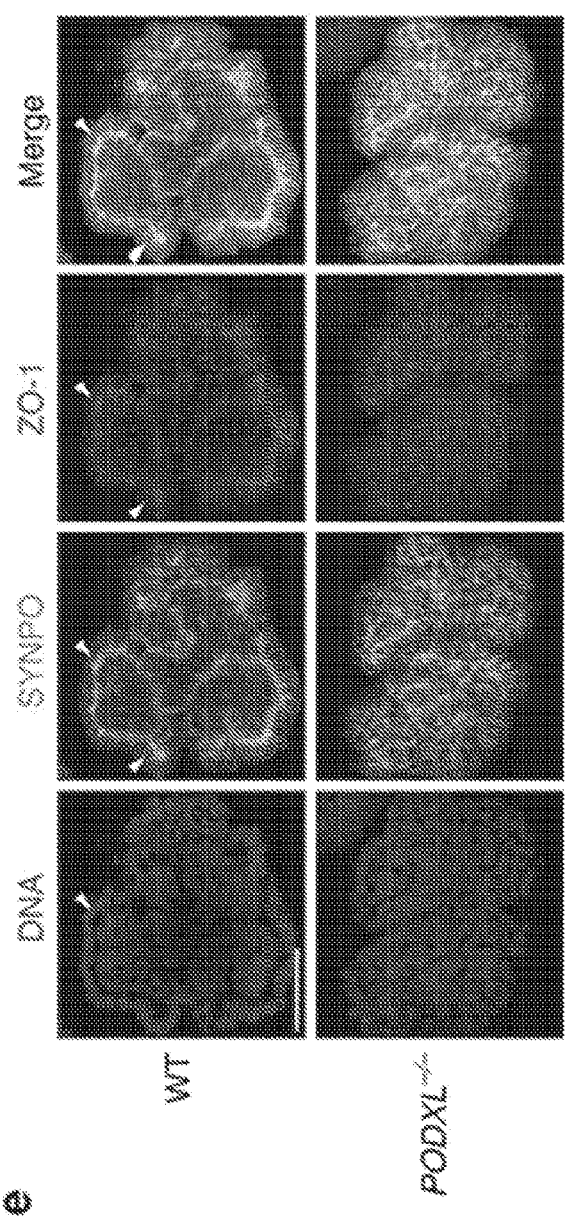
Figure 30:
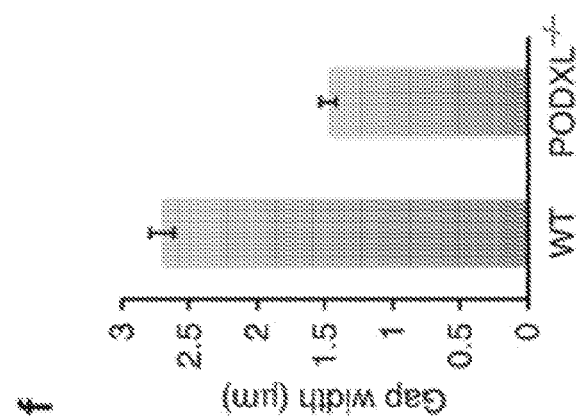

FIG. 30. Junctional complexes are disrupted in hPSC-derived PODXL$^{-/-}$ podocyte-like cells. (a) Confocal optical section of adult human kidney. Podocalyxin is expressed in podocytes and peritubular capillaries, but is absent from tubules (white dotted lines). Auto, autofluorescence. (b) Crumbs3 expression in hPSC-derived kidney organoids (confocal red channel) and human kidney tissue (far right panel, immunohistochemistry). (c) Confocal optical sections showing distributions of ZO-1 with podocalyxin or (d) βCAT in hPSC-derived podocyte-like cell clusters. Arrowheads highlight tracks of junctional complexes between podocyte-like cells. (e) Confocal sections of wild-type or PODXL$^{-/-}$ podocyte-like cell clusters in tubular organoids. (f) Gap widths between adjacent podocyte-like cell nuclei in these cell lines (n≥100 gaps pooled from two experiments). Scale bars, 50 μm. Error bars, s.e.m.

Figure 31:
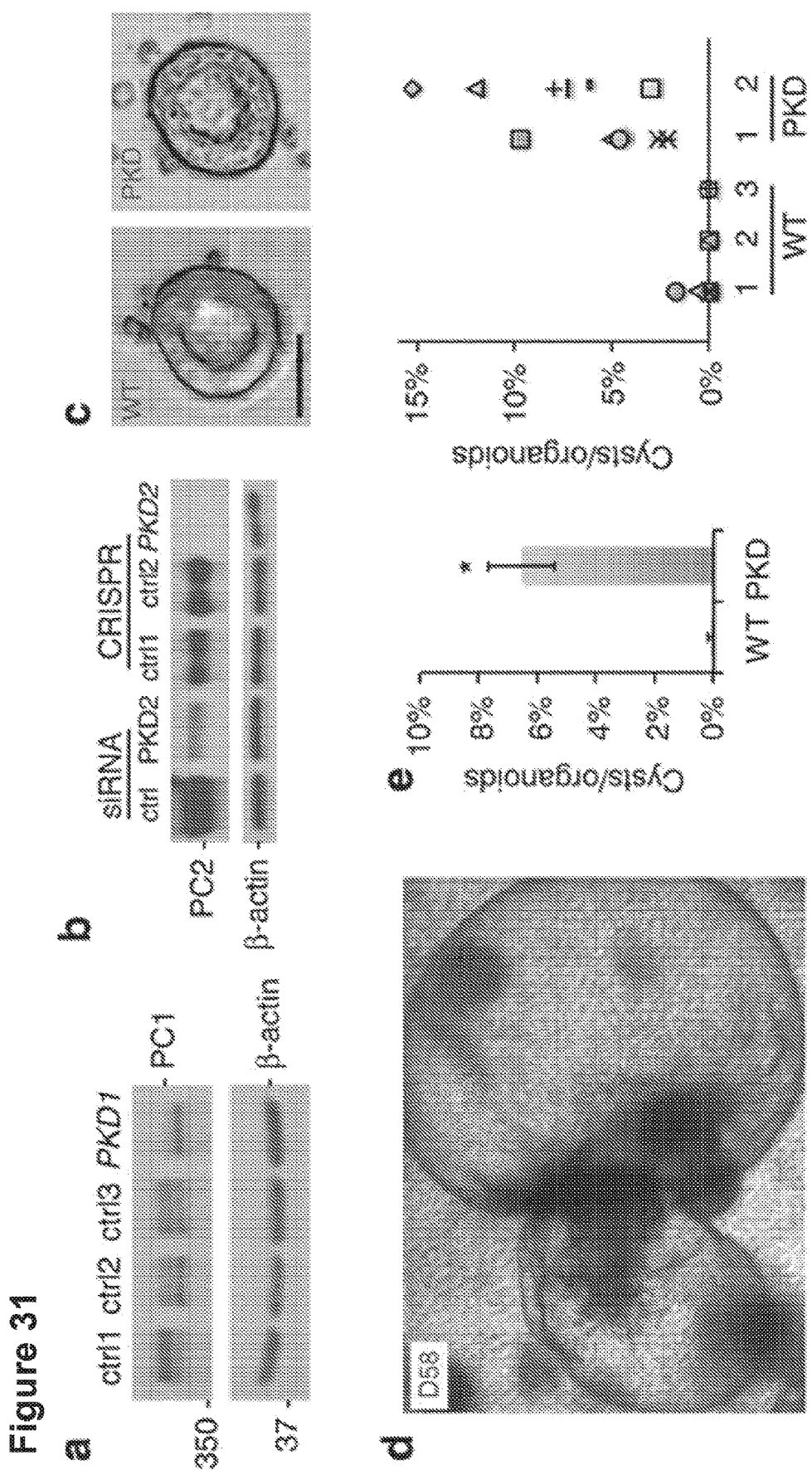
Figure 31:
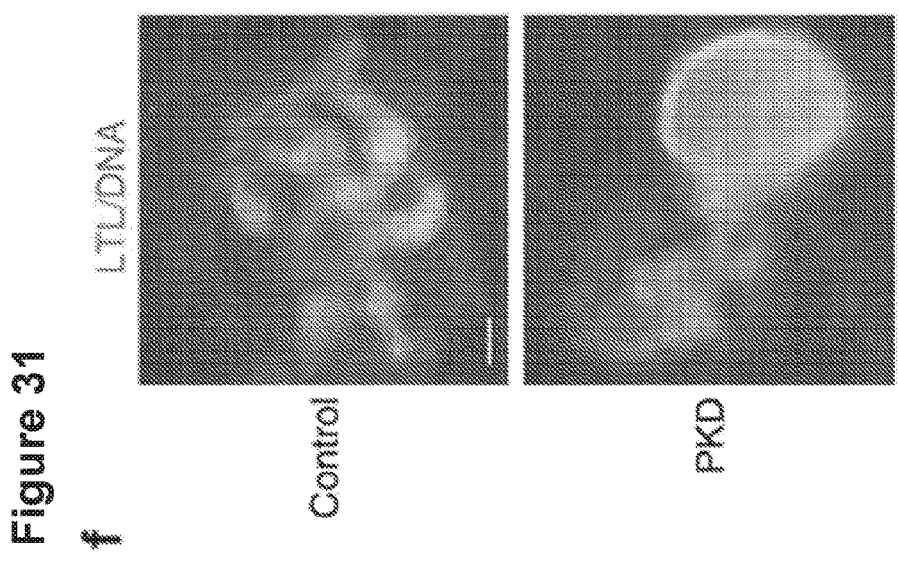
Figure 31:
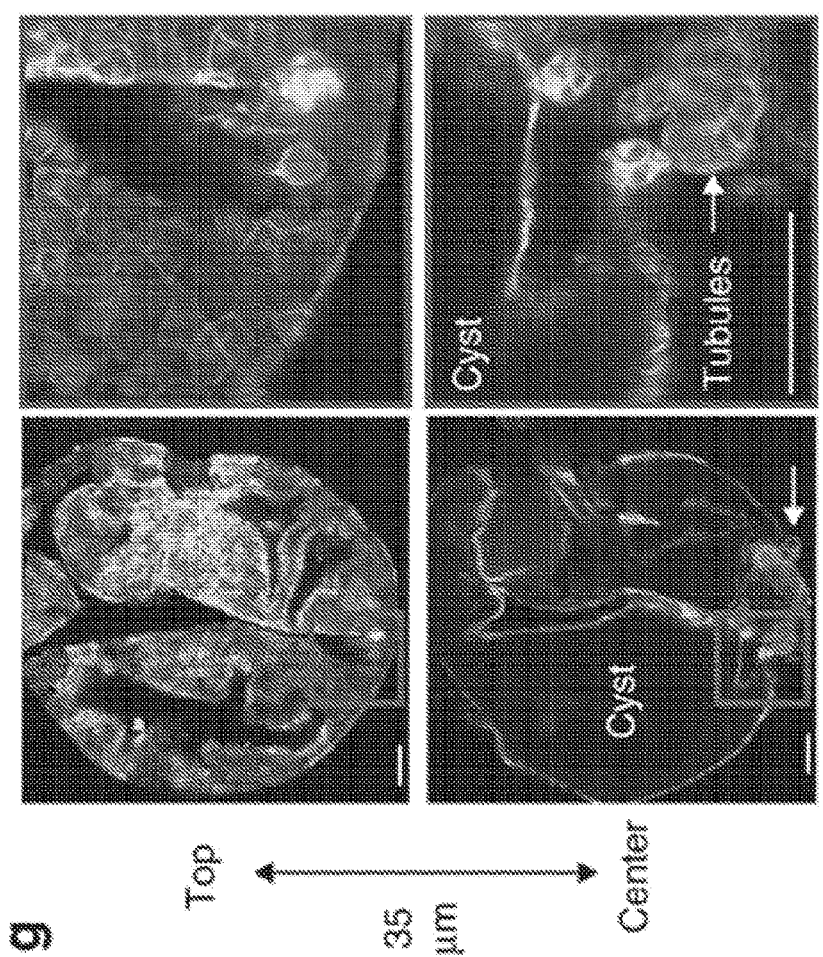

FIG. 31. PKD hPSCs model lineage-specific cyst formation. (a) Immunoblots showing reduction in full-length polycystin-1 (PC1) in CRISPR-generated PKDI hPSCs or (b) polycystin-2 (PC2) in PKD2$^{-/-}$ hPSCs, compared with isogenic controls. PKD2 knockdown is shown for comparison. (c) Epiblast spheroid morphology in representative PKD knockout hPSCs and controls. (d) Representative cyst on day 58 of culture in PKD2 kidney organoids. (e) Quantification of cyst formation rate in PKD knockout organoids and isogenic WT controls as an average of all experiments (n>10) or as scatter plots of individual experiments. (f) Wide-field epifluorescence images and (g) confocal optical sections showing LTL reactivity in cysts. Representative z-sections show hollow center of cyst and associated tubular organoid (arrow). Zoom is shown of red boxed regions. Scale bars, 100 μm. Error bars, s.e.m. *P<0.01.

Figure 32:
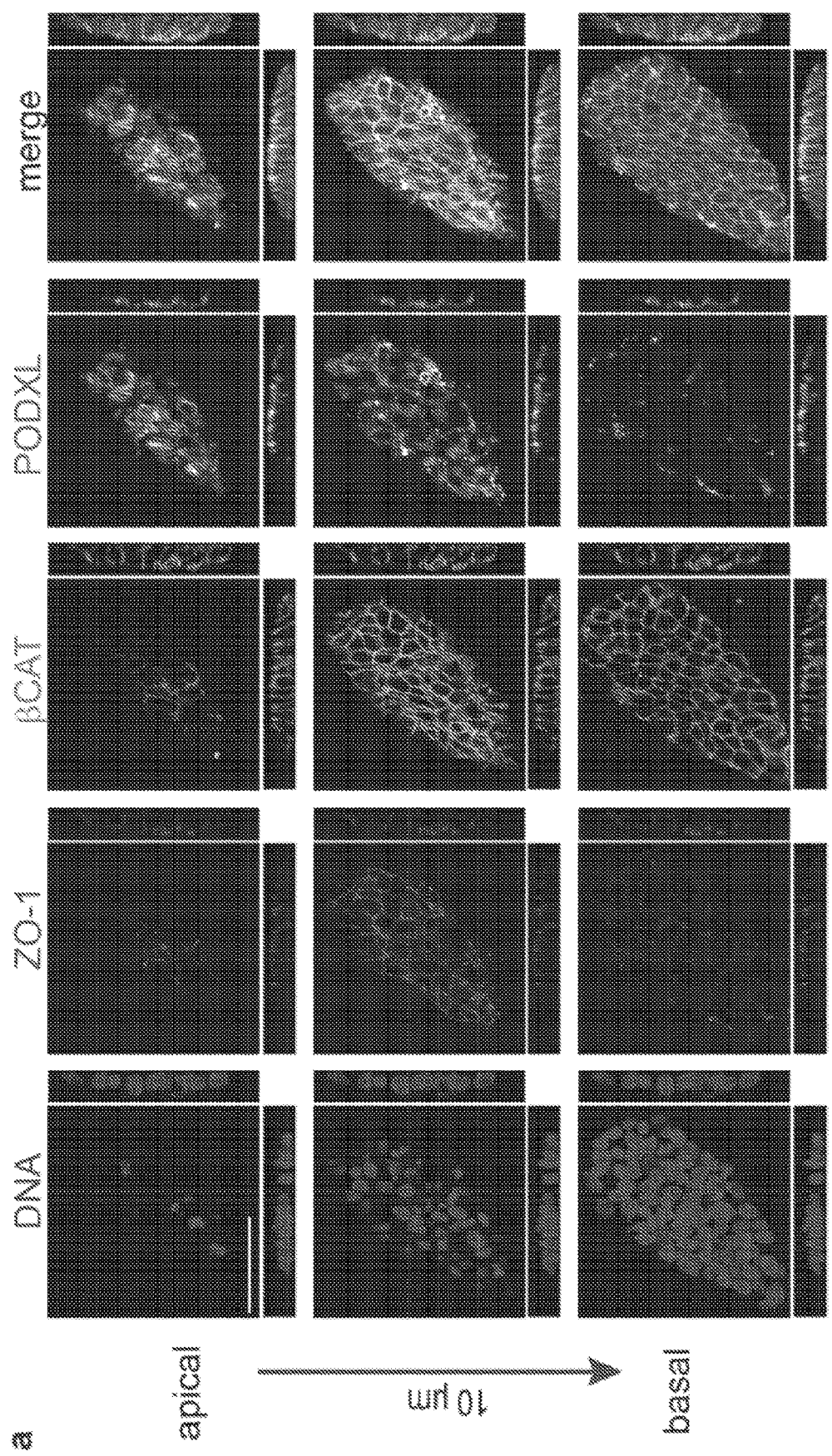

FIG. 32. Spheroids resemble monolayer hPSCs. (a) Confocal z-stack showing podocalyxin, ZO-1, and β-catenin immunofluorescence through a representative hPSC monolayer colony. Three optical sections through a single colony are shown, from the apical side to the basal side. Podocalyxin is the most apical marker, as shown in the most apical optical section, where it can be seen even in areas of the colony where ZO-1 is not evident. In the middle optical section, ZO-1 appears in a cobblestone pattern at cell-cell contact points. In the most basolateral section, only β-catenin is visible. The sections are accompanied by orthogonal 3D reconstructions of the entire z-stack, which show that ZO-1 is strongly concentrated at areas of cell-cell contact. Vertical distance from top to bottom row is shown at left. (b) Schematic of RNA-Seq experiment and resultant hierarchical clustering of hPSCs in 2D monolayers and 3D spheroids. Two lines are shown (A and B) on two different dates (−1 and −2). Samples in the plot are arranged according to highest correlation as further demonstrated by the dendrogram on the right side. The heatmap grid demonstrates the extent of correlation and is composed of the corresponding RA2 values. Colored boxes in dendrogram match groupings in schematic. Scale bars, 50 μm.

Figure 33:
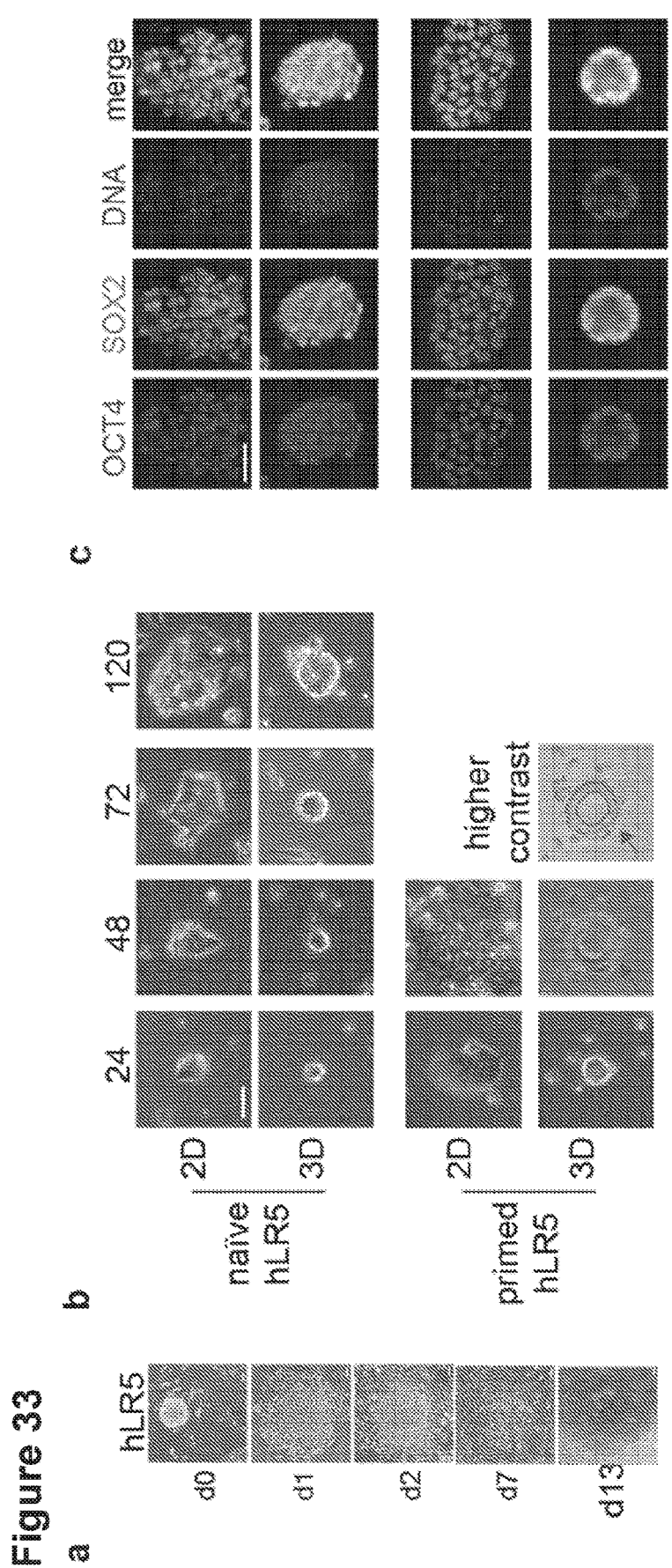
Figure 33:
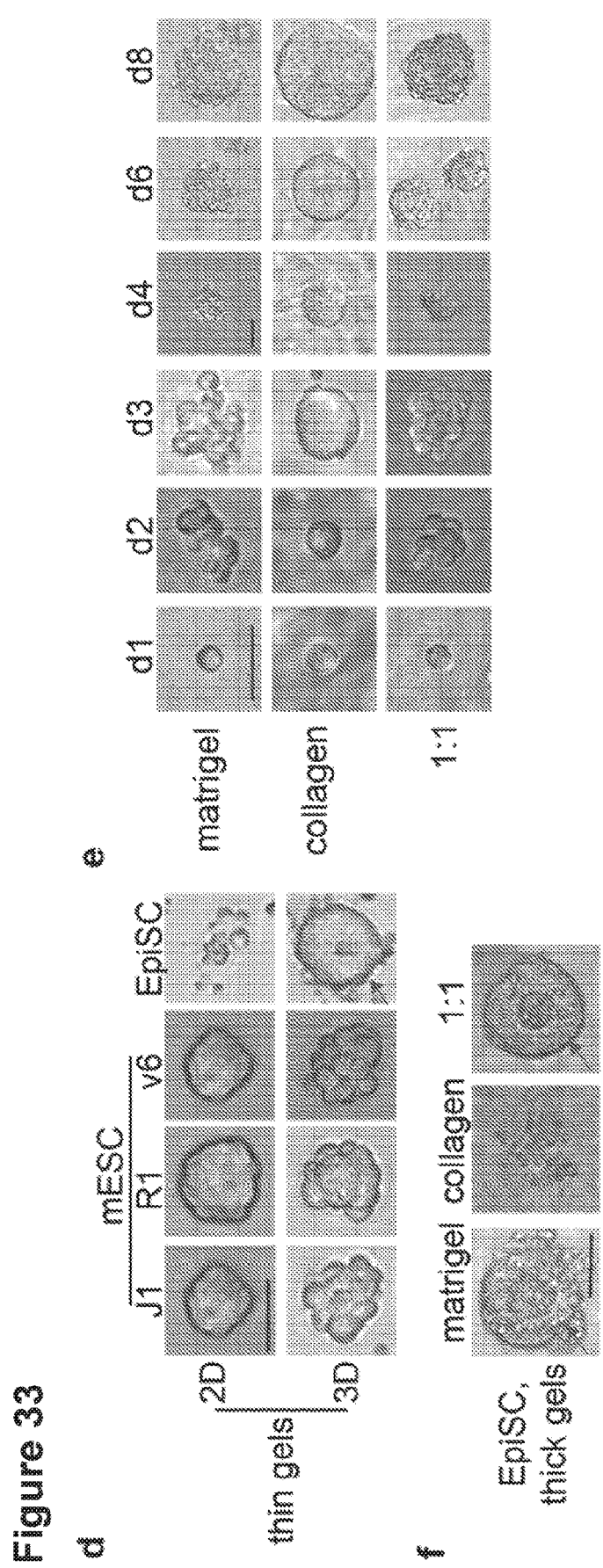

FIG. 33. Cavity formation is restricted to the epiblast stage. (a) Time course showing transition of naïve hLR5 iPSCs to primed LO-hLR5. (b) naïve and primed hLR5 morphologies in 2D and 3D cultures. (c) OCT4 and SOX2 immunofluorescence in naïve and primed hLR5 iPSCs. (d) Brightfield morphology of mESCs (lines J1, R1, and v6) or EpiSCs in thin gels 48 hours after sandwiching. Red arrows indicate structures initiating lumenogenesis. Time points (24, 48, etc) represent hours after sandwiching and show different colonies. (e) mESC colonies grown from single cells in thick gels of either 100% MATRIGEL™, 100% buffered collagen, or a 1:1 mixture of the two (1:1). Similar results were obtained from three separate mESC lines. (f) Mouse EpiSCs in thick gels 120 hours after plating. Scale bars, 50 μm.

Figure 34:
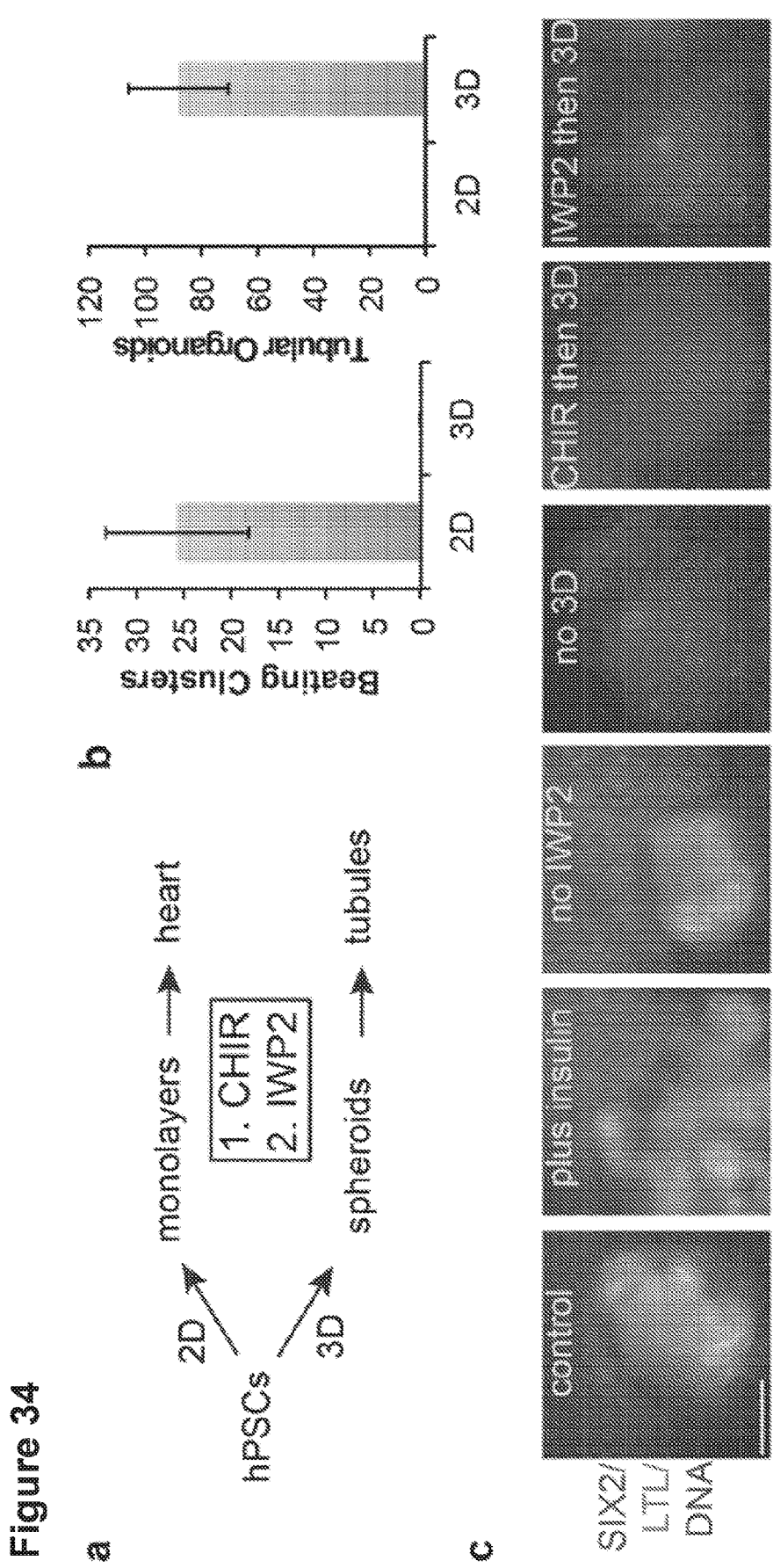
Figure 34:
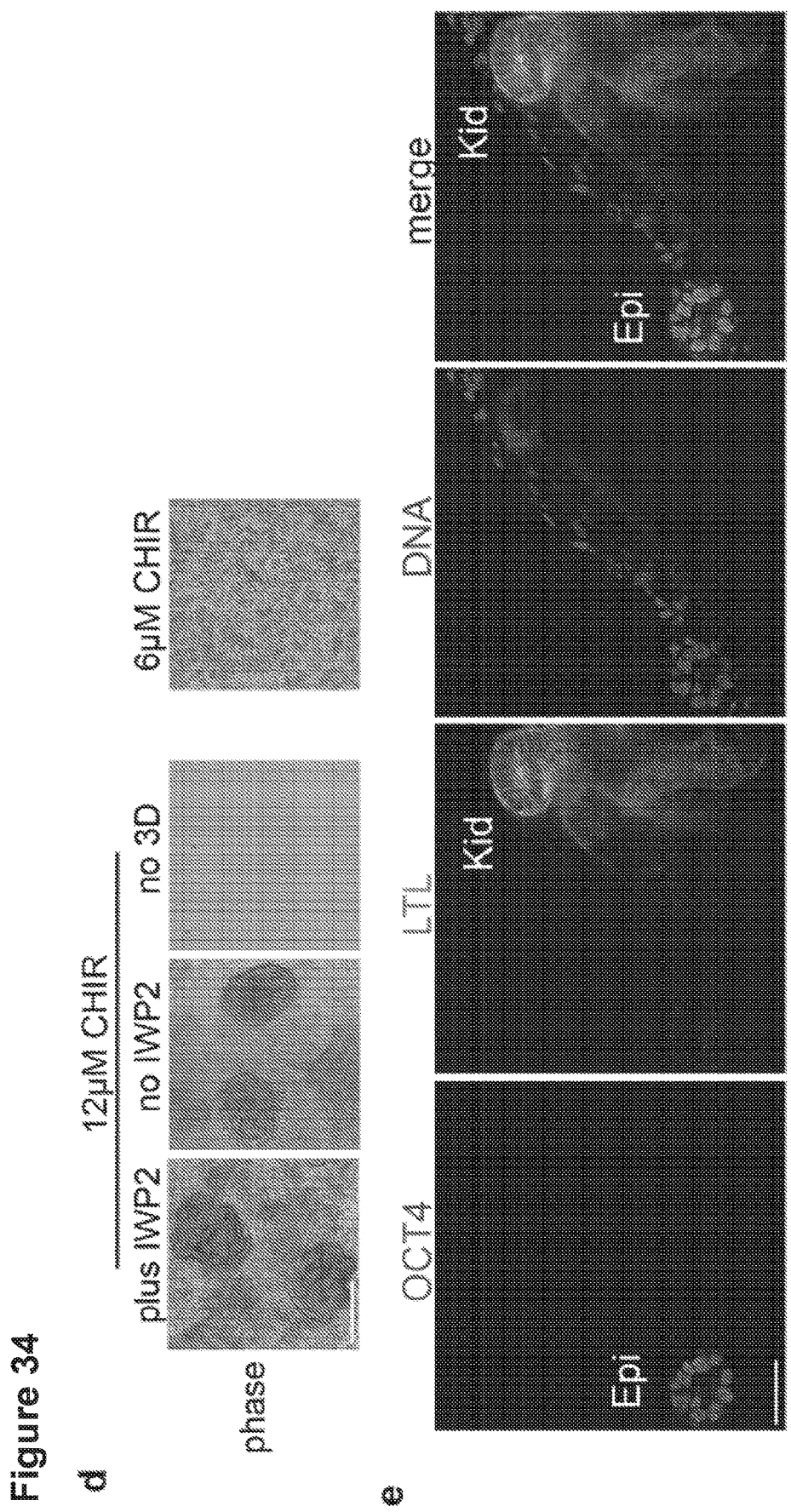
Figure 35:
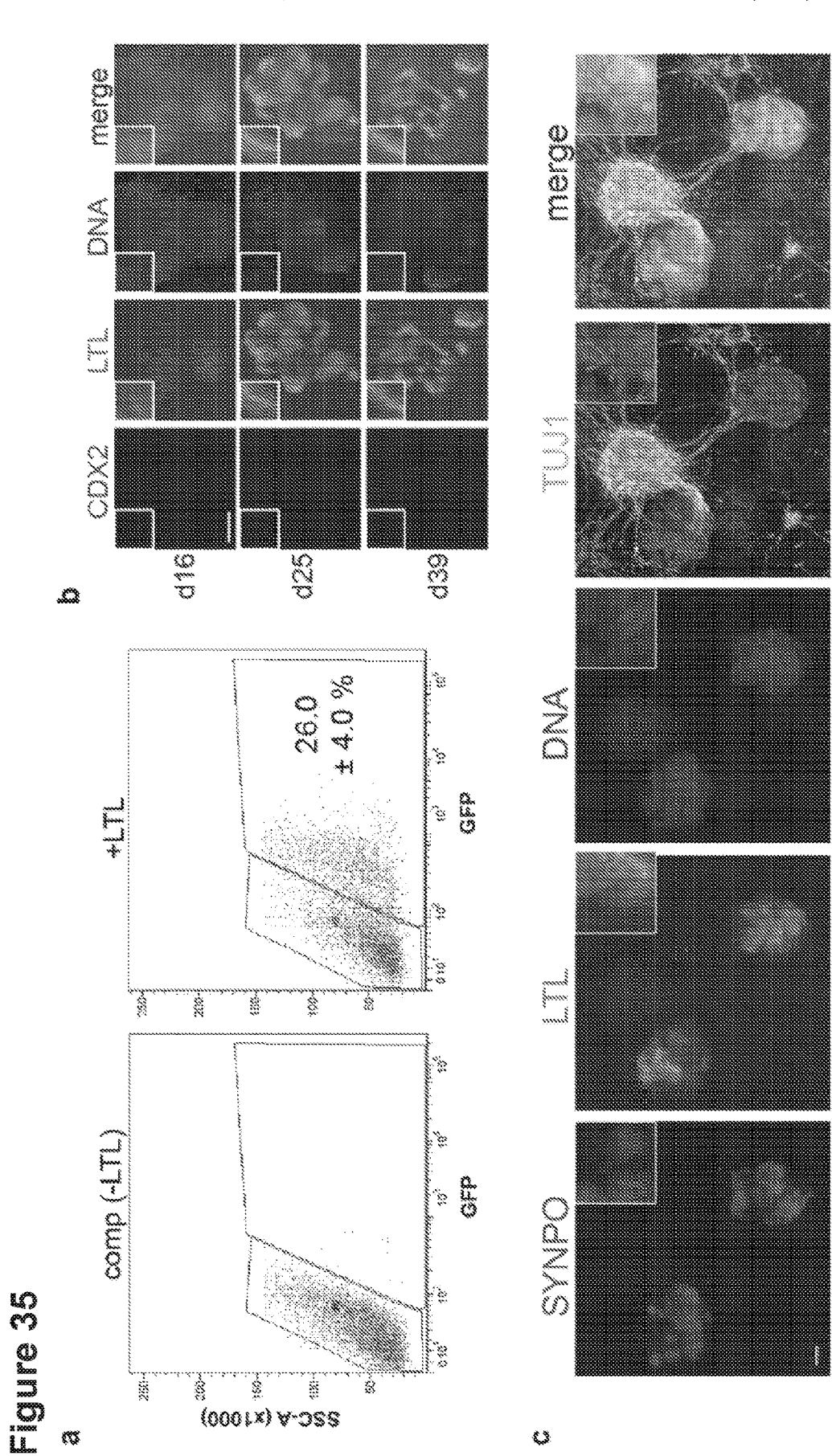
Figure 35:
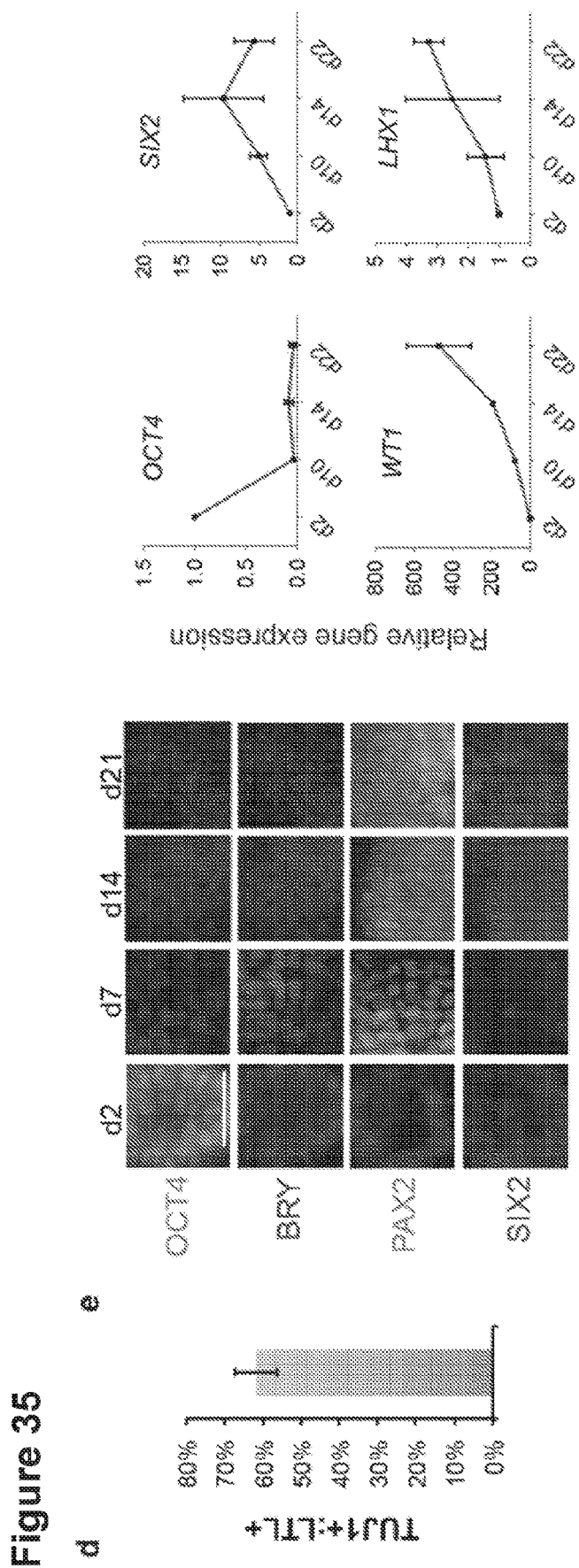

FIG. 34. Generation of kidney-like tubular organoids in 3D cultures. (a) Schematic of original 2D cardiomyocyte differentiation protocol and application to 3D spheroids. (b) Quantification of beating cardiomyocytes and tubular organoids produced in 2D and 3D cultures treated identically with this protocol. (c) Day 22 structures representing identically-plated hPSC spheroids treated with the described cardiomyocyte differentiation protocol with the following variations (from left): original protocol (control), use of 827 supplement including insulin, no IWP2 treatment, no sandwiching, sandwiching after CHIR treatment, sandwiching after IWP2 treatment. (d) Day 22 structures representing identically-plated cultures treated with CHIR in RPMI with the labeled variations. (e) Confocal optical section showing co-localization of OCT4 and LTL in epiblast spheroid (Epi) and kidney organoid (Kid) co-culture. Kidney organoids were picked, transferred to cultures of spheroids from the same iPSC line, and allowed to adhere overnight before fixation and processing for immunofluorescence. Error bars, s.e.m. (n≥3 separate experiments). Scale bars, 100 μm FIG. 35. Kidney organoid differentiation. (a) Flow cytometry analysis of LTL binding in kidney organoid cells as a percentage of the population. Identically-plated wells of kidney organoids were incubated with LTL or without LTL as a compensation control (camp). Cells were then dissociated and subjected to flow cytometry. The percentage of all cells that were LTL+by FACS is shown (averaged from 3 separate experiments). (b) Time course in organoid cultures (rows indicate days of culture) showing absence of L TL co-staining with the intestinal marker CDX2. (c) Wide-field low-resolution images showing neural (TUJ1+) clusters and kidney (LTL+) organoids in these cultures. (d) Ratio of neural clusters to kidney organoids. (e) Immunofluorescence and quantitative RT-PCR time courses sequential expression of stage-specific developmental markers for pluripotency (OCT4), primitive streak (BRY), intermediate mesoderm (PAX2), nephron progenitor (PAX2, SIX2, LHX1, WT1), and podocytes (WT1). d2 represents epiblast spheroids on day 2 after sandwiching, just before CHIR treatment. Error bars, s.e.m. (n≥3 separate experiments and ~30 organoids examined per experiment).

Figure 36:
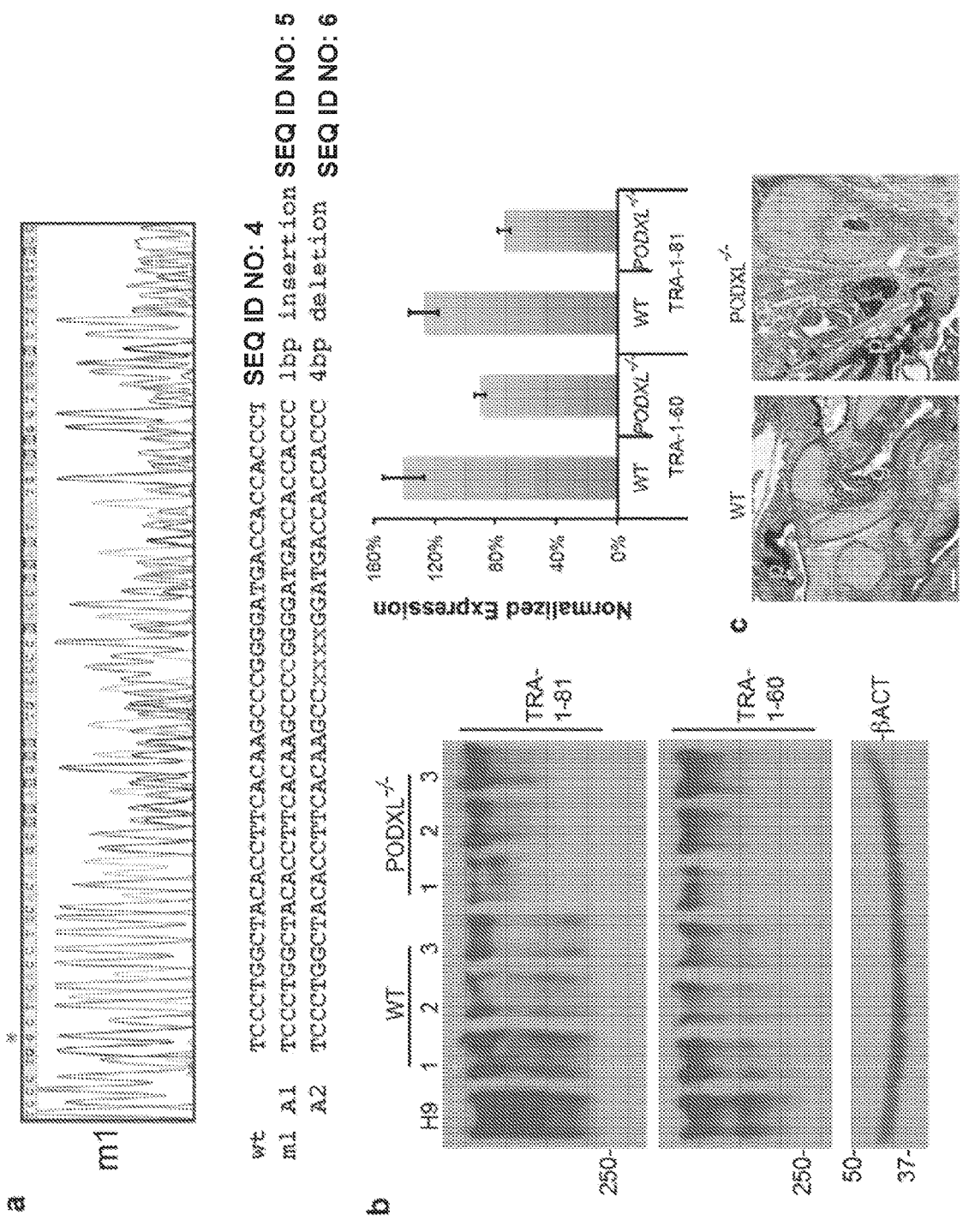
Figure 36:
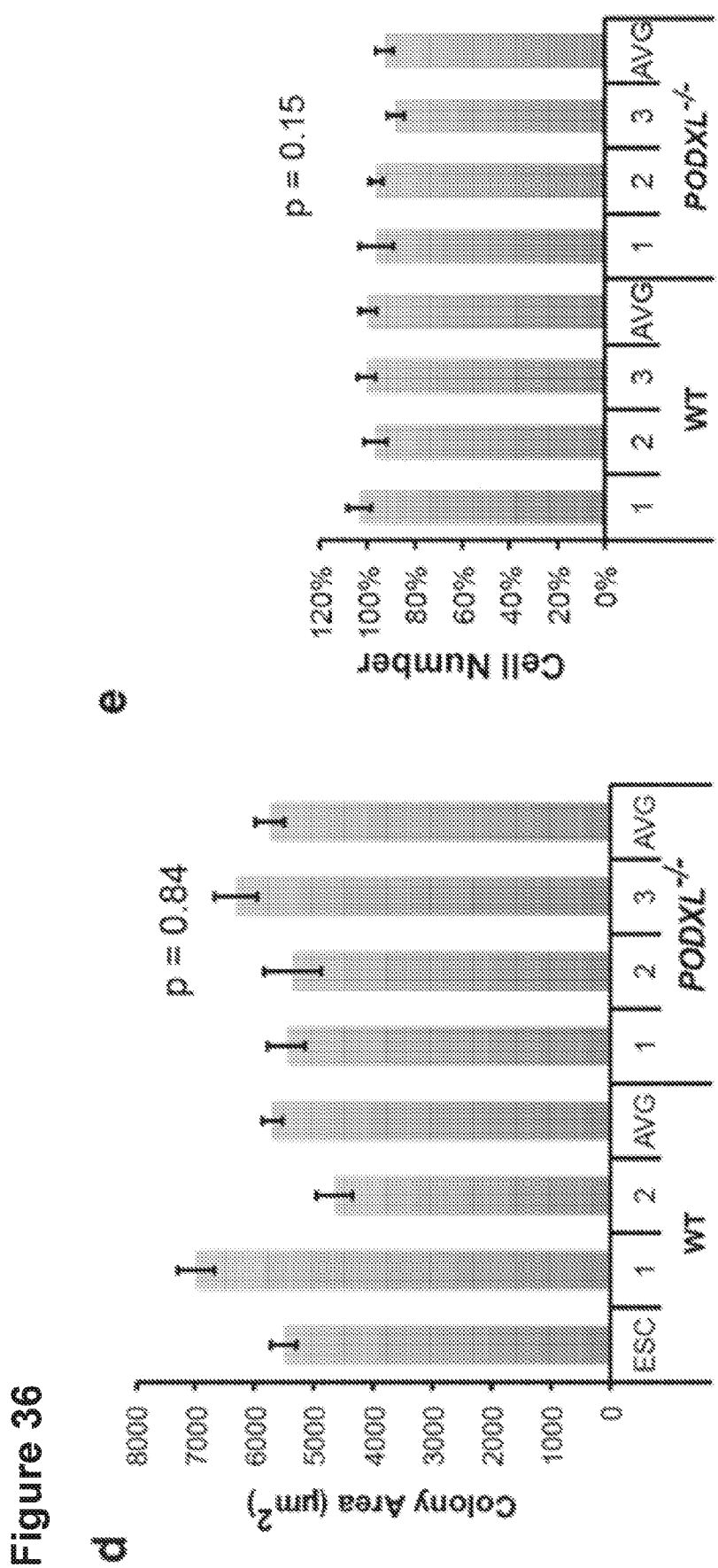

FIG. 36. Generation and characterization of PODxcl− hPSCs. (a) Chromatogram of a representative CRISPR/Cas9 podocalyxin mutant clone. Pink asterisk marks the beginning of the gRNA sequence. Interpretation shows separated alleles (A1 and A2) aligned against the wild-type sequence. (b) lmmunoblots showing TRA-1-60 and TRA-1-81 (multiple bands>250 kDa), with β-actin loading control. Right, quantification of band intensities, normalized to β-actin, averaged from 3-4 clones of wild-type or PODXL-1-hPSCs. (c) Teratomas from wild-type or PODXL-1− hPSCs showing ectodermal pigmented epithelium (p), mesodermal cartilage (c), and endodermal gut-like epithelium (g). (d) Total area per epiblast spheroid colony (AVG pooled from ≥7 experiments/SO colonies). (e) Dissociated cell number after −7 days growth in escapee (WT) and PODXL−/− hPSCs in 2D culture (AVG pooled from ≥14 experiments). Each experiment was normalized to the wild-type. Scale bar, 50 μm. Error bars, s.e.m.

Figure 37:
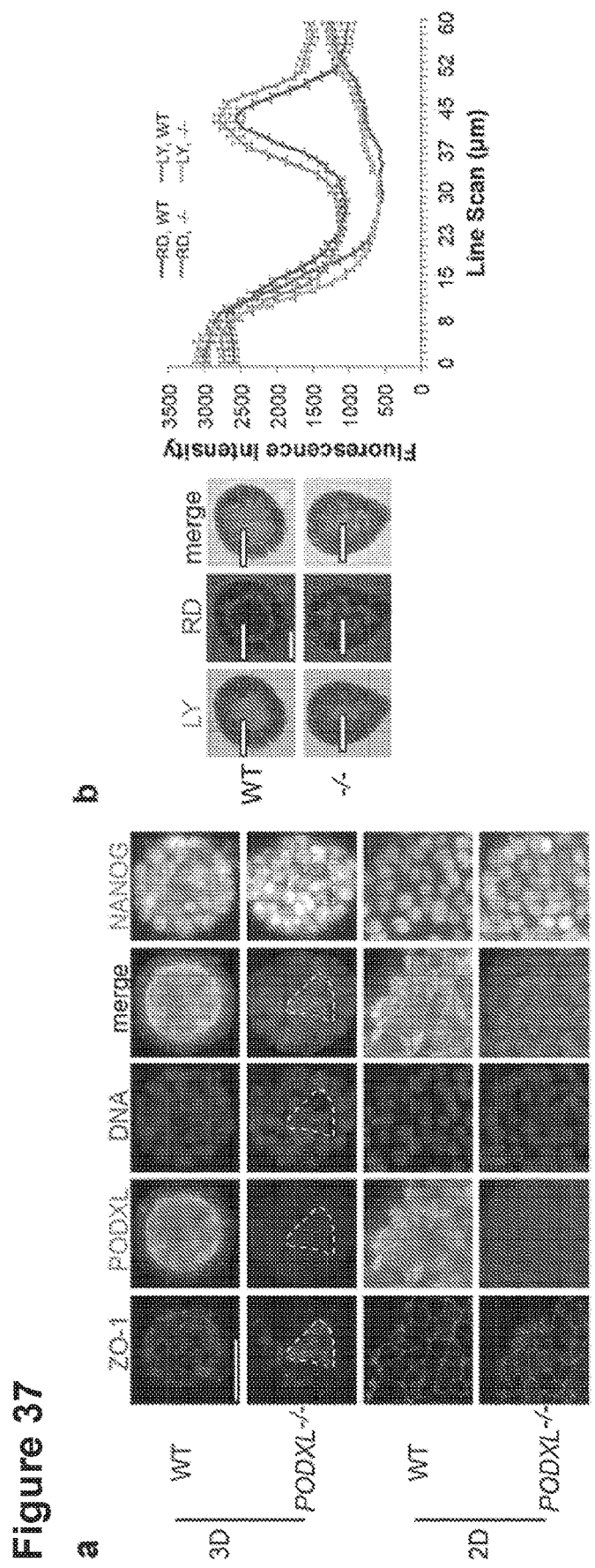
Figure 37:
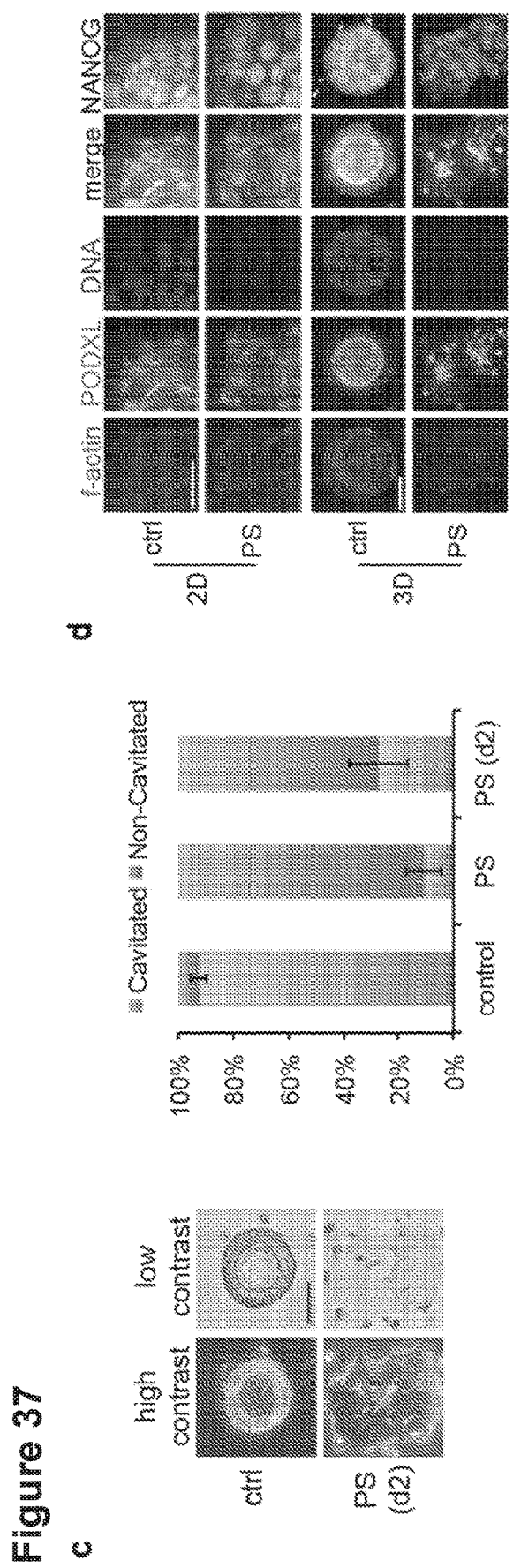

FIG. 37. Podocalyxin is dispensable for hPSC tight junction organization. (a) ZO-1, podocalyxin, and NANOG immunofluorescence images of CRISPR/Cas9 clones in 2D and 3D culture. A small lumen-like structure is observed in the PODXL−/− hPSC 3D aggregate (white dashed lines). (b) Representative images (left) and corresponding quantification (right) of wild-type or POD XL−/− spheroids after incubation with RD and L Y for four hours. Line scans (bordered white rectangles in images) from outside to inside representing 25 wild-type or PODXL−/− spheroids pooled from ≥2 hESC lines were averaged and plotted. (c) Brightfield images (left) and quantification (right) of hPSCs treated with 8 μg/ml protamine sulfate from the time of sandwiching (PS), the day after sandwiching (PS d2), or untreated controls. (d) PODXL localization in hPSCs treated with PS. Scale bars, 50 μm.

Figure 38:
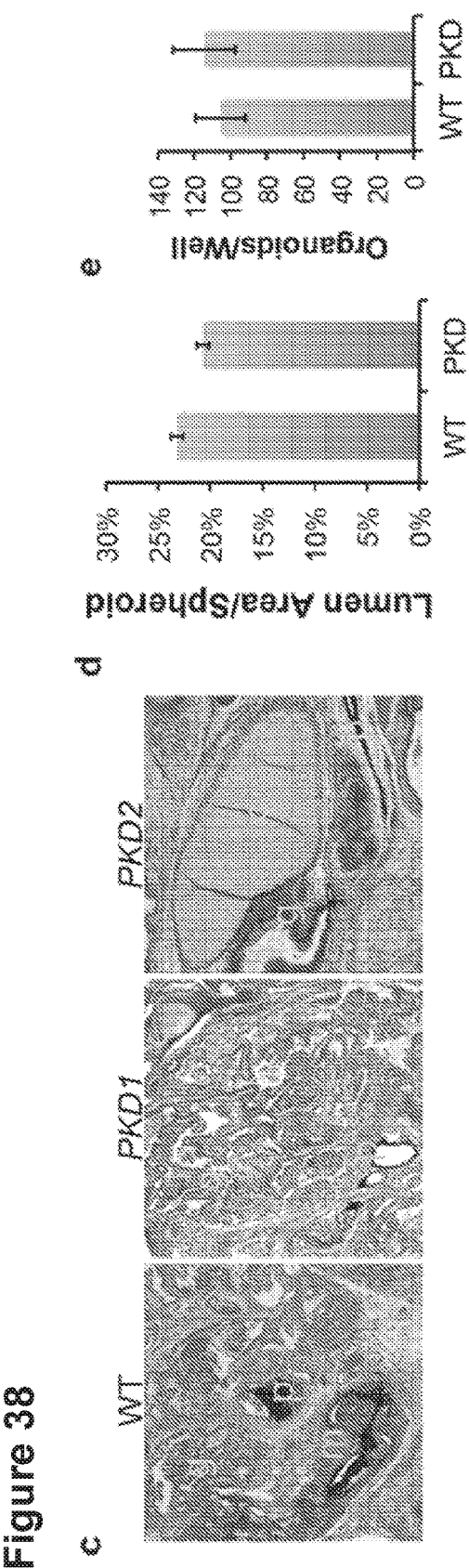

FIG. 38. Generation and characterization of PKD1−/− and PKD2−/− hPSCs. (a) Chromatograms (left) and full-length immunoblots (right) control (CTRL) and PKD1−/− hPSCs or (b) PKD2− hPSCs. shading marks 3' end of gRNA. Arrow indicates base pair number in the coding sequence. Interpretations of allele I (A 1) and allele 2 (A2) are compared to wild-type consensus sequence (WT). Multimeric PC2 is abbreviated as PC2mt− (c) Teratomas showing ectodermal pigmented epithelium (p), mesodermal cartilage (c), and endodermal gut-like epithelium (g). Scale bar, 100 μm. (d) Quantification of proportional lumen area relative to whole spheroid and (e) organoid differentiation efficiency in WT and PKD hPSCs (n~5 experiments). p<0.01.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 Jul. 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As described, human pluripotent stem cells (hPSCs) have dual value as microphysiological laboratory models and regenerative therapeutics. hPSCs are epithelial cells, but the extent to which hPSCs and descendant epithelia can reconstitute lineage-specific functions remains poorly understood. Here the Inventors show that hPSCs in three-dimensional cultures and their differentiated descendants can functionally recapitulate tissue-specific epithelial morphogenesis, physiology, and disease.

Undifferentiated hPSCs form spheroid colonies surrounding hollow, amniotic-like cavities, modeling the embryonic epiblast. A two-step protocol differentiates spheroids into convoluted, tubular organoids with developmental and structural characteristics of kidney nephrons, including proximal tubules, podocytes and endothelial cells. Kidney tubules and epiblast cavities differentially accumulate fluorescent cargoes and respond to nephrotoxic chemical injury. CRISPR/Cas9 knockout of podocalyxin or polycystic kidney disease genes produces disease relevant, tissue-specific phenotypes in kidney organoids, which are distinct from effects in epiblast spheroids. The Inventors' findings establish a reproducible and versatile three-dimensional framework for human microphysiology, disease modeling, and regenerative medicine applications.

The kidney is an organ of major interest to the field of regenerative medicine. Kidney epithelia are highly specialized and dysfunction of specific cell types can result in a variety of clinical disorders. For instance, polycystic kidney disease (PKD) features cystic expansion from tubular epithelial cells, whereas glomerulopathies involve injury to the podocyte epithelium through which blood plasma is filtered into the tubules. In proof-of-principle for using hPSCs to model kidney disease, the Inventors have described a ciliary phenotype in undifferentiated iPSCs and descendant epithelial cells from PKD patients. Recently, hPSCs have been directed to differentiate in vitro into tubular epithelia expressing markers typical of kidney progenitor cells, proximal tubules and podocytes.

However, the markers used in these studies are not exclusive to the kidney, and no study to date has demonstrated a disease-relevant phenotype in hPSC-derived kidney cells. Reconstitution of kidney-specific morphogenesis, microphysiology, and injury/disease states in hPSC-derived kidney cells is therefore important to more conclusively identify these epithelia and to advance their translational application.

Here, the Inventors establish adherent, 3D growth conditions for reconstitution of two distinct epithelial structures, epiblast spheroids and kidney tubular organoids, which arise sequentially in a single continuous culture of hPSCs. Using small molecule treatments and genome edited hPSCs, the Inventors demonstrate that these structures are capable of reconstituting tissue-specific epithelial transport, toxicity responses, and disease phenotypes. The Inventors' results reveal both common and tissue-specific features in hPSCs and descendant epithelia, with relevance for functional studies of human microphysiology, pathophysiology, and regenerative medicine.

Described herein is a method of generating human organoids, including providing a quantity of human pluripotent stem cells (hPSCs), culturing the hPSCs in a culture medium to form epiblast spheroids, and differentiating the epiblast spheroids in a differentiation medium, wherein the differentiation medium includes one or more agents capable of differentiating the epiblast spheroids into organoids. In various embodiments, the hPSCs are cultured in absence of leukemia inhibitory factor (LIF) and doxycycline prior to forming epiblast spheroids. In various embodiments, the hPSCs are cultured in the presence of Y27632 prior to forming epiblast spheroids. In various embodiments, the culture medium includes MATRIGEL™. In various embodiments, the culture medium includes collagen I. In various embodiments, culturing the hPSCs includes depositing a first layer of culture medium on a surface, placing the hPSCs on the deposited culture medium, and adding a second layer of culture medium over the hPSCs. In various embodiments, culturing the hPSCs in a culture medium includes about 1, 2 or more days. In various embodiments, the one or more agents include CHIR99021. In various embodiments, the one or more agents comprise B27. In various embodiments, differentiating the epiblast spheroids includes about 7, 8, 9, 10, 11, 12, or 13 or more days. In various embodiments, the epiblast spheroids express one or more of podocalyxin (PODXL), zonula occluden (ZO-1) and β-catenin. In various embodiments, the epiblast spheroids are cavitated. In various embodiments, the organoids are tubular. In various embodiments, the organoids are kidney organoids. In various embodiments, the organoids express one or more of podocalyxin (PODXL), zonula occluden (ZO-1), and lotus tetragonolobus lectin (LTL).

For example, hPSCs can be maintained feeder-free on about 3% Reduced Growth Factor GelTrex™ for at least one passage in media such as mTeSR1, or a hESC conditioned media (CM)+leukemia inhibitory factor (LIF)+dox for hLR5 iPSCs). In various embodiments, hPSCs are primed by withdrawing LIF and doxycycline. In various embodiments, withdrawal of LIF and doxycycline includes substitution with FGF2. In various embodiments, cells are plated a specific density relative to the culture surface and media volume. For example, about 30-60,000 cells/well of a 24-well plate or 4-well chamber slide pre-coated with Gel-Trex™ in media supplemented with 10 μM Rho-kinase inhibitor Y27632. In another example, about 5-20,000 of a 96-well plate were resuspended in 75 ul of either buffered collagen I (containing 10 mM HEPES and 1×DMEM), reduced growth factor MATRIGEL™ (BD Biosciences), or a 1:1 mixture of the two, incubated for 45 minutes at 37 degrees, and then overlaid with 100 ul of media plus Y27632.

For example, 48 hours after 3-D culture in the "sandwich" layers of culture medium, hPSC epiblast spheroids are differentiated in a differentiation medium including CHIR990021, at a concentration of, for example about 12 μM CHIR, and for a period of about 36 hours. In another example for kidney cell differentiation, the differentiation medium is changed to RB (Advanced RPMI+Glutamax+ B27 Supplement) and replaced every three days thereafter. In another embodiment, epiblast spheroids are differentiated in a differentiation medium including CHIR990021, at a concentration of, for example about 12 µM CHIR, and media that is RB minus insulin (RBNI) for a period of about 24 hours, RBNI for 48 hours, addition of 5 µM IWP2 for 48 hours, RBNI for 48 hours, and RB every three days thereafter.

Also described herein is a quantity of organoids made by a method of generating human organoids, including providing a quantity of human pluripotent stem cells (hPSCs), culturing the hPSCs in a culture medium to form epiblast spheroids, and differentiating the epiblast spheroids in a differentiation medium, wherein the differentiation medium includes one or more agents capable of differentiating the epiblast spheroids into organoids. In various embodiments, the hPSCs are cultured in absence of leukemia inhibitory factor (LIF) and doxycycline prior to forming epiblast spheroids. In various embodiments, the hPSCs are cultured in the presence of Y27632 prior to forming epiblast spheroids. In various embodiments, the culture medium includes MATRIGEL™. In various embodiments, the culture medium includes collagen I. In various embodiments, culturing the hPSCs includes depositing a first layer of culture medium on a surface, placing the hPSCs on the deposited culture medium, and adding a second layer of culture medium over the hPSCs. In various embodiments, culturing the hPSCs in a culture medium includes about 1, 2 or more days. In various embodiments, the one or more agents include CHIR99021. In various embodiments, the one or more agents comprise B27. In various embodiments, differentiating the epiblast spheroids includes about 7, 8, 9, 10, 11, 12, or 13 or more days. In various embodiments, the epiblast spheroids express one or more of podocalyxin (PODXL), zonula occluden (ZO-1) and β-catenin. In various embodiments, the epiblast spheroids are cavitated. In various embodiments, the organoids are tubular. In various embodiments, the organoids are kidney organoids. In various embodiments, the organoids express one or more of podocalyxin (PODXL), zonula occluden (ZO-1), and lotus tetragonolobus lectin (LTL). In various embodiments, the hPSCs are genetically modified using genomic editing, such as CRISPR.

Also described herein is a method of generating tubular organoids, including providing a quantity of epiblast spheroid and differentiating the epiblast spheroids in a differentiation medium, wherein the differentiation medium includes one or more agents capable of differentiating the epiblast spheroids into organoids. In various embodiments, the one or more agents comprise CHIR99021. In various embodiments, the one or more agents comprise B27. In various embodiments, differentiating the epiblast spheroids includes about 7, 8, 9, 10, 11, 12, or 13 or more days. In various embodiments, the tubular organoids are kidney organoids. In various embodiments, the kidney organoids express one or more of podocalyxin (PODXL), zonula occluden (ZO-1), and lotus tetragonolobus lectin (LTL). In various embodiments, differentiating the epiblast spheroids into kidney organoids includes further culturing in a second differentiation medium including RPMI and B27. In various embodiments, differentiating the epiblast spheroids into kidney organoids includes further culturing in a second differentiation medium including CHIR99021, RPMI and B27 for about 24 hours, replacement of the second differentiation medium with a third differentiation medium including CHIR99021, RPMI, B27 and insulin and additional culturing for about 48 hours, addition of IWP2 and continued culturing for about 48 hours, and additional replacement of the third differentiation medium with the second differentiation medium.

Also described herein is a method of screening a compound for an effect on tubular organoids, including providing a quantity of tubular organoids, adding one or more compounds to the tubular organoids, determining changes to phenotype or activity of the tubular organoids, and correlating the changes with an effect of the compounds on tubular organoids, thereby screening the one or more compounds for an effect on tubular organoids.

In various embodiments, determining changes to phenotype or activity includes detecting one or more markers in the tubular organoids. In various embodiments, the one or more markers comprise kidney injury molecule (KIM-1). In various embodiments, an increase in KIM-1 expression correlates with a toxic effect of the compound. In various embodiments, the tubular organoids are kidney organoids.

Example 1

3D Culture

Cell lines included H9 (WA09), BJ, HDFn, hLR5, hfib2-iPS4, and hfib2-iPS5 (human) and J1, R1, and v6 (mouse). Cells were maintained feeder-free on 3% Reduced Growth Factor GelTrex™ (Life Technologies) for at least one passage in media (mTeSR1 for hPSCs; N2/827 supplement+2i in for mESCs; hESC conditioned media (CM)+leukemia inhibitory factor (LIF)+dox for hLR5 iPSCs) and dissociated with Accutase® or TrypLE™. LD-iPSCs were derived from native hLR5 iPSCs by withdrawing LIF and doxycycline and substituting with FGF2. For thin gel sandwich colonies, cells were plated at 60,000 (primed) or 30,000 (native) cells/well of a 24-well plate or 4-well chamber slide pre-coated with GelTrex™ in media supplemented with 10 µM Rho-kinase inhibitor Y27632 (StemGent). The following day the media was replaced with 500 µL 1.5% GelTrex™ in mTeSR1. Media was changed after 24 hours. For thick gel cultures, 20,000 (epiblast-stage) or 6,000 (naive) cells/well of a 96-well plate were resuspended in 75 ul of either buffered collagen I (containing 10 mM HEPES and 1× DMEM), reduced growth factor MATRIGEL™ (BD Biosciences), or a 1:1 mixture of the two, incubated for 45 minutes at 37 degrees, and then overlaid with 100 ul of media plus Y27632. For serial passaging in thin gels, colonies with lumens in 3D cultures were dissociated 72 hours after plating, replated at a density of 300,000 cells/well of a 6 well plate, and cultured for 72 hours in either 2D or 3D conditions before dissociation, cell counting, and replating. For suspension, 20,000 dissociated hPSCs were plated in mTeSR1 media in one well of a low-adherence 6-well plate. For all cells, media was changed daily.

Example 2

Tubular Organoid Differentiation 60,000-120,000 H9 hPSCs were plated, sufficient to produce scattered, isolated spheroid colonies. 48 hours after sandwiching, hPSC spheroids were treated with 12 µM CHIR for 36 hours, then changed to RB (Advanced RPMI+Glutamax+B27 Supplement) and replaced every three days thereafter. Alternatively, spheroids were treated with 12 µM CHIR in RB minus insulin (RBNI) for 24 hours, RBNI for 48 hours, 5 µM IWP2 for 48 hours, RBNI for 48 hours, and RB every three days thereafter, as described for 2D cardiomyocyte differentiation. For 2D kidney differentiation, cells were plated overnight and then treated with 8 µM CHIR in APEL™ media (StemCell Technologies) for 48-72 hours, 30 ng/ml FGF2+1 µg/ml heparin in APEL™ media for 96 hours, and subsequently cultured in APEL™ media for 10-15 days. For stochastic differentiation, hPSCs in 2D or 3D cultures were treated with 10% fetal bovine serum (FBS) in DMEM+P/S and observed for 19 days. Immunofluorescence and Electron Microscopy To fix while preserving 3D architecture, an equal volume of 8% paraformaldehyde was added to the culture media (4% final concentration) for 15 minutes at room temperature. After fixing, samples were washed in PBS, blocked in 5% donkey serum (Millipore)/0.3% Triton-X-100/PBS, incubated overnight in 3% bovine serum albumin/PBS with primary antibodies, washed, incubated with Alexa-Fluor secondary antibodies (Invitrogen), washed, and stained with DAPI or mounted in Vectashield™ H-1000. Primary antibodies included OCT4 (sc-5279; Santa Cruz), NANOG (RCAB0004PF; Cosmobio), brachyury (sc-17745; Santa Cruz), TRA-1-60 (MAB4360, Millipore), TRA-1-81 (MAB4381; Millipore), acetylated o-tubulin (051M4770; Sigma), ZO-1 (339100; Invitrogen), podocalyxin (AF1658 and AF1556; R&D), CDX2 (-88, Biogenex), AQP1 (AB2219; Millipore), WT-1 (sc-192; Santa Cruz), LHX1 (Developmental Studies Hybridoma Bank), mPODXL (AF1556; R&D), hPODXL (AF1658, R&D), HNA (MAB1281, Millipore), LTL (FL-1321, Vector Labs), SYNPO (sc-21537; Santa Cruz), CD31 (555444; BD), crumbs 3 (HPA013835, Sigma), Na,K-ATPase (ab7671, Abcam), and cleaved caspase-3 (MAB835; R&D). Fluorescence images were captured using a Nikon epifluorescence 90-1 (upright), Eclipse Ti (inverted), or confocal C1 microscopes. For electron microscopy, structures were scraped from the plate after 5 minutes of fixation, pelleted at 300 g for four minutes, and the pellet was gently released by pipetting into cacodylate buffer containing 4% formaldehyde and 2% glutaraldehyde, postfixed with osmium tetroxide, dehydrated in serial ethanols, and embedded in epoxy resin. Semi-thin sections were cut at 1 mm and stained with toluidine blue to identify tubular structures with apparent lumens by light microscopic examination. Ultrathin sections (75 nm) were cut, mounted on 200 mesh copper grids, counterstained with uranyl acetate and lead citrate, and examined in a JEOL JEM-1010 transmission electron microscope.

Example 3

Permeability Assays

To test permeability, media was supplemented with 20 mM HEPES plus Lucifer Yellow™ carbohydrazide potassium salt (Invitrogen, 38 µM) and Rhodamine-8 isothiocyanate dextran (Sigma, 0.5 µM), and imaged by confocal microscopy. For microinjection, 5 µM rhodamine-conjugated dextran solution in mTeSR1 was diluted 1:1 with Phenol Red Solution (0.5%, Sigma) for visualization. 2 nl was microinjected via a pulled glass capillary microneedle on a Nanoject-2 micromanipulator, and monitored in real-time by wide-field epifluorescence. For TEER, 50,000 hPSCs were plated on 24-well transwell plates (Corning) pre-coated with dilute MATRIGEL™. The media was gently exchanged for 10 days until cells were completely confluent. TEER was measured using an EVOM 2™ device (World Precision Instruments).

Example 4

KIM-I Induction

Organoids in identically-plated wells of a 24-well plate were treated with increasing concentrations of gentamicin and cisplatin for 36-48 hours, fixed, and processed for immunofluorescence with KIM-1 antibodies AKG7.9 (Bonventre laboratory) or 1400 (Biogen). Immunofluorescence for KIM-1 was observed at moderate, sub-toxic doses which did not induce gross tubular disintegration.

Example 5

RNA Interference 16 hours after plating, hPSCs were transfected with Dharmacon Smartpool™ siRNAs directed against PODXL, OCT4, or scrambled control in mTeSR1 without antibiotics. Ten hours later, the media was changed and the cells were either cultured in 2D or sandwiched for 3D culture.

Example 6

Cas9/CRISPR Mutagenesis

Constructs encoding green fluorescent protein (GFP)-tagged Cas9 (Addgene 44719) and a guide RNA (Addgene 64711) targeting the second exon of PODXL (GCTACACCTTCACAAGCCCGGGG) [SEQ ID NO: 1], the first exon of PKD2 (GCGTGGAGCCGCGATAACCCCGG) [SEQ ID NO: 2], or the thirty-sixth exon of PKD1 (GTGGGTGCGAGCTTCCCCCCGGG) [SEQ ID NO: 3] were transiently transfected into H9 hESCs, and GFPexpressing cells were isolated by flow cytometric sorting, clonally expanded, and screened for clones with biallelic loss-of-function indels. –200,000 sorted hESCs were plated per well of a 6-well plate in hESC-conditioned mTeSR1 plus Y27632. Media was replaced the following morning without Y27632 and cells were clonally expanded and the PODXL gRNA region was amplified by PCR. Chromatogram sequences were analyzed manually and mutations were confirmed by immunoblot and immunofluorescence.

Example 7

Transcriptome Profiling hPSCs plated in 2D or 3D were prepared side-by-side using the RNEasy™ Mini Kit (Qiagen). Samples were QC'd on the Agilent Bioanalyzer™ to check for high integrity samples. Qualifying samples were then prepped using the TruSeq™ stranded mRNA library kit (Illumina). Sequencing was performed on an Illumina NextSeq500 75×75 paired end high output run. Samples were aligned to hg19 reference sequence using Tophat2 and differential expression calculated using Cuffdiff.

Example 8

RT-PCR

RNA was prepared on days 2, 10, 14, and 21 after plating during the differentiation time course using the RNeasy Mini Kit (Qiagen). RNA from all time points was reverse transcribed side-by-side using the M-MLV Reverse Transcription System (Promega). Quantitative RT-PCR reactions were run in duplicate using cDNA (diluted 1:10), 300 nM primers, and iQ SYBR Green™ Supermix (Bio-Rad) with the iQ5 Multi-Color Real-Time PCR Detection System (Bio-Rad), using P-actin as the housekeeping gene.

Example 9

Quantification and Statistical Analysis

For fluorescence intensity quantifications, images were taken in a single imaging session and at identical exposures and processed identically. The number of cavitated colonies (ellipsoid with lumen) versus flat colonies (non-ellipsoid or without a lumen) was scored manually in phase contrast images of living cells, in which lumens were discerned more easily than in fixed samples. For apoptosis, cleaved caspase-3 expression was scored manually, confirmed by nuclear condensation, and divided by the total number of nuclei per wide-field epifluorescent image. For ZO-1 areas, individual colonies or subregions expressing ZO-1 were traced manually and surface areas calculate using NIS Elements (Nikon). For each colony, the summed ZO-1 expressing area was expressed as a percentage of the total surface area and then averaged. To quantify intensities, line scans of equal length were drawn through randomly selected structures imaged with identical exposures to obtain raw fluorescence values in NIS Elements software (Nikon). The averaged line scan values were plotted with error bars. For CHIR-induced differentiation, ~6000 individual cells were identified in low-magnification immunofluorescence images using Cell Profiler 2.0 and fluorescence intensities were measured automatically. Statistical comparisons utilized a two-tailed I test for two samples with unequal variance (heteroscedastic). Immunoblots were quantified using the ImageJ Gel Analyzer.

Example 10

Cavity and Tubule Morphogenesis in a Continuous 3D Culture of hPSCs

Figure 1:
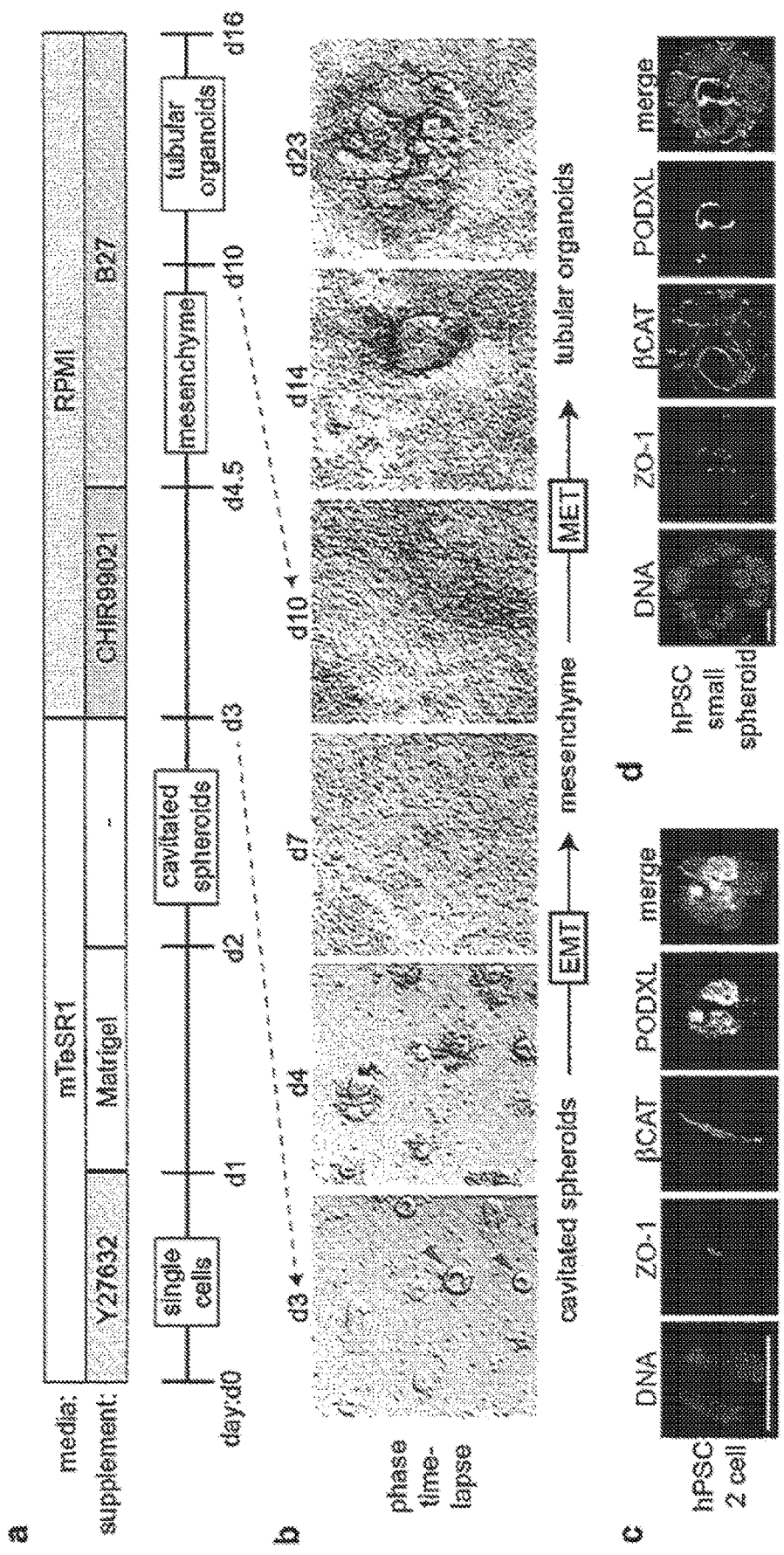
FIG. 1. Epithelial morphogenesis of hPSCs and descendant cells in a continuous 3D culture. (a) Schematic and (b) phase-contrast time-lapse images of spheroid-to-organoid culture protocol. Red arrowheads highlight epithelia. Dashed black arrows link schematic with figures. (c) Confocal optical sections showing podocalyxin (PODXL), ZO-1, and β-catenin (βCAT) immunofluorescence through a representative sandwiched 2-cell hPSC aggregate, (d) small spheroid, (e) large spheroid with cavity, and (f) monolayer colony. Vertical distance from top to bottom row is shown at left. Higher magnification views are shown in FIG. 13. (g) Low-magnification wide-field image and (h-i) high magnification confocal optical sections showing immunofluorescence of epithelial polarity markers in tubular organoids, with LTL counterstain. Scale bars, 100 µm (a-b, g-i) or 20 µm (c-f).
Figure 1:
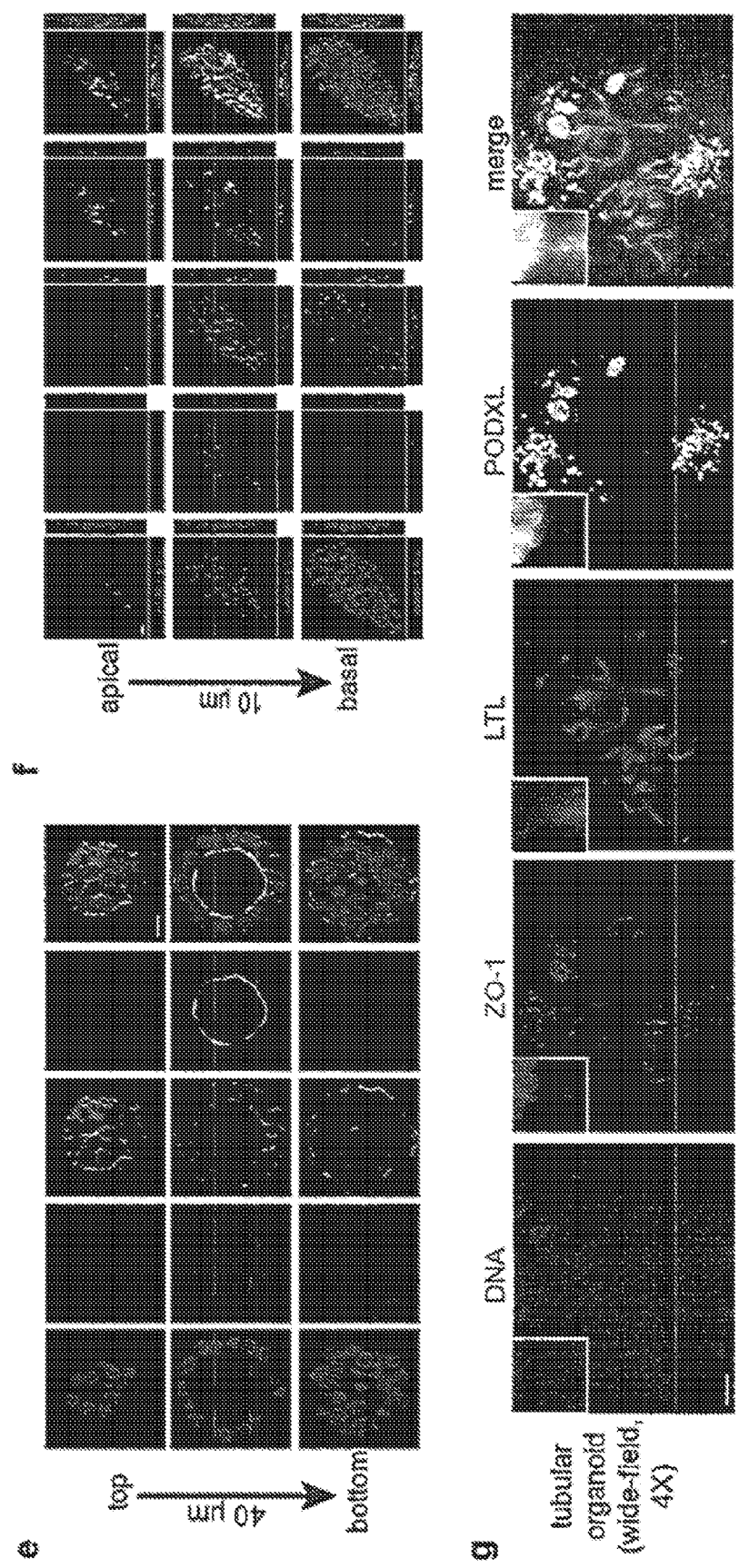
Figure 1:
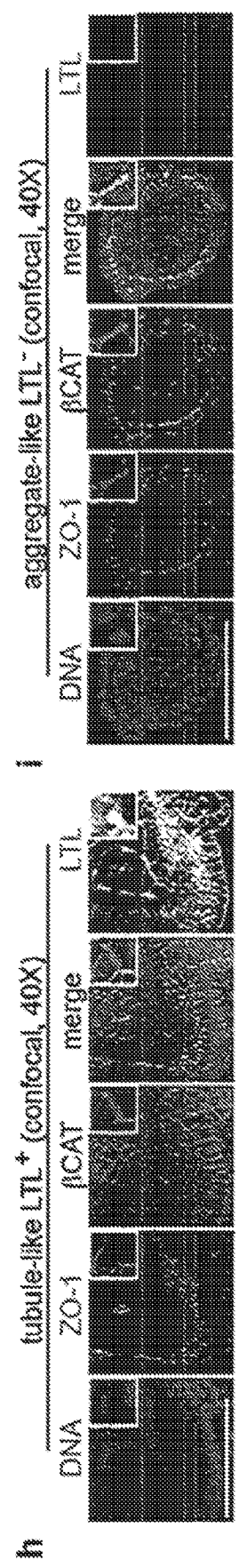

To reconstitute human epithelia from undifferentiated hPSCs and their somatic descendants, the Inventors developed an adherent, 3D culture system for hPSCs that first produced hollow spheroids and subsequently tubules (FIG. 1 *a-b*). Dissociated, undifferentiated hPSCs sandwiched between two layers of dilute MATRIGEL™ (0.2 mg/mL) formed compact, ball-like colonies; by 48 hours, these formed internal cavities (FIG. 1 *b* and FIG. 11 *a-b*). Spheroid cavity formation was a highly dynamic process, featuring colony fusion events and rotational movements, and was sensitive to incubation time and colony size (FIG. 11 *a-e*). Cavities were not observed in MOCK spheroids under similar dilute-gel conditions (FIG. 11*f*). hPSCs also formed cavitated spheroids in undiluted MATRIGEL™, a MATRIGEL™:collagen mixture, and suspension cultures, but not in collagen alone (FIG. 12*a-f*). Mature spheroids consisted of a simple columnar epithelium surrounding a hollow lumen, with polarized localization of podocalyxin to the luminal surface, zonula occludens (ZO)-1 to apical cell-cell junctions, and β-catenin to primarily basolateral membranes (FIG. 1 *c-e*). Similar apicobasal polarization patterns were observed in monolayer colonies of undifferentiated hPSCs (FIG. 1*f* and FIG. 13*a*). To generate descendant epithelia from the same hPSCs, cavitated spheroids were treated for 36 hours with the glycogen synthase kinase-3β inhibitor CHIR99021 (CHIR) and subsequently incubated in defined growth media (FIG. 1*a-b*). Following CHIR treatment, spheroid cells underwent epithelial-tomesenchymal transition (EMT) to form a confluent monolayer that by day 10 aggregated into folds and initiated mesenchymal-to-epithelial transition (MET) into convoluted, translucent, tubular organoids (FIG. 1*a-b*). Tubules reacted strongly with *Lotus tetragonolobus* lectin (L TL), a property of certain adult epithelia such as kidney proximal tubules, whereas epiblast spheroids examined side-by-side had negligible affinity for L TL (FIG. 1*g* and FIG. 13*b*). The Na,KATPase, a broadly expressed epithelial marker, was expressed in both epiblast spheroids and tubular organoids (FIG. 13*c*). Confocal microscopy revealed that L TL+tubules expressed luminal ZO-1 and basolateral β-catenin in cobblestone patterns, with faint apical podocalyxin (FIG. 1*g-h*). Adjacent to the tubules, a second ZO-1+epithelial cell population formed clustered aggregates, which strongly expressed podocalyxin, but did not bind L TL (FIG. 1*g*). Confocal analysis of these L TL-negative aggregates revealed a rounded cellular morphology and strong co-localization of ZO-1 and β-catenin in zipper-like structures between cell layers, without apparent lumenogenesis (FIG. 1*i*). Thus, this method enabled generation of distinct epithelial cell populations and organized structures within a single adherent culture of differentiating hPSCs.

Example 11

Cavitated Spheroids Represent Undifferentiated Epiblast

Figure 2:
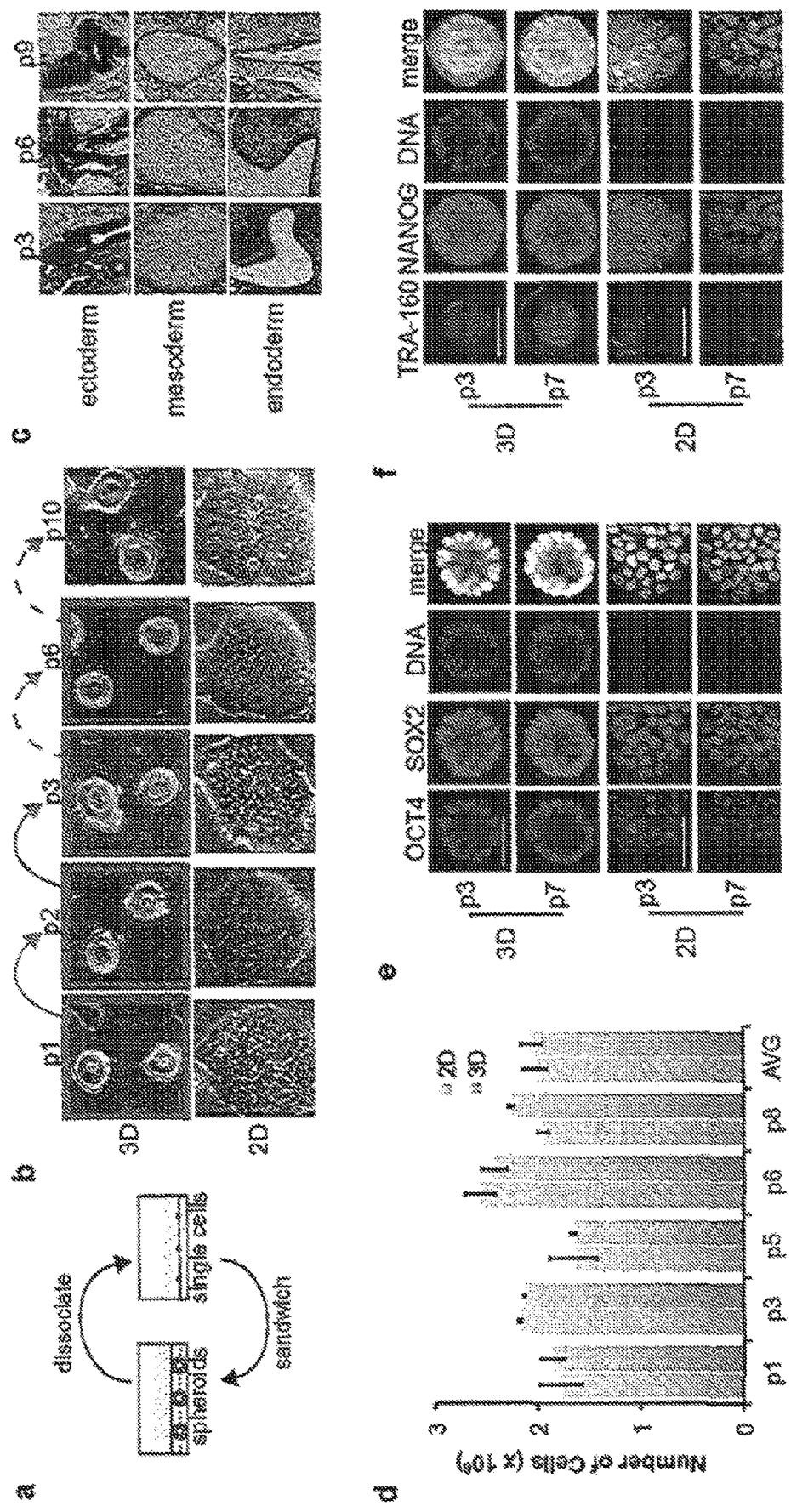
FIG. 2. Cavitated spheroids represent epiblast. (a) Schematic of serial passaging experiment. (b) Representative brightfield images of hPSCs in 3D cultures which were dissociated (colored frames) and passaged (matching colored arrows). Dashed arrows represent serial passages in the 3D condition. Lower row shows cells plated into 2D cultures from dissociated spheroids from each passage. (c) Hematoxylin and eosin-stained sections of teratomas generated from hPSC serial 3D passages p3, p6, and p9 showing pigmented epithelium (ectoderm), cartilage (mesoderm), and glandular epithelium (endoderm). (d) Cell number (average of duplicate counts for each time point, or AVG of all time points) in 2D and 3D cultures 72 hours after plating. (e) Representative immunofluorescence images showing OCT4 and SOX2 and (f) TRA-1-60 and NANOG localization in p3 and p7 serially sandwiched hPSCs. (g) Naive and primed hLR5 morphologies with corresponding ZO-1 and podocalyxin immunofluorescence in 3D cultures. (h) Morphology and (i) quantification (n=3) of hPSC colonies cultured in mTeSR1 plus CHIR, compared to controls in mTeSR1 alone. (j) Representative images and (k) dot plots showing DAPI-normalized immunofluorescence of OCT4 and BRY in 3D cultures treated with increasing CHIR in mTeSR1. Each dot represents a single hESC or hiPSC (pooled, n>6, 000 cells per condition). Scale bars, 50 µm. Error bars, s.e.m.
Figure 2:
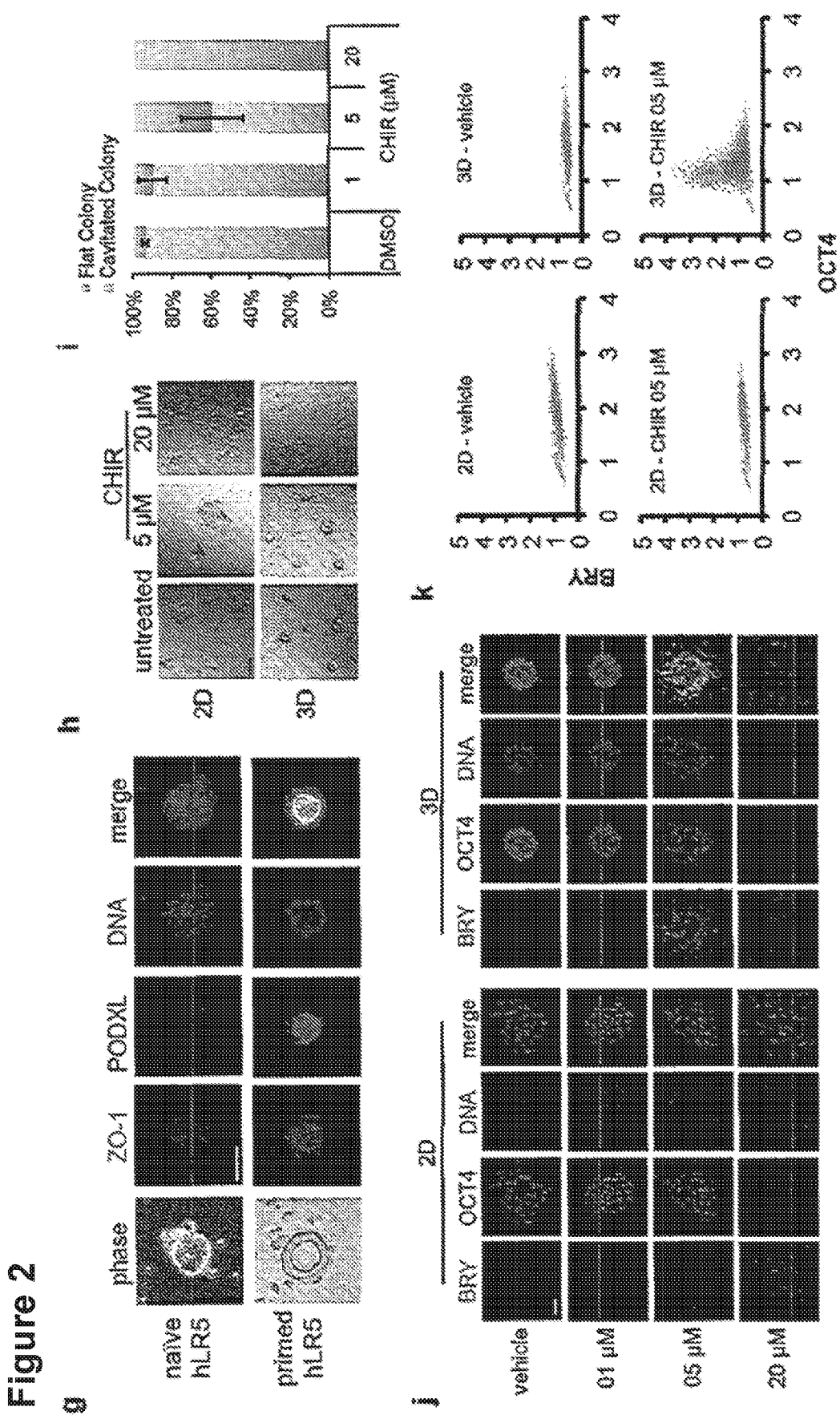

The Inventors tested hPSC spheroids for pluripotency and self-renewal, which are the key functional characteristics of undifferentiated hPSCs. Cavitated spheroids were repeatedly dissociated, replated, and sandwiched (FIG. 2*a*). In nine serial passages, dissociated cavity-lining cells generated new cavitated spheroids after sandwiching, or alternatively flat colonies when the final passage was into monolayer conditions (FIG. 2*b*). Even after extensive serial passages to/from 3D culture, cavity-lining cells implanted into immunodeficient mice efficiently produced teratoma tissues derived from all three embryonic germ layers (FIG. 2*c*). 2D and 3D cultures exhibited similar growth rates, and pluripotency markers continued to be expressed in identical patterns in serially sandwiched cells, including octamer binding transcription factor 4 (OCT4), sex determining region Y box-2 (SOX2), NANOG, and TRA-1-60 (FIG. 2*d-f*). Thus, spheroids represented undifferentiated, self-renewing pluripotent cells rather than a differentiated subtype.

The Inventors hypothesized that hPSC spheroids model the epiblast epithelial mass, which forms an early amniotic cavity in human and primate implantation-stage embryos. Conversely, hPSCs resembling the more primitive ICM were predicted not to cavitate. Indeed, naive' hLR5 iPSCs, which form compact, ICM-like colonies similar to mouse (m)ESCs, did not form lumens in 3D cultures even after five days of growth, correlating with low podocalyxin expression and discontinuous ZO-1 localization (FIG. 2*g* and FIG. 14*a-c*). In contrast, 'primed' hLR5-derived (LO-)iPSCs, which resemble epiblast-stage hPSCs, formed cavities efficiently in sandwich cultures and strongly expressed podocalyxin and ZO-1 in polarized, continuous localization patterns (FIG. 2*g* and FIG. 14*a-c*). Similarly, naive mESCs, which resemble the ICM, did not form cavities under a variety of 3D culture conditions, whereas epiblast-stage mEpiSCs formed rosettes surrounding ZO-1+PODXL+ lumens (FIG. 14d-g). Both naive and primed hPSCs continued to express nuclear OCT4 and SOX2 in both 2D and 3D cultures (FIG. 14h). Chemical inhibition of the cell division control protein 42 homolog (CDC42) significantly reduced cavity formation in hPSCs, whereas caspase inhibition had no effect, consistent with known properties of the epiblast (FIG. 15a-e). To test the effect of differentiation on spheroid formation, hPSCs were treated with CHIR, a potent and rapid inducer of brachyury (BRY) expression and mes-endodermal differentiation.

CHIR added at the time of sandwiching inhibited spheroid formation in a dose-dependent manner, with differentiating cells undergoing EMT and radiating outwards away from their colonies of origin (FIG. 2h-j). These experiments identified the epiblast stage as a critical window for hPSC spheroid lumenogenesis, whereas naïve (ICM-stage) or CHIR-differentiated hPSCs could not form lumens.

Example 12

CHIR Treatment Differentiates Spheroids into Tubular Organoids

Figure 3:
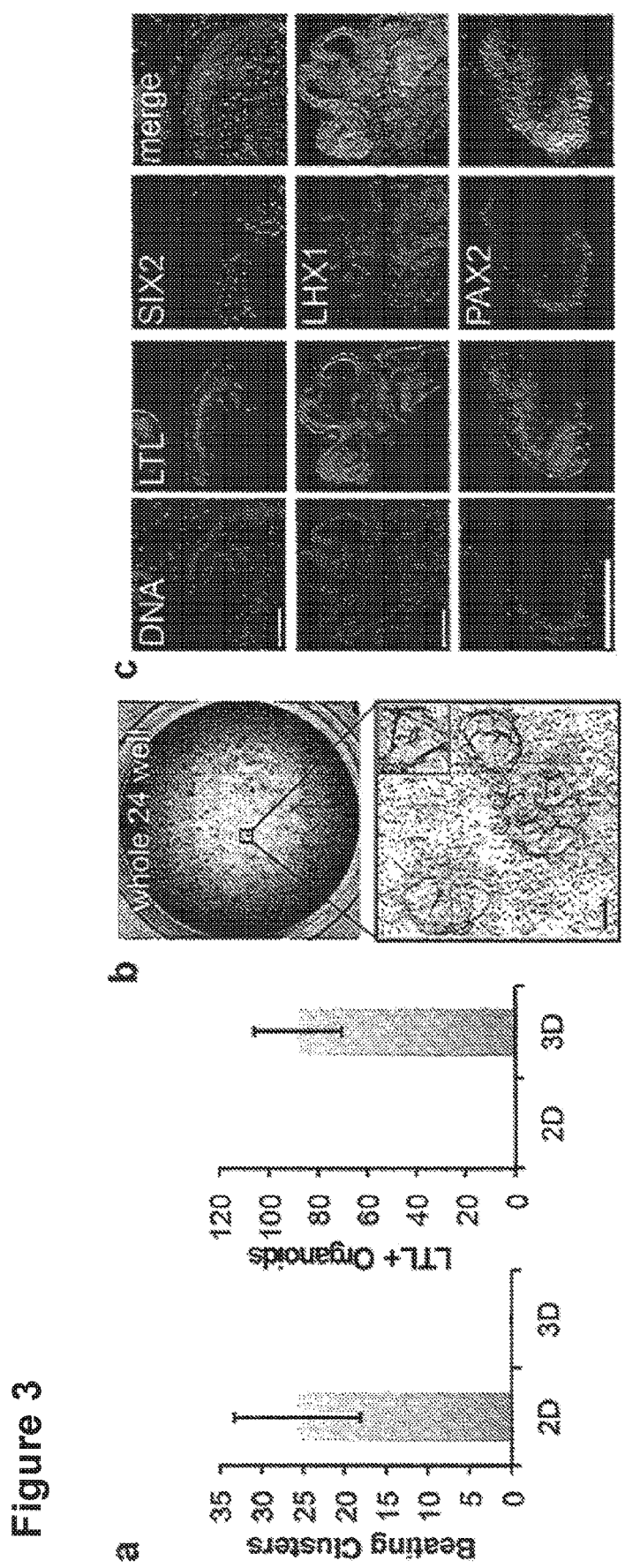
Figure 3:
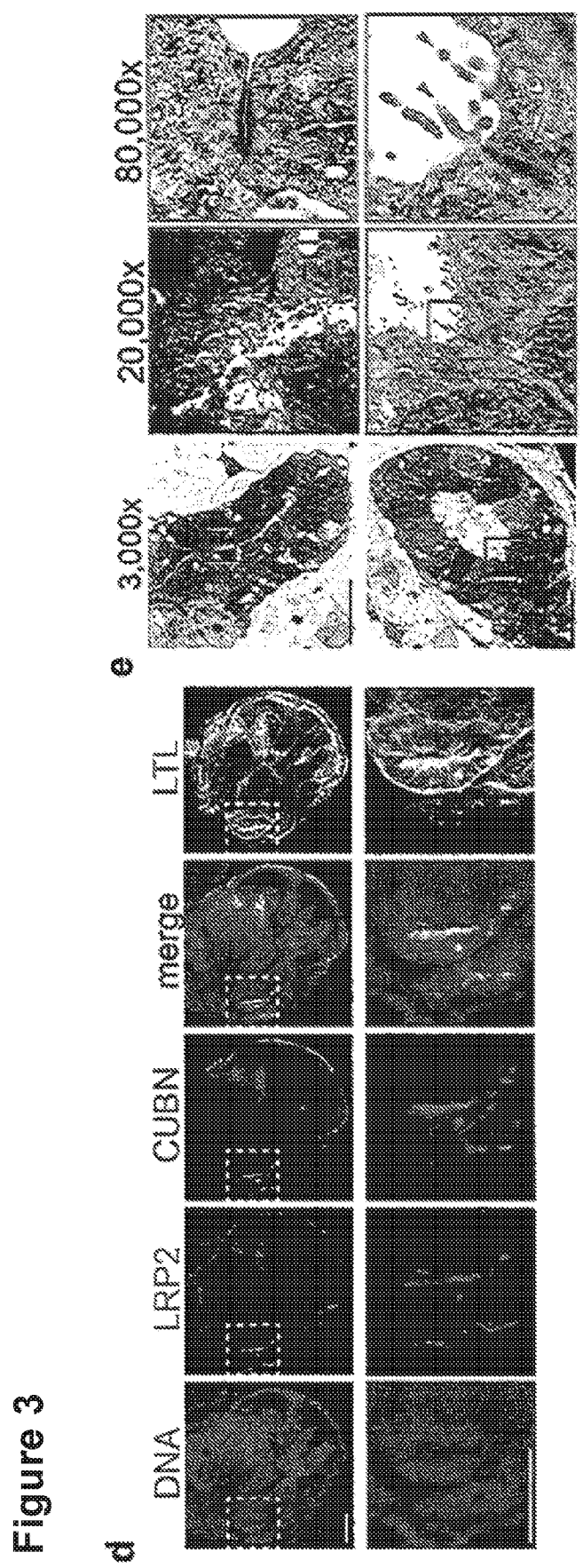
Figure 3:
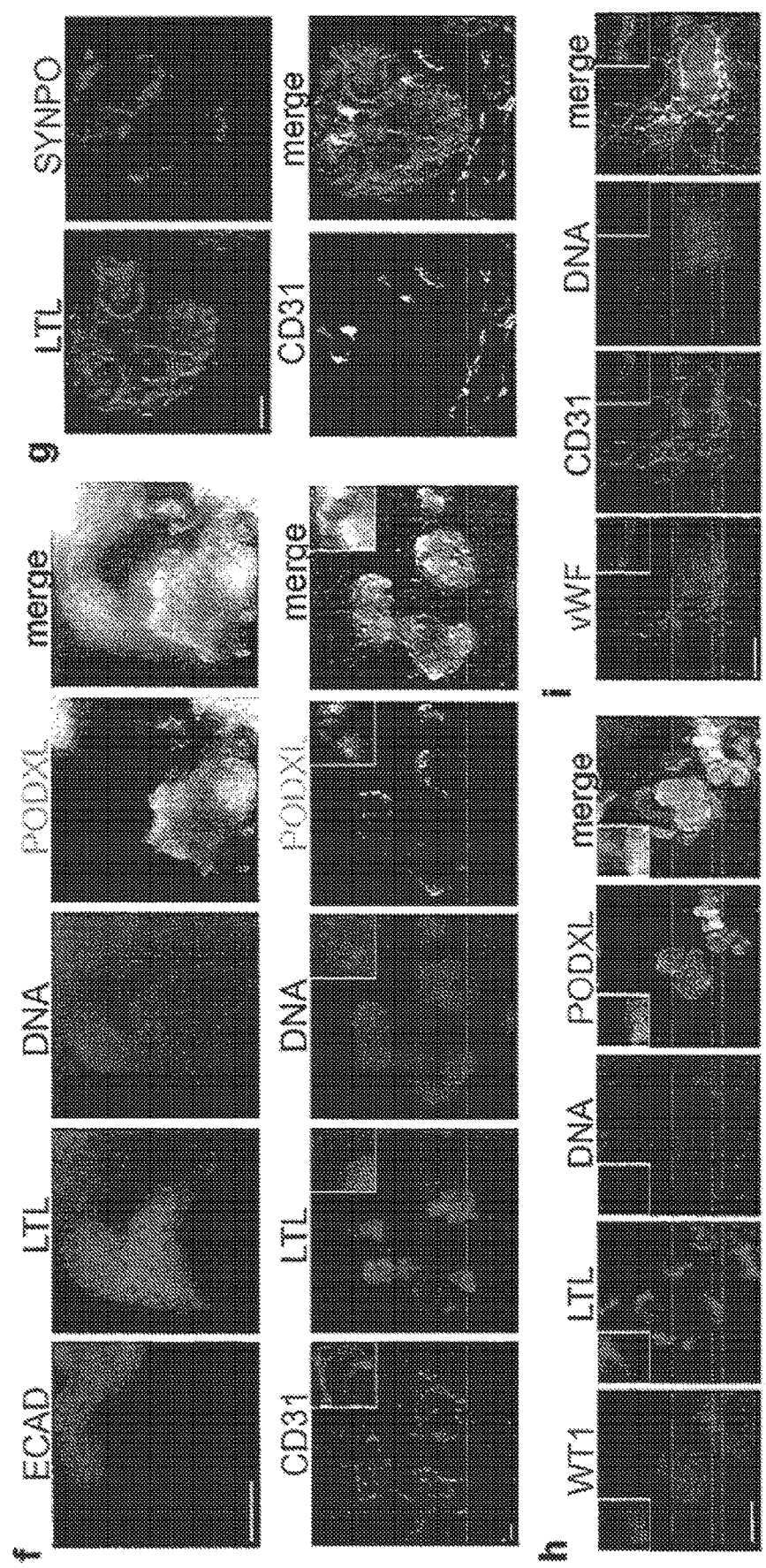

In the preceding experiment, the Inventors observed that 5~M CHIR induced higher levels of BRY expression in 3D cultures than in 2D cultures plated side-by-side (FIG. 2j-k). 2D colonies and 3D spheroids in pluripotency-sustaining (mTeSR1) media had nearly identical global gene expression profiles prior to CHIR treatment, suggesting that 3D culture alone did not cause spontaneous differentiation (FIG. 16a). To further investigate the effects of CHIR on 3D cultures, the Inventors applied a directed differentiation regimen originally designed for cardiomyocyte generation from 2D cultures. Remarkably, in 3D cultures, the resultant mesenchyme epithelialized into convoluted tubular organoids, rather than contractile cardiomyocytes (FIG. 3a-b; see FIG. 1 a-b). To test whether these effects were specific to CHIR treatment, the Inventors differentiated 2D and 3D cultures stochastically with serum. Such cultures produced confluent monolayers of ZO-1+LTL-epithelial cells, but did not produce tubules or cardiomyocytes, suggesting that CHIR treatment was necessary to induce these cell fates (FIG. 16b). Subsequent optimization of this protocol revealed that spheroid formation, CHIR treatment, and subsequent incubation in 827-supplemented media were sufficient to induce tubular differentiation, whereas insulin and Wnt inhibition steps were dispensable (FIG. 16c-e; the optimized protocol is shown in FIG. 1a). Conversely, treatment of epiblast spheroids with lower CHIR concentrations resulted in the differentiation of contractile cardiomyocytes, similar to those observed in 2D cultures at higher CHIR concentrations (FIG. 16f). These results suggested that CHIR dose-responsiveness differs in 3D culture, resulting a shift in differentiation from cardiomyocytes to tubular organoids.

Example 13

Tubular Organoids Recapitulate Kidney Development and Architecture

With the new protocol, the Inventors' yield was approximately 90 tubular aggregates per well of a 24-well plate, starting with H9 (WA09) hESCs (FIG. 3a-b). L TL, a marker of kidney proximal tubules, reacted strongly with tubular structures and appeared enriched in tubular lumens (FIG. 3c-d). As L TL reacts strongly with kidney tubules but also with other epithelia, the Inventors performed a more thorough characterization of these organoids with markers of kidney and other organs. Tubules or neighboring mesenchyme expressed nephron progenitor and renal vesicle markers including sine oculis homeobox homolog 2 (SIX2), LIM homeobox 1 (LHX1), neural cell adhesion molecule 1 (NCAM), and paired box gene 2 (PAX2) (FIG. 3c and FIG. 17a). The endocytosis receptors low density lipoprotein-related protein 2 (LRP2/megalin) and cubilin were co-expressed apically and co-localized with L TL in tubule segments (FIG. 3d). Quantification by flow cytometry and co-localization indicated that L TL+cells represented ~25% of the total culture, with cubilin detected in ~70% of L TL+tubules along ~60% of the tubular length (FIG. 17b-e). Apical microvilli and tight junctions were furthermore observed in tubules by electron microscopy (FIG. 3e). The Inventors furthermore inspected these structures for expression of E-cadherin (EGAD), a marker of distal tubule nephron segments The Inventors observed progression of EGAD+ distal tubule to L TL+proximal tubule to capsule-like structures containing POD XL+ cells (presumptive podocytes), consistent with nephron segmentation (FIG. 3f). As podocalyxin is not restricted to podocytes, the Inventors further inspected these organoids for additional markers of podocytes and endothelia. PODXL+cells exhibited a spherical and tightly clustered morphology, did not react with L TL, and co-expressed additional markers of kidney podocytes including Wilms tumor protein (WT1) and synaptopodin, as well as Crumbs 3, a junctional component expressed highly in the kidney glomerulus and at lower levels in tubules (FIG. 3g-h and FIG. 18a-b; see also FIG. 1d). Endothelial cords expressing CD31 and von Willebrand factor (vWF) also arose within organoids, contacting both tubular and podocyte populations (FIG. 3f-i). ~80% of L TL+organoids included endothelial and podocyte cell populations (FIG. 18b). Markers of neuroectoderm (TUJ1) or intestine (CDX2) were absent within organoids, indicating that the tubules did not represent these lineages (FIG. 18c-e); however, separate clusters of TUJ1+ cells were observed in the cultures at a ratio of—1:2 to kidney organoids, and projected axon-like processes towards the tubules (FIG. 18c-e). Such neurons might possibly represent a source of inductive signals for kidney tubular differentiation in the absence of ureteric bud. RNA and protein analysis during the time course of differentiation revealed sequential induction of markers characteristic of mesendoderm, nephron progenitors, and finally proximal tubules and podocytes (FIG. 19a-d). Similar lineages were obtained using a 2D protocol for kidney differentiation, although L TL+structures appeared wider and more diffuse (FIG. 19e). The Inventors concluded that tubular organoids most likely represented the kidney lineage.

Example 14

Tubular Organoids Survive Long-Term and Model Kidney Physiology

Figure 21A:
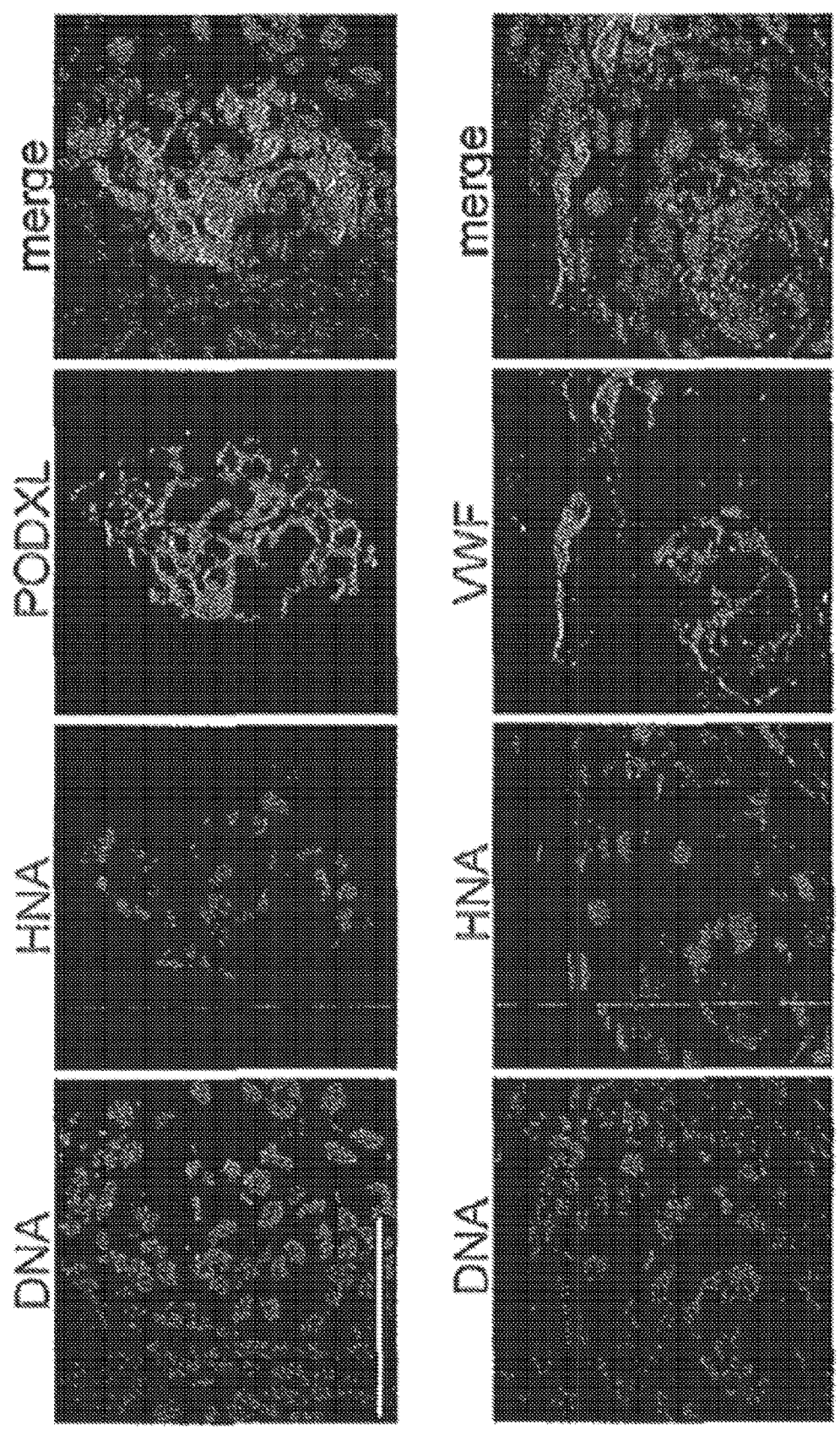

Using this protocol, H9 hESCs and three different hiPSC lines produced organoids incorporating proximal tubules, endothelial cells, and podocytes, in kidney-like arrangements, with hESCs showing the highest efficiency of differentiation (FIG. 4a-b and FIG. 19f). L TL+tubules remained stable in extended cultures for at least 120 days (FIG. 4c). Dynamics of the tubular and endothelial compartments could be visualized in real time by labeling live organoids with fluorescent L TL and antiCD31. When organoids were dissociated and replated in sandwich conditions, new L TL+epithelia, smaller than the original tubules, arose after one week in close proximity to patches of SIX2+ nephron progenitor cells (FIG. 4d-e). Subcultivation was limited to approximately three passages, consistent with the limited capacity of nephron progenitor cells for selfrenewal. When treated with the nephrotoxic drugs cis-diamminedichloroplatinum(ll) (cisplatin) or gentamicin, tubules expressed apical kidney injury molecule-1 (KIM-1), a clinical biomarker of proximal tubule injury (FIG. 4f-g). KIM-1 immunofluorescence was detected in ~80% of organoids after treatment, and was confirmed using two different antibodies (FIG. 4g-h). In contrast, while epiblast spheroids exhibited dose-dependent sensitivity to both cisplatin and gentamicin, they did not upregulate KIM-1 after treatment, indicating that this feature was specific to kidney organoids (FIG. 11 Oa). Organoid cultures could also be miniaturized to a 96-well format amenable to high-throughput experiments (FIG. 4i). Tubular organoid cultures were further dissociated and implanted into kidneys of neonatal immunodeficient mice. After three weeks, the Inventors identified human nuclear antigen-positive (HNA+) epithelial structures within the mouse kidney cortex, with L TL intensities comparable to neighboring mouse tubules (FIG. 4j). Human PODXL+, vwF, and SIX2+ cells were also observed, although the Inventors did not observe formation of vascularized glomeruli (FIG. 4k and FIG. 21a). Collectively, these results demonstrated that tubular organoids can be utilized for in vivo and in vitro investigations relevant to kidney tubular microphysiology and transplantation.

Example 15

Distinct Permeabilities in Kidney Tubules Versus Epiblast Cavities

To test the barrier functions of pluripotent and descendant epithelia, the Inventors developed a real-time assay to visualize molecular diffusion kinetics into and out of lumens, using fluorescent compounds of different sizes. In epiblast spheroids, Lucifer yellow™ (L Y, 521 Da) added to the culture media for 2-4 hours gradually accumulated within cavities, whereas rhodamine-conjugated dextran (RD, 10,000 Da) was excluded from lumens and instead accumulated in apical intercellular regions and formed a bright halo around the lumen (FIG. 5a). Reciprocally, RD microinjected into the cavity remained detectable for hours (FIG. 5b). When fluorescent compounds were incubated with spheroids for several hours and subsequently washed out, the compounds initially retained their distributions, but faded in intensity over time, indicating that they remained dynamic and were not fixed in location (FIG. 5c-d). These findings revealed a functional, size-selective macromolecular permeability barrier at the apical intercellular junctions of the epiblast spheroid epithelium. The Inventors performed parallel experiments assessing transport of fluorescent macromolecules in differentiated tubular organoids. In contrast to epiblast spheroids, RD localized to tubular lumens in ~80% of organoids after 2-4 hours of incubation, and remained associated during a 24-hour washout chase, without corresponding enrichment of L Y (FIG. 5e-f). Co-incubation with latrunculin (Lat)B, an inhibitor of actin polymerization and endocytosis, significantly reduced RD accumulation (FIG. 5g). The transport cargo fluorescein methotrexate (MTX, 979 Da) also accumulated brightly in kidney tubules, similar to RD, but appeared more dynamic than RD after washout (FIG. 5h). MTX was not similarly enriched in hPSC spheroid cavities (FIG. 5i). When organoids loaded with RD were treated with 0.5 mM EDTA for one hour to disrupt tight junctions, luminal RO signal intensity was decreased, suggesting that RO remained mobile (FIG. 22a). 48 hours later, freshly added RO localized to the same tubules in the original distribution pattern (FIG. 22a). Fixation and co-localization revealed that RO was enriched in tubular segments lacking LRP2/megalin, but not in neighboring LRP2/megalin+segments, suggesting localized LRP2/megalin-mediated re-absorption (FIG. 22b). Tubular organoids thus exhibited transport characteristics typical of proximal tubules and distinct from those of epiblast spheroids.

Example 16

Podocalyxin Regulates Epiblast and Podocyte Morphogenesis

The Inventors further applied this system to clarify the role of podocalyxin, an apical sialomucin proposed to regulate epithelial cell differentiation, polarity, and lumen morphogenesis in both epiblast and kidney. Podocalyxin knockout (PODXL-/-.) hPSCs were generated using the clustered regularly interspaced short palindromic repeats (CRISPR)/Cas9 genome editing system, and clones were selected by chromatogram analysis (FIG. 6a-d). lmmunoblots for podocalyxin revealed two major bands at ~220 and 80 kDa that were completely absent in PODXL-/-. hPSCs (FIG. 6e and FIG. 23a). TRA-1-60 and TRA-1-81, two pluripotency markers associated with podocalyxin, were ~40% reduced in knockout cells (FIG. 23b-e). PODXL-/-. hPSCs exhibited teratoma formation, growth rates, and colony size indistinguishable from otherwise isogenic, unmodified hPSCs, indicating that they remained pluripotent and self-renewing (FIG. 6f-h). Strikingly, compared to unmodified controls of otherwise identical genetic background, PODXL-/-. hPSCs in 3D sandwich cultures exhibited a drastic (~85%) decrease in their ability to produce hollow lumens, appearing instead as solid spheroids by phase contrast microscopy (FIG. 6i-j). In the rare cases where PODXL-/-. spheroids did form visible lumens, they were ~70% reduced in diameter (FIG. 6k). These results revealed that podocalyxin was dispensable for the maintenance of pluripotency but required for epiblast spheroid lumenogenesis.

Podocalyxin knockdown by RNA interference (RNAi) was previously shown to disrupt tight junction organization. In PODXL-/-—hESCs, however, the junctional components ZO-1, occludin, and filamentous actin appeared properly localized, and transepithelial electrical resistance (TEER) was indistinguishable from wild-type controls (FIG. 6l-n). Immunofluorescence further revealed small, compressed lumens in PODXL-/-. hESC spheroids, lined with apically polarized ZO-1 (FIG. 24a). L Y added to the media accumulated within these small lumens, while RD was excluded from lumens and accumulated in intercellular foci, similar to wild-type cells (FIG. 24b).

Contrary to these findings in PODXL-/-—hESCs, a ~90% knockdown of podocalyxin by RNA silencing (si-PODXL) resulted in mislocalization of ZO-1 to small patches of residual podocalyxin, confining ZO-1 to ~50% of its normal surface area (FIG. 24c-e). Cavity formation was inhibited by ~50% in siPODXL hPSCs, while total expression levels of ZO-1, OCT4, and NANOG were unaffected (FIG. 24f-h). To investigate whether podocalyxin might contribute directly to luminal expansion via intermolecular charge repulsion, hPSCs were treated with a low concentration (8 µg/ml) of protamine sulfate (PS), a positively-charged polycation which neutralizes the negatively-charged, sialylated extracellular domain of podocalyxin. PS strongly inhibited 3D cavity formation, causing mislocalization of podocalyxin to dispersed patches (FIG. 24i-j). Collectively, these results revealed that podocalyxin promotes epiblast lumenogenesis independently of its association with tight junctions, likely through a direct, charge-mediated mechanism.

The Inventors next investigated podocalyxin function in human kidney cell types. PODXL-/--hPSCs differentiated efficiently into kidney organoids featuring both tubules (ZO-1+LTL+) and podocytes (ZO-1.SYNPO+), despite the complete loss of podocalyxin expression from these cell types (FIG. 7a). PODXL-/--organoids exhibited tubular morphologies and diameters similar to wild-type hPSCs, demonstrating that podocalyxin was dispensable for overall tubular organoid morphogenesis (FIG. 7a-b). ZO-1 expression was similarly unaltered in L TL +tubules differentiated from PODXL-/--hESCs and adopted a cobblestone appearance (FIG. 7c). Notably, in tissue sections from adult human kidneys, podocalyxin was highly expressed in the glomeruli, but was not detected in the tubules (FIG. 7d). The Inventors therefore more closely examined hPSC-derived podocytes by confocal microscopy. In unmodified podocytes, podocalyxin brightly coated the plasma membrane on the exterior of the podocyte aggregate, whereas ZO-1, SYNPO, and β-catenin co-localized in a reciprocal pattern to podocalyxin, forming distinct, internal tracks between adjacent cells within the aggregate (FIG. 7e; see FIG. 1i). In contrast, in PODXL-/- organoids, the appearance of such linear tracks was strongly reduced, with junctional markers adopting a more diffuse expression pattern (FIG. 7f). The disappearance of these tracks in PODXL-/- organoids correlated with a decrease in gap width between adjacent podocytes, compared to isogenic controls (FIG. 7g). The Inventors concluded that podocalyxin regulates junctional organization in kidney podocytes, but not tubules or epiblast cells.

Example 17

Genome-Modified Kidney Organoids form PKD-Specific Cysts

Lastly, the Inventors investigated the potential of kidney organoids to functionally model polycystic kidney disease (PKD), which is characterized by the expansion of kidney tubules to form cysts. Biallelic, loss-offunction mutations in PKD1 or PKD2 are proposed to contribute strongly to PKD cystogenesis. The Inventors therefore applied the CRISPR/Cas9 genome editing system to introduce biallelic, truncating mutations in PKD1 or PKD2 in hPSCs (FIG. 8a-b). Chromatogram analysis and immunoblotting confirmed frame-shift mutations at the target site and demonstrated the absence of the corresponding full-length proteins (FIG. 8c-d). PKD hPSCs demonstrated self-renewal and teratoma formation comparable to isogenic controls (FIG. 8e-f). PKD hPSCs formed cavitated epiblast spheroids with morphologies and luminal diameters similar to controls (FIG. 8g). These spheroids furthermore differentiated with comparable efficiencies into tubular organoids (FIG. 8h). These experiments revealed that PKD1 and PKD2 were dispensable for the maintenance of pluripotency, and did not delectably affect epiblast spheroid cavitation or morphogenesis.

To test whether these lines might produce phenotypes relevant to PKD in the kidney lineage, the Inventors cultured organoids derived from PKD hPSCs for several weeks side-by-side with isogenic, unmodified controls. Remarkably, in the PKD hPSC cultures, the Inventors observed formation of large, translucent, cyst-like structures alongside tubular organoids (FIG. 9a). These structures remained tethered to the underlying matrix, but moved freely in response to vibration, in contrast to neighboring tubular organoids which remained fixed in position near the surface of the dish. These cysts were detected at a low rate, ~5% that of kidney organoids (FIG. 9b). Importantly, isogenic control hPSCs plated and differentiated side-by-side did not form cysts under these conditions (FIG. 9b). PKD cysts first became noticeable ~35 days after the initial plating and continued to expand for the duration of the culture. Cysts exhibited a strong affinity for L TL comparable to neighboring tubules (FIG. 9c) and were observed to arise from tubular structures in time-lapse movies. Confocal microscopy indicated that cyst-lining epithelia surrounded hollow interior compartments devoid of cells (FIG. 9d). Cysts did not delectably accumulate fluorescent cargoes, in contrast to neighboring tubular structures (FIG. 9e). These findings suggested that PKD mutations resulted in aberrant cystogenesis from tubular organoids, in contrast to epiblast spheroids.

Example 18

Discussion

The epithelial characteristics of hPSCs and derived somatic lineages are poorly understood. Reconstitution of epithelial physiology and morphogenesis in both undifferentiated hPSCs and their differentiated descendants is important for advancing their potential as human laboratory models and regenerative therapeutics. The described culture system and assays establish a framework for generating and functionally profiling undifferentiated hPSCs and descendant epithelia in three dimensions. hPSCs are a well-characterized, homogenous, and genetically diverse cell type that includes patient-specific, immunocompatible iPSCs. Well-functioning epithelia may therefore have applicability for regenerative medicine.

The Inventors demonstrate, for the first time, that undifferentiated, epiblast-stage hPSCs form cavitated spheroids in 3D culture, similar to rosettes recently derived from mESCs, but with expanded lumens. Importantly, spheroids form under non-differentiating conditions and remain fully pluripotent, excluding the possibility that they represent a differentiated lineage 14 Spheroid formation is furthermore restricted to the epiblast-stage, but is not characteristic of ICM-stage hPSCs or mESCs. The primate epiblast in vivo is an expanding, discoid epithelial mass that surrounds a highly dynamic early amniotic cavity.

As ethical and legal barriers restrict the study and culture of human embryos at this stage, hPSC spheroids provide an ethically acceptable and experimentally accessible 3D model for epiblast cavitation and subsequent differentiation. Mechanistically, lumen morphogenesis in epiblast spheroids occurs via apicobasal polarization, similar to MOCK cells. The extensive lineage flexibility and genetic diversity of hPSCs is a major advantage over existing epithelial cell models, enabling direct comparisons of human epithelia from diverse tissues and genetic backgrounds. Using genetically modified hPSCs, the Inventors identify podocalyxin as a key mediator of epiblast spheroid lumenogenesis, which functions independently of tight junctions in this cell type.

The Inventors' results suggest a molecular model whereby the combination of apicobasal polarization, tight junction organization, and podocalyxin expression distinguishes epiblast-stage hPSCs from ICM-stage progenitors and promotes formation of the early amniotic cavity (FIG. 10a). Correspondingly, the ability to form lumens in vitro distinguishes primed hPSCs from their niave counterparts. By directly comparing 2D and 3D cultures, the Inventors' studies reveal that spheroid formation at the epiblast stage can significantly affect subsequent cell fate decisions, producing tubular organoids instead of cardiomyocytes. These organoids recapitulate key characteristics of kidney development and physiology in vitro, which have been challenging to model using primary adult or embryonic kidney cells. In contrast to previous protocols for kidney directed differentiation from hPSCs, the Inventors' simple, two-step procedure of spheroid formation followed by CHIR treatment in growth-factor reduced MATRIGEL™ does not require exogenous supplementation with fibroblast growth factor 2 (FGF2), activin, or bone morphogenetic protein. The tubular structures are surrounded by dilute ECM in an adherent, microplate format which is experimentally accessible, scalable, and potentially high-throughput. These structures exhibit a lineage complexity that differs from conventional kidney cell lines and organoids. All the major components of the developing proximal nephron—tubular cells, endothelial cells, nephron progenitors, and podocytes—are represented within each individual organoid, in kidneylike architectures (FIG. 10b). The proximal tubules transport fluorescent cargoes in a characteristic manner, which is distinct from the pluripotent spheroid epithelia from which they derive. When injured, tubules express a clinical biomarker, KIM-1, a response that is highly characteristic of the proximal tubule in vivo but lost in de-differentiated primary cultures. This may provide a quantifiable human standard with which to predict proximal tubule nephrotoxicity, a frequent cause of failure in drug development. PKD is among the most common monogenic diseases and of major interest to both clinicians and cell biologists. Existing cellular systems have reported quantitative differences in the formation of simple spheroids or 'cysts' attributed to defects in PKD gene expression.

However, even wild-type cells frequently form cysts in these systems. A reproducible system for PKD-specific cyst formation from tubules is therefore an important goal for the field, particularly in humans where species-specific pathophysiology and therapy is of clinical interest. The Inventors find that loss-of-function PKD mutations result in cyst formation from hPSC-derived tubular cells, which is not observed in isogenic controls. This finding suggests that PKD-specific cystogenesis from tubules is a cell-intrinsic phenomenon that can be modeled in a minimal system in vitro. As cystogenesis was observed for both PKD1 and PKD2 mutants, and was specific to the kidney organoids but not epiblast spheroids, the phenotype is both gene-specific and lineage-specific in this system. Cysts arise at relatively low frequencies, consistent with the focal appearance of cysts throughout the kidneys of PKD patients and mouse models. Further studies are required to determine the cellular basis of cystogenesis in this system and whether iPSCs from PKD patients, which have heterozygous mutations and variable genetic backgrounds, also produce cysts. As cysts are a relatively rare phenomenon, improvements in iPSC differentiation efficiencies may be required to perform such experiments. In addition to tubular cells, the hPSC system produces podocytes, which are morphologically and functionally distinct from kidney tubules. hPSC-derived podocytes form polarized domains segregating junctional components such as CRB3 and ZO-1, consistent with biochemical and microscopic analyses of podocytes in vivo. The combination of these proteins with podocalyxin, synaptopodin, and WT1 is not known to be co-expressed in any population other than kidney podocytes, nor would such cells be expected to appear alongside L TL+tubular cells in other organs. Using CRISPR knockout lines, the Inventors demonstrate that podocalyxin functions in these cells to segregate junctional complexes basolaterally, analogous to findings during rodent nephrogenesis and in Podxr1 mice As alterations in podocalyxin expression are characteristic of human glomerular disease states, further studies of PODXL-/- podocytes may produce insights into cellular pathophysiology and treatment. The hPSC system does have limitations. For instance, the Inventors have not yet observed formation of a vascularized glomerulus from hPSC podocytes and neighboring endothelia. Dedicated studies involving fluid flow and the tissue microenvironment in vivo are required to further develop this system into fully functional nephrons, for more advanced disease modeling and therapeutic application. In conclusion, the Inventors have developed a 3D culture system that reconstitutes functional, structured epithelia representing the epiblast, kidney tubular cells, and podocytes. These pluripotent and descendant epithelia share certain key structural features, but they can nevertheless recapitulate stage-specific transport characteristics and morphogenesis mechanisms. This provides an accurate and reproducible platform in which to model human microphysiology, injury, and disease at distinct developmental stages. Genome-modified tubular organoids functionally recapitulate kidney disease phenotypes, strengthening the identification of these structures as kidney and establishing innovative cellular systems for studying human renal physiology and pathophysiology in vitro. The described methodologies are broadly applicable and adaptable to diverse tissues and genetically diverse backgrounds, and can be utilized immediately to experimentally investigate molecular pathways relevant to human epithelial diseases. In the longer term, this system may provide a useful setting in which to optimize and test the functionality of patient-derived epithelia in vitro, prior to regenerative graft administration.

Example 19

3D Culture

Cell lines included H9 (WA09), BJ, HDF, hLR5, hfib2-iPS4, and hfib2iPS5 (human) and J1, R1, and v6 (mouse). Cells were maintained feeder-free on 3% Reduced Growth Factor GelTrex™ (Life Technologies) for at least one passage in media (mTeSR1 for hPSCs; N2/B27 supplement+2i in for mESCs; hESC conditioned media (CM)+leukemia inhibitory factor (LIF)+dox for hLR5 iPSCs) and dissociated with Accutase® or TrypLE™. LD-iPSCs were derived from naïve hLR5 iPSCs by withdrawing LIF and doxycycline and substituting with FGF2. For thin gel sandwich colonies, cells were plated at 60,000 (primed) or 30,000 (naïve) cells/well of a 24-well plate or 4-well chamber slide pre-coated with GelTrex™ in media supplemented with 10 µM Rho-kinase inhibitor Y27632 (StemGent). The following day the media was replaced with 500 µL 1.5% GelTrex™ in mTeSR1. Media was changed after 24 hours. For thick gel cultures, 20,000 (epiblast-stage) or 6,000 (naïve) cells/well of a 96-well plate were resuspended in 75 ul of either buffered collagen I (containing 10 mM HEPES and 1×DMEM), reduced growth factor MATRIGEL™ (BD Biosciences), or a 1:1 mixture of the two, incubated for 45 minutes at 37 degrees, and then overlaid with 100 ul of media plus Y27632. For serial passaging in thin gels, colonies with lumens in 3D cultures were dissociated 72 hours after plating, replated at a density of 300,000 cells/well of a 6 well plate, and cultured for 72 hours in either 2D or 3D conditions before dissociation, cell counting, and replating. For suspension, 20,000 dissociated hPSCs were plated in mTeSR1 media in one well of a low-adherence 6-well plate. For all cells, media was changed daily.

Example 20

Tubular Organoid Differentiation 60,000-120,000 H9 hPSCs were plated, sufficient to produce scattered, isolated spheroid colonies. 48 hours after sandwiching, hPSC spheroids were treated with 12 µM CHIR for 36 hours, then changed to RB (Advanced RPMI+Glutamax+B27 Supplement) and replaced every three days thereafter. Alternatively, spheroids were treated with 12 µM CHIR in RB minus insulin (RBNI) for 24 hours, RBNI for 48 hours, 5 µM IWP2 for 48 hours, RBNI for 48 hours, and RB every three days thereafter, as described for 2D cardiomyocyte differentiation. For 2D kidney differentiation, cells were plated overnight and then treated with 8 µM CHIR in APEL™ media (StemCell Technologies) for 48-72 hours, 30 ng/ml FGF2+1 µg/ml heparin in APEL™ media for 96 hours, and subsequently cultured in APEL™ media for 10-15 days. For stochastic differentiation, hPSCs in 2D or 3D cultures were treated with 10% fetal bovine serum (FBS) in DMEM+P/S and observed for 19 days.

Example 21

Immunofluorescence and Electron Microscopy

To fix while preserving 3D architecture, an equal volume of 8% paraformaldehyde was added to the culture media (4% final concentration) for 15 minutes at room temperature. After fixing, samples were washed in PBS, blocked in 5% donkey serum (Millipore)/0.3% Triton-X-100/PBS, incubated overnight in 3% bovine serum albumin/PBS with primary antibodies, washed, incubated with Alexa-Fluor secondary antibodies (Invitrogen), washed, and stained with DAPI or mounted in Vectashield H-1000. Primary antibodies included OCT4 (sc-5279; Santa Cruz), NANOG (RCAB0004PF; Cosmobio), brachyury (sc-17745; Santa Cruz), TRA-1-60 (MAB4360, Millipore), TRA-1-81 (MAB4381; Millipore), acetylated □-tubulin (051M4770; Sigma), ZO-1 (339100; Invitrogen), podocalyxin (AF1658 and AF1556; R&D), CDX2 (-88, Biogenex), AQP1 (AB2219; Millipore), WT-1 (sc-192; Santa Cruz), LHX1 (Developmental Studies Hybridoma Bank), mPODXL (AF1556; R&D), hPODXL (AF1658, R&D), HNA (MAB1281, Millipore), LTL (FL-1321, Vector Labs), SYNPO (sc-21537; Santa Cruz), CD31 (555444; BD), crumbs 3 (HPA013835, Sigma), Na,K-ATPase (ab7671, Abcam), and cleaved caspase-3 (MAB835; R&D). Fluorescence images were captured using a Nikon epifluorescence 90-I (upright), Eclipse Ti (inverted), or confocal C1 microscopes. For electron microscopy, structures were scraped from the plate after 5 minutes of fixation, pelleted at 300 g for four minutes, and the pellet was gently released by pipetting into cacodylate buffer containing 4% formaldehyde and 2% glutaraldehyde, post-fixed with osmium tetroxide, dehydrated in serial ethanols, and embedded in epoxy resin. Semi-thin sections were cut at 1 mm and stained with toluidine blue to identify tubular structures with apparent lumens by light microscopic examination. Ultrathin sections (75 nm) were cut, mounted on 200 mesh copper grids, counterstained with uranyl acetate and lead citrate, and examined in a JEOL JEM-1010 transmission electron microscope.

Example 22

Permeability Assays

To test permeability, media was supplemented with 20 mM HEPES plus Lucifer Yellow™ carbohydrazide potassium salt (Invitrogen, 38 µM) and Rhodamine-B isothiocyanate dextran (Sigma, 0.5 and imaged by confocal microscopy. For microinjection, 5 rhodamine-conjugated dextran solution in mTeSR1 was diluted 1:1 with Phenol Red Solution (0.5%, Sigma) for visualization. 2 nl was microinjected via a pulled glass capillary microneedle on a Nanoject-2 micromanipulator, and monitored in real-time by wide-field epifluorescence. For TEER, 50,000 hPSCs were plated on 24-well transwell plates (Corning) pre-coated with dilute MATRIGEL™. The media was gently exchanged for 10 days until cells were completely confluent. TEER was measured using an EVOM 2™ device (World Precision Instruments).

Example 23

KIM-I Induction

Organoids in identically-plated wells of a 24-well plate were treated with increasing concentrations of gentamicin and cisplatin for 36-48 hours, fixed, and processed for immunofluorescence with KIM-1 antibodies AKG7.9 (Bonventre laboratory) or 1400 (Biogen). Immunofluorescence for KIM-1 was observed at moderate, sub-toxic doses which did not induce gross tubular disintegration.

Example 24

RNA Interference 16 hours after plating, hPSCs were transfected with Dharmacon Smartpool™ siRNAs directed against PODXL, OCT4, or scrambled control in mTeSR1 without antibiotics. Ten hours later, the media was changed and the cells were either cultured in 2D or sandwiched for 3D culture.

Example 25

Cas9/CRISPR Mutagenesis

Constructs encoding green fluorescent protein (GFP)-tagged Cas9 (Addgene 44719) and a guide RNA (Addgene 64711) targeting the second exon of PODXL (GCTACACCTTCACAAGCCCGGGG) [SEQ ID NO: 1], the first exon of PKD2 (GCGTGGAGCCGCGATAACCCCGG) [SEQ ID NO: 2], or the thirty-sixth exon of PKD1 (GTGGGTGCGAGCTTCCCCCCGGG) [SEQ ID NO: 3] were transiently transfected into H9 hESCs, and GFP-expressing cells were isolated by flow cytometric sorting, clonally expanded, and screened for clones with biallelic loss-of-function indels. ~200,000 sorted hESCs were plated per well of a 6-well plate in hESC-conditioned mTeSR1 plus Y27632. Media was replaced the following morning without Y27632 and cells were clonally expanded and the PODXL gRNA region was amplified by PCR. Chromatogram sequences were analyzed manually and mutations were confirmed by immunoblot and immunofluorescence.

Example 26

Transcriptome Profiling hPSCs plated in 2D or 3D were prepared side-by-side using the RNEasy Mini Kit (Qiagen). Samples were QC'd on the Agilent Bioanalyzer to check for high integrity samples. Qualifying samples were then prepped using the TruSeq stranded mRNA library kit (Illumina). Sequencing was performed on an Illumina NextSeq500 75×75 paired end high output run. Samples were aligned to hg19 reference sequence using Tophat2 and differential expression calculated using Cuffdiff.

Example 27

RT-PCR

RNA was prepared on days 2, 10, 14, and 21 after plating during the differentiation time course using the RNeasy Mini Kit (Qiagen). RNA from all time points was reverse transcribed side-by-side using the M-MLV Reverse Transcription System (Promega). Quantitative RT-PCR reactions were run in duplicate using cDNA (diluted 1:10), 300 nM primers, and iQ SYBR Green™ Supermix (Bio-Rad) with the iQ5 Multi-Color Real-Time PCR Detection System (Bio-Rad), using β-actin as the housekeeping gene.

Example 28

Quantification and Statistical Analysis

For fluorescence intensity quantifications, images were taken in a single imaging session and at identical exposures and processed identically. The number of cavitated colonies (ellipsoid with lumen) versus flat colonies (non-ellipsoid or without a lumen) was scored manually in phase contrast images of living cells, in which lumens were discerned more easily than in fixed samples. For apoptosis, cleaved caspase-3 expression was scored manually, confirmed by nuclear condensation, and divided by the total number of nuclei per wide-field epifluorescent image. For ZO-1 areas, individual colonies or subregions expressing ZO-1 were traced manually and surface areas calculate using NIS Elements (Nikon). For each colony, the summed ZO-1 expressing area was expressed as a percentage of the total surface area and then averaged. To quantify intensities, line scans of equal length were drawn through randomly selected structures imaged with identical exposures to obtain raw fluorescence values in NIS Elements software (Nikon). The averaged line scan values were plotted with error bars. For CHIR-induced differentiation, 6000 individual cells were identified in low-magnification immunofluorescence images using Cell Profiler 2.0 and fluorescence intensities were measured automatically. Statistical comparisons utilized a two-tailed t test for two samples with unequal variance (heteroscedastic). Immunoblots were quantified using the ImageJ Gel Analyzer.

Example 29 hPSCs Form Cavitated Spheroids in 3D Culture

To evaluate the tissue-specific functions of undifferentiated hPSCs and descendant hPSC-KCs, the Inventors developed an adherent, 3D culture system for hPSCs that first produced epiblast spheroids and subsequently kidney tubules (FIG. 25a). Dissociated, undifferentiated hPSCs sandwiched between two layers of dilute MATRIGEL™ (0.2 mg/mL) formed compact, ball-like colonies; by 48 hours, these formed internal cavities (FIG. 25b). Mature spheroids consisted of a simple columnar epithelium surrounding a hollow lumen (FIG. 25b-c). Spheroids cells exhibited polarized localization of podocalyxin (PODXL) to the luminal surface, zonula occludens 1 (ZO-1) to apical cell-cell junctions, and β-catenin to primarily basolateral membranes (FIG. 25c). Similar apicobasal polarization patterns were observed in monolayer hPSCs (FIG. 32a).

Figure 32B:
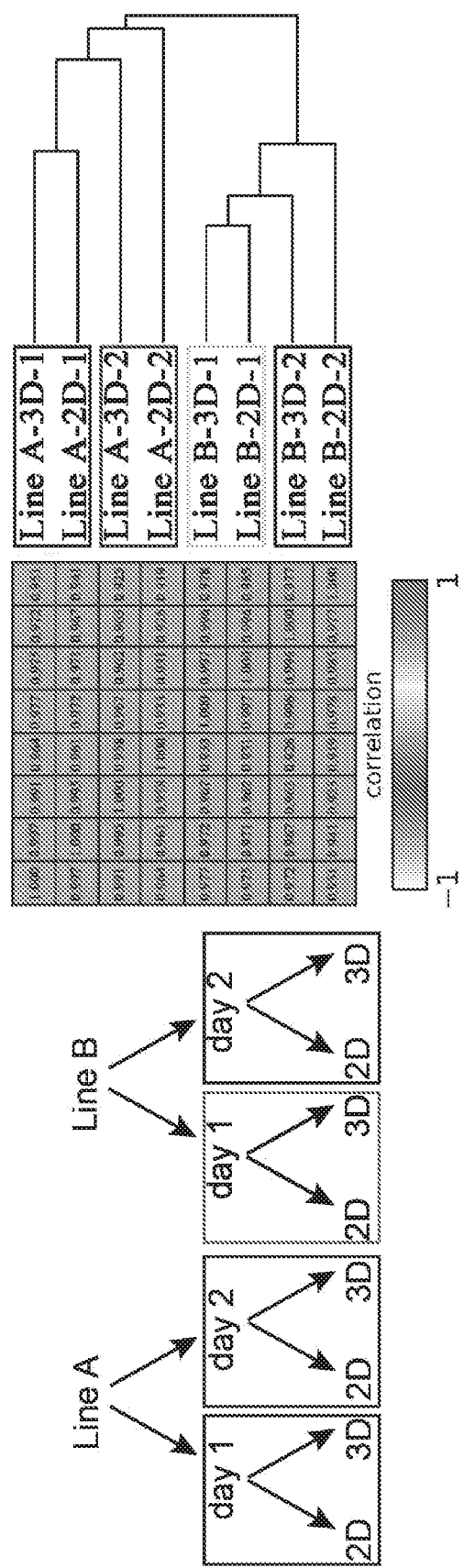

The Inventors further tested hPSC spheroids for pluripotency and self-renewal, which are the key functional characteristics of undifferentiated hPSCs. In nine serial passages, dissociated cavity-lining spheroid cells generated new cavitated spheroids after sandwiching, or alternatively flat colonies when the final passage was into monolayer conditions (FIG. 25d). Even after extensive serial passages to/from 3D culture, cavity-lining cells implanted into immunodeficient mice efficiently produced teratoma tissues derived from all three embryonic germ layers (FIG. 25e). 2D and 3D cultures exhibited similar growth rates, and pluripotency markers continued to be expressed in identical patterns in serially sandwiched cells, including octamer-binding transcription factor 4 (OCT4), sex determining region Y box-2 (SOX2), NANOG, and TRA-1-60 (FIG. 25f-g). 2D colonies and 3D spheroids in pluripotency-sustaining (mTeSR1) media also had nearly identical global gene expression profiles (FIG. 32b). Thus, spheroids represented undifferentiated, self-renewing, pluripotent stem cells rather than a differentiated subtype.

During the development of humans and many other mammals, the ICM of the early embryo differentiates into the epiblast, from which all somatic cells are derived. The Inventors hypothesized that hPSC spheroids model the epiblast epithelial mass, which forms a columnar epithelium surrounding an early amniotic cavity in human and primate implantation-stage embryos. Conversely, hPSCs resembling the more primitive ICM were predicted not to cavitate. Indeed, 'naïve' hLR5 iPSCs, which form compact, ICM-like colonies similar to mouse (m)ESCs, did not form lumens in 3D cultures even after five days of growth, whereas 'primed' hLR5-derived (LD-)iPSCs, which resemble epiblast-stage hPSCs, formed cavities efficiently in sandwich cultures (FIG. 33a-b). Both naïve and primed hPSCs continued to express nuclear OCT4 and SOX2 in both 2D and 3D cultures (FIG. 33c). Similarly, naïve mESCs, which resemble the ICM, did not form cavities under a variety of 3D culture conditions, whereas epiblast-stage mEpiSCs formed rosettes surrounding small lumens (FIG. 33d-f). These experiments identified the epiblast stage as a critical window for hPSC spheroid lumenogenesis, whereas naïve (ICM-stage) hPSCs could not form lumens.

Example 30

GSK3β inhibition Differentiates Spheroids into Tubular Organoids

To differentiate epiblast spheroids into descendant epithelia, the Inventors applied a directed differentiation regimen originally designed for cardiomyocyte generation from 2D cultures, involving the sequential inhibition of glycogen synthase kinase-3β (GSK3β) and Wingless-related integration site (WNT) signaling. Remarkably, rather than form cardiomyocytes, spheroid cells underwent epithelial-to-mesenchymal transition (EMT) to form a confluent monolayer that by day 10 aggregated into folds and initiated mesenchymal-to-epithelial transition (MET) into convoluted, translucent, tubular organoids (FIG. 26a, FIG. 34a-b). Optimization of this new protocol revealed that spheroid formation, treatment with the glycogen synthase kinase-3β inhibitor CHIR99021, and subsequent incubation in B27-supplemented media were sufficient to induce tubular differentiation, whereas insulin and WNT inhibition steps were dispensable (FIG. 34c-d; the optimized protocol is shown in FIG. 26b-c). By comparison, epiblast spheroids examined side-by-side with tubules had negligible affinity for LTL (FIG. 34e). As LTL reacts strongly with kidney tubules but also with certain other epithelia, the Inventors performed a more thorough characterization of these organoids with markers of kidney and other organs. Tubules expressed the nephron progenitor/renal vesicle markers LIM homeobox 1 (LHX1) and paired box gene 2 (PAX2) (FIG. 26b). Sine oculis homeobox homolog 2 (SIX2) was expressed in mesenchyme adjacent to the tubules but not in the tubules themselves, consistent with the developmental restriction of this marker to the metanephric mesenchyme (FIG. 26b). The endocytosis receptors low density lipoprotein-related protein 2 (LRP2/megalin) and cubilin were co-expressed apically and co-localized with LTL in tubule segments (FIG. 26c). Apical microvilli and tight junctions were observed in tubules by electron microscopy (FIG. 26d). The Inventors furthermore observed anatomical progression of tubules from segments expressing E-cadherin (ECAD), a distal tubule marker, to LTL$^+$ segments (proximal tubule), to capsule-like structures containing PODXL$^+$ podocyte-like cells (FIG. 26e). These PODXL$^+$ cells aggregated at the termini of tubules, at the periphery of the organoids (FIG. 26f). They exhibited a spherical and tightly clustered morphology, lacked LTL reactivity, and co-expressed additional markers of kidney podocytes, including Wilms tumor protein (WT1) and synaptopodin (FIG. 26f-g). Endothelial cords expressing CD31 and von Willebrand factor (vWF) also arose within organoids, contacting both tubular and podocyte-like cell populations (FIG. 26g). These results suggested that tubular organoids contained self-organizing hPSC-KC subpopulations capable of nephron-like segmentation and vascular structures.

Using this protocol, H9 hESCs and three different hiPSC lines produced organoids incorporating cells and structures with characteristics of proximal tubules, endothelial cells, and podocytes, in kidney-like segmental arrangements (FIG. 26g). hESCs showed the highest efficiency of differentiation, yielding ~90 organoids/1.9 cm$^2$, with LTL$^+$ cells representing ~25% of the total culture (FIG. 26h and FIG. 35a). ~80% of LTL$^+$ organoids included endothelial (CD31$^+$) and podocyte-like (PODXL$^+$) cell populations (FIG. 26h). Markers of neuroectoderm (TUJ1) or intestine (CDX2) were absent within organoids; however, separate clusters of TUJ1$^+$ cells were observed in the cultures at a ratio of ~1:2 to kidney organoids, and projected axon-like processes towards the tubules (FIG. 35b-d). RNA and protein analysis during the time course of differentiation revealed sequential induction of markers characteristic of mesendoderm, nephron progenitors, and finally proximal tubules and—like cells (FIG. 35e). To assess their potential to engraft in vivo, tubular organoid cultures were dissociated and implanted into kidneys of neonatal immunodeficient mice. After three weeks, the Inventors identified human nuclear antigen-positive (HNA$^+$) epithelial structures within the mouse kidney cortex, with LTL intensities comparable to neighboring mouse tubules (FIG. 26i). The Inventors concluded that tubular organoids most likely represented the kidney lineage.

Example 31

Kidney Organoids Recapitulate Tissue-Specific Injury and Transport

Tissue-specific functions or disease phenotypes have not been demonstrated in hPSC-KCs. The Inventors therefore investigated the potential of kidney organoids to upregulate kidney injury molecule-1 (KIM-1), a clinical biomarker of proximal tubule injury. When treated with the nephrotoxic drugs cis-diamminedichloroplatinum(II) (cisplatin) or gentamicin, KIM-1 immunofluorescence was detected at the luminal surface of tubules in ~80% of organoids, and was confirmed using two different antibodies (FIG. 27a-c). In contrast, while epiblast spheroids exhibited dose-dependent sensitivity to both cisplatin and gentamicin, they did not upregulate KIM-1 after treatment, indicating that this response was specific to kidney organoids (FIG. 27d). Notably, LTL$^+$ tubules remained stable in extended cultures for at least 120 days, and cultures could also be miniaturized to a 96-well format (FIG. 27e-f). Kidney organoids might therefore provide a long-term, high-throughput model system in which to evaluate human nephrotoxicity.

To test whether epiblast spheroids and kidney tubules exhibit tissue-specific barrier functions, the Inventors developed a real-time assay to visualize molecular diffusion kinetics into and out of lumens, using fluorescent compounds of different sizes. In epiblast spheroids, Lucifer yellow™ (LY, 521 Da) added to the culture media for 2-4 hours gradually accumulated within cavities, whereas rhodamine-conjugated dextran (RD, 10,000 Da) was excluded from lumens and instead accumulated in apical intercellular regions and formed a bright halo around the lumen (FIG. 28a). Reciprocally, RD microinjected into the cavity remained detectable for hours (FIG. 28b). Another small molecule, fluorescein methotrexate (MTX, 979 Da), did not accumulate in hPSC lumens (FIG. 28c). When fluorescent compounds were incubated with spheroids for several hours and subsequently washed out, the compounds initially retained their distributions, but faded in intensity over time, indicating that they remained dynamic and were not fixed in location (FIG. 28d). The Inventors performed parallel experiments assessing transport of fluorescent macromolecules in differentiated tubular organoids. In contrast to epiblast spheroids, RD localized to tubular lumens in ~80% of organoids after 2-4 hours of incubation, and remained associated during a 24-hour washout chase, without corresponding enrichment of LY (FIG. 28e-f). Co-incubation with latrunculin (Lat)B, an inhibitor of actin polymerization and endocytosis, significantly reduced RD accumulation (FIG. 28g). MTX also accumulated in kidney tubules, similar to RD, but appeared more dynamic than RD after washout (FIG. 28h). Tubular organoids thus exhibited transport characteristics typical of proximal tubules and distinct from those of epiblast spheroids.

Example 32

Podocalyxin Promotes Epiblast Cavitation Independently of Tight Junctions

Podocalyxin is an apical sialomucin expressed highly in both epiblast and kidney podocytes. To investigate the functional role of podocalyxin in these cell types, podocalyxin knockout (PODXL$^{-/-}$) hPSCs were generated using the clustered regularly interspaced short palindromic repeats (CRISPR)/Cas9 genome editing system (FIG. 36a). Immunoblots for podocalyxin revealed two major bands at ~220 and 80 kDa that were completely absent in PODXL$^{-/-}$ hPSCs (FIG. 29a). TRA-1-60 and TRA-1-81, two pluripotency markers associated with podocalyxin, were ~40% reduced in knockout cells (FIG. 36b). PODXL$^{-/-}$ hPSCs exhibited teratoma formation, growth rates, and 3D colony size indistinguishable from otherwise isogenic, unmodified hPSCs, indicating that they remained pluripotent and self-renewing (FIG. 36c-e). Strikingly, compared to unmodified controls of otherwise identical genetic background, PODXL$^{-/-}$ hPSCs in 3D sandwich cultures exhibited a drastic (~85%) decrease in their ability to produce hollow lumens, appearing instead as solid spheroids by phase contrast microscopy (FIG. 29b-c). Furthermore, podocalyxin expression was much higher in epiblast-stage hPSCs and mEpiSCs, which formed podocalyxin-lined cavities, than in ICM-stage cells, which did not form cavities (FIG. 29d-e). These results revealed that podocalyxin was dispensable for the maintenance of pluripotency but required for epiblast spheroid lumenogenesis.

Podocalyxin is proposed to regulate lumenogenesis through tight junction organization. In PODXL$^{-/-}$ hESCs, however, the junctional components ZO-1, occludin, and filamentous actin appeared properly localized, and transepithelial electrical resistance (TEER) was indistinguishable from wild-type controls (FIG. 29f-h). Although lumens were only very rarely observed by phase contrast microscopy in living cells, immunofluorescence in fixed cultures revealed small, compressed lumens in PODXL$^{-/-}$ hESC spheroids, lined with apically polarized ZO-1 (FIG. 37a). LY added to the media accumulated within these small lumens, while RD was excluded from lumens and accumulated in intercellular foci, similar to wild-type cells (FIG. 37b). These experiments demonstrated that podocalyxin is not required to establish polarized, functional tight junctions in hPSCs. To investigate whether podocalyxin might contribute directly to luminal expansion via intermolecular charge repulsion, hPSCs were treated with a low concentration (8 µg/ml) of protamine sulfate (PS), a positively-charged polycation which neutralizes the negatively-charged, sialylated extracellular domain of podocalyxin. PS strongly inhibited 3D cavity formation, causing mislocalization of podocalyxin to dispersed patches (FIG. 37c-d). Collectively, these results revealed that podocalyxin can promote epiblast lumenogenesis independently of its association with tight junctions, likely through a direct, charge-mediated mechanism.

Example 33

Podocalyxin Regulates Junctions in Podocyte-Like Cells

The Inventors next investigated podocalyxin function in human kidney cell types. In tissue sections from adult human kidneys, podocalyxin was highly expressed in the glomeruli, but was not detected in the tubules (FIG. 30a). Similarly, in hPSC-derived kidney organoids, only podocyte-like cells expressed high levels of podocalyxin (FIG. 30b). The Inventors determined the localization pattern of podocalyxin and junctional markers in these cells by confocal microscopy. Both podocalyxin and another podocyte marker, Crumbs3, brightly coated the plasma membrane on the exterior of podocyte-like aggregates, whereas ZO-1, SYNPO, and β-catenin co-localized in a reciprocal pattern, forming internal zipper-like tracks between adjacent cell layers (FIG. 30c-d). The combined expression of PODXL, Crumbs3, ZO-1, SYNPO, β-catenin, and WT1 (see FIG. 26f) is not known to occur in any population other than kidney podocytes, nor would such cells be expected to appear alongside LTL$^+$ tubular cells in other organs. These results furthermore reveal that hPSC-KC podocyte-like cells form polarized domains segregating junctional components such as Crumbs3 from ZO-1, consistent with biochemical and microscopic analyses of podocytes in vivo.

To investigate podocalyxin function in human podocyte-like cells, the Inventors produced kidney organoids from PODXL$^{-/-}$ hPSCs. In contrast to wild-type organoids, in PODXL$^{-/-}$ organoids, the appearance of linear ZO1$^+$ SYNPO$^+$ tracks was strongly reduced, and junctional markers adopted a more diffuse expression pattern (FIG. 30e). The disappearance of these tracks in PODXL$^{-/-}$ organoids correlated with a decrease in gap width between adjacent podocyte-like cells, compared to isogenic controls (FIG. 30f). The absence of podocalyxin did not affect the efficiency of hPSC-KC differentiation into tubules (ZO-1$^+$LTL$^+$) or podocytes (ZO-1$^+$SYNPO$^+$) (FIG. 38a). Tubules, which expressed little to no detectable podocalyxin, exhibited no defects in their morphologies, diameters, and LTL or ZO-1 expression patterns in PODXL$^{-/-}$ organoids (FIG. 38a-c). The Inventors concluded that podocalyxin is dispensable for kidney organoid differentiation, but is specifically required in podocyte-like cells for proper junctional organization.

Example 34

Genome-Modified Kidney Organoids Form PKD-Specific Cysts

Lastly, the Inventors investigated the potential of kidney organoids to functionally model polycystic kidney disease (PKD), which is characterized by the expansion of kidney tubules to form cysts. Biallelic, loss-of-function mutations in PKD1 or PKD2 are proposed to contribute strongly to PKD cystogenesis. The Inventors therefore applied the CRISPR/Cas9 genome editing system to introduce biallelic, truncating mutations in PKD1 or PKD2 in hPSCs ('PKD hPSCs'). Chromatogram analyses and immunoblotting confirmed frame-shift mutations at the target site and demonstrated the absence of the corresponding full-length proteins (FIG. 31a-b). PKD hPSCs differentiated into teratomas similar to isogenic controls, and formed epiblast spheroids with similarly-sized lumens (FIG. 31c). These experiments revealed that PKD1 and PKD2 were dispensable for the maintenance of pluripotency, and did not detectably affect epiblast spheroid cavitation or morphogenesis.

To test whether these lines might produce phenotypes relevant to PKD in the kidney lineage, the Inventors cultured renal organoids derived from PKD hPSCs for several weeks side-by-side with isogenic, unmodified controls. Remarkably, in the PKD hPSC cultures, the Inventors observed formation of large, translucent, cyst-like structures alongside tubular organoids (FIG. 31d). These structures remained tethered to the underlying matrix, but moved freely in response to vibration, in contrast to neighboring tubular organoids which remained fixed in position near the surface of the dish. These cysts were detected at a low rate, ~6% that of kidney organoids (FIG. 31e). Importantly, isogenic control hPSCs plated and differentiated side-by-side did not form cysts under these conditions (FIG. 31e). No differences were observed in the overall efficiency of organoid differentiation between PKD hPSCs and controls. PKD cysts first became noticeable ~35 days after the initial plating and continued to expand for the duration of the culture. Cysts exhibited a strong affinity for LTL comparable to neighboring tubules (FIG. 31f) and were observed to arise from tubular structures in time-lapse movies. Confocal microscopy indicated that cyst-lining epithelia surrounded hollow interior compartments devoid of cells (FIG. 31g). These findings suggested that PKD mutations resulted in aberrant cystogenesis from tubular organoids, in contrast to epiblast spheroids.

Example 35

Discussion

The epithelial characteristics of hPSCs and derived kidney cells are poorly understood. Reconstitution of epithelial physiology and morphogenesis in these cell types is important for advancing their potential as human laboratory models and regenerative therapeutics. The described culture system and assays establish a framework for generating and functionally profiling undifferentiated hPSCs and descendant hPSC-KCs in three dimensions. hPSCs are a well-characterized, homogenous, and genetically diverse cell type that includes patient-specific, immunocompatible iPSCs. Well-functioning hPSC-derived epithelia may therefore have applicability for regenerative medicine.

The Inventors demonstrate, for the first time, that undifferentiated, epiblast-stage hPSCs form cavitated spheroids in 3D culture, similar to rosettes recently derived from mESCs, but with expanded lumens. By directly comparing 2D and 3D cultures, the Inventors' studies reveal that spheroid formation at the epiblast stage can significantly affect subsequent cell fate decisions, producing tubular organoids instead of cardiomyocytes. These organoids recapitulate key characteristics of kidney development and physiology in vitro, which have been challenging to model using primary adult or embryonic kidney cells. In contrast to previous protocols for kidney directed differentiation from hPSCs, the Inventors' simple, two-step procedure of spheroid formation followed by GSK3βinhibition in growth-factor reduced MATRIGEL™ does not require exogenous supplementation with fibroblast growth factor 2 (FGF2), activin, or bone morphogenetic protein. The tubular structures are surrounded by dilute ECM in an adherent, microplate format which is experimentally accessible, scalable, and potentially high-throughput. These structures exhibit a lineage complexity that differs from conventional kidney cell lines and organoids. All the major components of the developing proximal nephron—tubular cells, endothelial cells, nephron progenitors, and podocyte-like cells—are represented within each individual organoid, in kidney-like architectures. The proximal tubules transport fluorescent cargoes in a characteristic manner, which is distinct from the pluripotent spheroid epithelia from which they derive. When injured, tubules express a clinical biomarker, KIM-1, a response that is highly characteristic of the proximal tubule in vivo but lost in de-differentiated primary cultures. This may provide a quantifiable human standard with which to predict proximal tubule nephrotoxicity, a frequent cause of failure in drug development.

As the Inventors' studies of PODXL$^{-/-}$ hPSCs illustrate, this advanced differentiation system can be combined with CRISPR/Cas9 genome editing to determine the function of specific genes in different human cell types, on an isogenic genetic background. The Inventors' results suggest a molecular model whereby the combination of apicobasal polarization, tight junction organization, and podocalyxin expression distinguishes epiblast-stage hPSCs from ICM-stage progenitors and promotes formation of the early amniotic cavity (FIG. 8a). Although podocalyxin upregulation and tight junction organization occur simultaneously, tight junctions can organize and function independently of podocalyxin in hPSCs. In contrast, in podocyte-like cells, podocalyxin plays a dominant role in the organization of junctions and the spacing of adjacent cells, consistent with reports of tight junction phenotypes during rodent glomerulogenesis and in MDCK cells. Thus, although podocalyxin plays an anti-adhesive role in both epiblast and podocyte, its effect on cell polarity and tight junctions is limited to podocytes. Further investigations are required to determine the precise molecular mechanisms underlying these cell type-specific differences, which suggest the presence of co-regulatory factors present in one cell type but not the other. As alterations in podocalyxin expression and the podocyte cytoskeleton are a well-described characteristic of human glomerular disease states, such studies may produce new insights into pathophysiology and treatment.

PKD is among the most common monogenic diseases and of major interest to both clinicians and cell biologists. Existing cellular systems have reported quantitative differences in the formation of simple spheroids or 'cysts' attributed to defects in PKD gene expression. However, even wild-type cells frequently form cysts in these systems. A reproducible system for PKD-specific cyst formation from tubules is therefore an important goal for the field, particularly in humans where species-specific pathophysiology and therapy is of clinical interest. The Inventors find that loss-of-function PKD mutations result in cyst formation from hPSC-derived tubular cells, which is not observed in isogenic controls. This finding suggests that PKD-specific cystogenesis from tubules is a cell-intrinsic phenomenon that can be modeled in a minimal system in vitro. As cystogenesis was observed for both PKD1 and PKD2 mutants, and was specific to the kidney organoids but not epiblast spheroids, the phenotype is both gene-specific and lineage-specific in this system. Further studies are required to determine the cellular basis of cystogenesis in this system and whether iPSCs from PKD patients, which have heterozygous mutations and variable genetic backgrounds, also produce cysts. As cysts are a relatively rare phenomenon, improvements in iPSC differentiation efficiencies may be required to perform such experiments.

The described hPSC system does have limitations. For instance, the Inventors have not yet observed formation of a vascularized glomerulus from hPSC podocyte-like cells and neighboring endothelia. The tubules also do not contain a full brush border. Although SIX2$^+$ mesenchyme was observed adjacent to tubular cells, the Inventors did not observe evidence of ureteric bud markers in these tubules. Rather, the tubules have characteristics of proximal tubules derived from the SIX2$^+$ mesenchyme, which was induced to differentiate through a non-developmental pathway. Neurons were abundant in these cultures and might possibly represent a source of inductive signals for kidney tubular differentiation in the absence of ureteric bud, similar to embryonic spinal cord. A further limitation of this hPSC-based system is the lack of widely-available fluorescent reporter lines with which to perform lineage tracing experiments. One possible solution to this problem would be to adapt this protocol for mouse EpiSCs, which are similar to hPSCs in phenotype. For instance, EpiSCs from the SIX2-TdTomato reporter mouse might be used to determine with greater certainty whether all tubular cells in the Inventors' system derive from the SIX2$^+$ mesenchyme, using developing kidneys from this mouse as positive controls. Overall, the Inventors' findings suggest that while kidney differentiation is indeed occurring from hPSCs, this process in vitro does not fully recapitulate developmental kidney nephrogenesis. Dedicated studies involving fluid flow and the tissue microenvironment in vivo are required to further develop this system into fully functional nephrons, for more advanced disease modeling and therapeutic application.

In conclusion, the Inventors have developed a 3D culture system that reconstitutes functional, structured epithelia modeling the epiblast, kidney tubular cells, and podocyte-like cells. These pluripotent and descendant epithelia share certain key structural features, but they can nevertheless recapitulate stage-specific transport characteristics and morphogenesis mechanisms. This provides an accurate and reproducible platform in which to model human microphysiology, injury, and disease at distinct developmental stages. Genome-modified tubular organoids functionally recapitulate kidney disease phenotypes, strengthening the identification of these structures as kidney and establishing innovative cellular systems for studying human renal physiology and pathophysiology in vitro. The described methodologies are broadly applicable and adaptable to diverse tissues and genetically diverse backgrounds, and can be utilized immediately to experimentally investigate molecular pathways relevant to human epithelial diseases. In the longer term, this system may provide a useful setting in which to optimize and test the functionality of patient-derived epithelia in vitro, prior to regenerative graft administration.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of spheroids, organoids, methods of generating, characterizing, and producing such cell products, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of generating human tubular organoids, comprising:
   (i) providing a quantity of human pluripotent stem cells (hPSCs);
   (ii) culturing the hPSCs in a first culture medium comprising a ROC kinase inhibitor for at least 24 hours and then culturing the hPSCs sandwiched between two layers of a gelatinous protein mixture secreted by Engelbreth-Holm-Swarm mouse sarcoma cells to form epiblast spheroids, wherein the first medium does not comprise exogenous fibroblast growth factor 2 (FGF2), activin or bone morphogenetic protein; and
   (iii) contacting the epiblast spheroids from step (ii) with a second culture medium comprising at least 12 µM CHIR99021 for at least 24 hours, wherein the second medium does not comprise exogenous fibroblast growth factor 2 (FGF2), activin or bone morphogenetic protein, and
   (iv) culturing the epiblast spheroids from step (iii) with a third culture medium comprising B27 for at least 48 hours, wherein the third medium does not comprise exogenous fibroblast growth factor 2 (FGF2), activin or bone morphogenetic, thereby differentiating the epiblast spheroids into tubular organoids.

2. The method of claim 1, wherein the hPSCs of step (ii) are cultured in a medium lacking leukemia inhibitory factor (LIF) and doxycycline prior to forming epiblast spheroids.

3. The method of claim 1, wherein the hPSCs in step (ii) are cultured in the first culture medium comprising the ROC kinase inhibitor for at least 48 hours.

4. The method of claim 1, wherein the second culture medium and the third culture medium further contain RPMI and steps (iii) and (iv) are performed for a total of at least 7 days.

5. The method of claim 1, wherein the tubular organoids are kidney organoids.

6. The method of claim 1, wherein the tubular organoids express at least one of podocalyxin (PODXL), zonula occluden (ZO-1), and lotus tetragonolobus lectin (LTL).

7. A quantity of tubular organoids made by the method of claim 1.

8. A method of generating tubular organoids, comprising:
   (a) providing a quantity of epiblast spheroids sandwiched between two layers of a gelatinous protein mixture secreted by Engelbreth-Holm-Swarm mouse sarcoma cells and optionally collagen; and
   (b) contacting the epiblast spheroids with a first culture medium comprising at least 12 µM CHIR99021 for at least 24 hours; and then
   (c) culturing the epiblast spheroids with a second medium comprising B27 for at least 48 hours,
   wherein the epiblast spheroids or differentiated progeny thereof are not contacted with exogenous fibroblast growth factor 2 (FGF2), activin, or bone morphogenetic protein, thereby differentiating the epiblast spheroids into tubular organoids.

9. The method of claim 8, wherein the medium comprising B27 further comprises insulin.

10. The method of claim 8, wherein the tubular organoids are kidney organoids.

11. The method of claim 10, wherein the kidney organoids express at least of podocalyxin (PODXL), zonula occluden (ZO-1), and lotus tetragonolobus lectin (LTL).

12. The method of claim 8, further comprising a step, following step (c) of culturing the epiblast spheroids with a medium comprising IWP2 for at least 48 hours.

13. The method of claim 1, wherein the ROC kinase inhibitor is Y27632.

14. The method of claim 8, further comprising a step, following step (c) of culturing the epiblast spheroids in a medium lacking supplementation with at least one of glycogen synthase kinase 3β inhibitor and B27.

* * * * *

UNITED STATES PATENT AND TRADEMARK OFFICE
CERTIFICATE OF CORRECTION

| | |
|---|---|
| PATENT NO. | : 10,815,460 B2 |
| APPLICATION NO. | : 15/756846 |
| DATED | : October 27, 2020 |
| INVENTOR(S) | : Freedman et al. |

It is certified that error appears in the above-identified patent and that said Letters Patent is hereby corrected as shown below:

In the Specification

At Column 1, Line 18:
Insert the following heading and paragraph:
--GOVERNMENT SUPPORT
This invention was made with government support under DK092036, and DK102826 awarded by the National Institutes of Health. The government has certain rights in the invention.--

Signed and Sealed this
Second Day of May, 2023

Katherine Kelly Vidal
Director of the United States Patent and Trademark Office

SEQUENCE LISTING

<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: PODXL

<400> SEQUENCE: 1
gctacacctt cacaagcccg ggg                                              23

<210> SEQ ID NO 2
<211> LENGTH: 23
<212> TYPE: DNA
<213> ORGANISM: Artificial Sequence
<220> FEATURE:
<223> OTHER INFORMATION: Exon 1 PKD2 Exon1

<400> SEQUENCE: 2
gcgtggagcc gcgataaccc cgg                                              23

<210> SEQ ID NO 3
<211> LENGTH: 23
<212> TYPE: DNA
<213> ORGANISM: Artificial Sequence
<220> FEATURE:
<223> OTHER INFORMATION: PKD1 Exon 36

<400> SEQUENCE: 3
gtgggtgcga gcttcccccc ggg                                              23

<210> SEQ ID NO 4
<211> LENGTH: 43
<212> TYPE: DNA
<213> ORGANISM: Artificial Sequence
<220> FEATURE:
<223> OTHER INFORMATION: PODXL WT

<400> SEQUENCE: 4
tccctggcta caccttcaca agcccgggga tgaccaccac cct                        43

<210> SEQ ID NO 5
<211> LENGTH: 43
<212> TYPE: DNA
<213> ORGANISM: Artificial Sequence
<220> FEATURE:
<223> OTHER INFORMATION: PODXL A1

<400> SEQUENCE: 5

```
tccctggcta caccttcaca agccccgggg atgaccacca ccc        43
```

<210> SEQ ID NO 6
<211> LENGTH: 39
<212> TYPE: DNA
<213> ORGANISM: Artificial Sequence
<220> FEATURE:
<223> OTHER INFORMATION: PODXL A1

<400> SEQUENCE: 6

```
tccctggcta caccttcaca agccggatga ccaccaccc        39
```

<210> SEQ ID NO 7
<211> LENGTH: 21
<212> TYPE: DNA
<213> ORGANISM: Artificial Sequence
<220> FEATURE:
<223> OTHER INFORMATION: PKD1 WT

<400> SEQUENCE: 7

```
tgtgccccgc gtacggccac c        21
```

<210> SEQ ID NO 8
<211> LENGTH: 21
<212> TYPE: DNA
<213> ORGANISM: Artificial Sequence
<220> FEATURE:
<223> OTHER INFORMATION: PKD1 A1

<400> SEQUENCE: 8

```
tgtgccccgg tacggccacc c        21
```

<210> SEQ ID NO 9
<211> LENGTH: 21
<212> TYPE: DNA
<213> ORGANISM: Artificial Sequence
<220> FEATURE:
<223> OTHER INFORMATION: PKD1 A2

<400> SEQUENCE: 9

```
tgtgccccgc cgtacggcca c        21
```

<210> SEQ ID NO 10
<211> LENGTH: 21
<212> TYPE: DNA
<213> ORGANISM: Artificial Sequence
<220> FEATURE:
<223> OTHER INFORMATION: PKD2 WT

<400> SEQUENCE: 10

```
gccgcgataa ccccggcttc g        21
```

<210> SEQ ID NO 11
<211> LENGTH: 21
<212> TYPE: DNA
<213> ORGANISM: Artificial Sequence
<220> FEATURE:
<223> OTHER INFORMATION: PKD2 A1

<400> SEQUENCE: 11

```
gccgcgataa ccccggcttc a        21
```

<210> SEQ ID NO 12
<211> LENGTH: 21
<212> TYPE: DNA
<213> ORGANISM: Artificial Sequence

```
<220> FEATURE:
<223> OTHER INFORMATION: PKD2 A2

<400> SEQUENCE: 12
gccgcgatac cccggcttcg a                                              21
```